United States Patent
Ouellet et al.

(10) Patent No.: US 12,139,746 B2
(45) Date of Patent: *Nov. 12, 2024

(54) METHOD OF NUCLEIC ACID ENRICHMENT USING SITE-SPECIFIC NUCLEASES FOLLOWED BY CAPTURE

(71) Applicant: DEPIXUS, Paris (FR)

(72) Inventors: Jimmy Ouellet, Lardy (FR); Jerome Maluenda, Bretigny (FR)

(73) Assignee: DEPIXUS, Paris (FR)

(*) Notice: Subject to any disclaimer, the term of this patent is extended or adjusted under 35 U.S.C. 154(b) by 137 days.

This patent is subject to a terminal disclaimer.

(21) Appl. No.: 17/820,011

(22) Filed: Aug. 16, 2022

(65) Prior Publication Data

US 2023/0086170 A1    Mar. 23, 2023

Related U.S. Application Data

(63) Continuation of application No. 17/312,998, filed as application No. PCT/EP2019/084983 on Dec. 12, 2019, now Pat. No. 11,473,124.

(30) Foreign Application Priority Data

Dec. 12, 2018  (EP) ................... 18306679

(51) Int. Cl.
    C12Q 1/68      (2018.01)
    C12Q 1/6806   (2018.01)
    C12Q 1/683    (2018.01)

(52) U.S. Cl.
    CPC ........... *C12Q 1/6806* (2013.01); *C12Q 1/683* (2013.01)

(58) Field of Classification Search
    CPC ................ C12N 9/22; C12Q 1/6806
    See application file for complete search history.

(56) References Cited

U.S. PATENT DOCUMENTS

| | | | |
|---|---|---|---|
| 10,081,829 | B1 | 9/2018 | Shuber et al. |
| 2014/0113296 | A1 | 4/2014 | Dahl |
| 2016/0208241 | A1 | 7/2016 | Tsai et al. |
| 2020/0181683 | A1 | 6/2020 | Ouellet et al. |
| 2021/0388414 | A1 | 12/2021 | Ouellet et al. |

FOREIGN PATENT DOCUMENTS

| | | |
|---|---|---|
| WO | 92/16659 | 10/1992 |
| WO | 2011/147929 A1 | 12/2011 |
| WO | 2011/147931 A1 | 12/2011 |
| WO | 2013/093005 A1 | 6/2013 |
| WO | 2014/114687 A1 | 7/2014 |
| WO | 2015/071474 A2 | 5/2015 |
| WO | 2016/014409 A1 | 1/2016 |
| WO | 2016/100955 A2 | 6/2016 |
| WO | 2016/177808 A1 | 11/2016 |
| WO | 2016/186946 A1 | 11/2016 |
| WO | 2016/201047 A1 | 12/2016 |
| WO | 2018/013840 A1 | 1/2018 |
| WO | 2019/030306 A1 | 2/2019 |

OTHER PUBLICATIONS

Mertes et al., "Targeted enrichment of genomic DNA regions for next-generation sequencing," Brief Funct Genomics, 2011, 10(6): 374-86.
Garcia-Garcia, "Assessment of the latest NGS enrichment capture methods in clinical context," Sci Rep., 2016, 6:20948.
Slaymaker et al., "Rationally engineered Cas9 nucleases with improved specificity," Science, 2015, 351(6268): 84-86.
Zetsche et al., "Cpf1 is a single RNA-guided endonuclease of a Class 2 CRISPR-Cas system," Cell, 2015, 163(3): 759-771.
Gao et al., "Engineered Cpf1 variants with altered PAM specificities increase genome targeting range," Nat Biotechnol. 2017, 35(8): 789-792.
Cromwell et al., "Incorporation of bridged nucleic acids into CRISPR RNAs improves Cas9 endonuclease specificity," Nat Commun. Apr. 13, 2018;9(1):1448.
Orden Rueda et al., "Mapping the sugar dependency for rational generation of a DNA-RNA hybrid-guided Cas9 endonuclease," Nat Commun. 2017; 8: 1610.
Pingoud and Jeltsch, "Mapping the sugar dependency for rational generation of a DNA-RNA hybrid-guided Cas9 endonuclease," Nucleic Acids Res, 2001, 29(18): 3705-3727.
Zhang et al., "Optimizing the specificity of nucleic acid hybridization," Nat Chem, 2012, 4(3): 208-214.
Strohkendl et al., "Kinetic Basis for DNA Target Specificity of CRISPRCas12a," Molecular Cell, 2018, 71:816-824.

(Continued)

*Primary Examiner* — Kenneth R Horlick
(74) *Attorney, Agent, or Firm* — Arrigo, Lee, Guttman & Mouta-Bellum LLP

(57) ABSTRACT

The present invention relates to a method of isolating a nucleic acid target region from a population of nucleic acid molecules, said method comprising the steps of a) contacting said population of nucleic acid molecules with a Class 2 Type V Cas protein-gRNA complex, wherein the gRNA comprises a guide segment that is complementary to a first site adjacent to said target region, thereby forming a Class 2 Type V Cas protein-gRNA-nucleic acid complex, b) contacting the population of nucleic acid molecules comprising said Class 2 Type V Cas protein-gRNA-nucleic acid complex with at least one enzyme having single-strand 3' to 5' exonuclease activity, thereby forming a 5' single-stranded overhang in said first site, c) removing the Class 2 Type V Cas protein-gRNA complex from the population of step b), d) contacting the population of step c) with an oligonucleotide probe, said probe comprising a sequence that is at least partially complementary to said overhang, thereby forming a duplex between said probe and said overhang, and e) isolating said duplex from the population of nucleic acid molecules of step d), thereby isolating said nucleic acid target region.

19 Claims, 16 Drawing Sheets

Figure 1A:
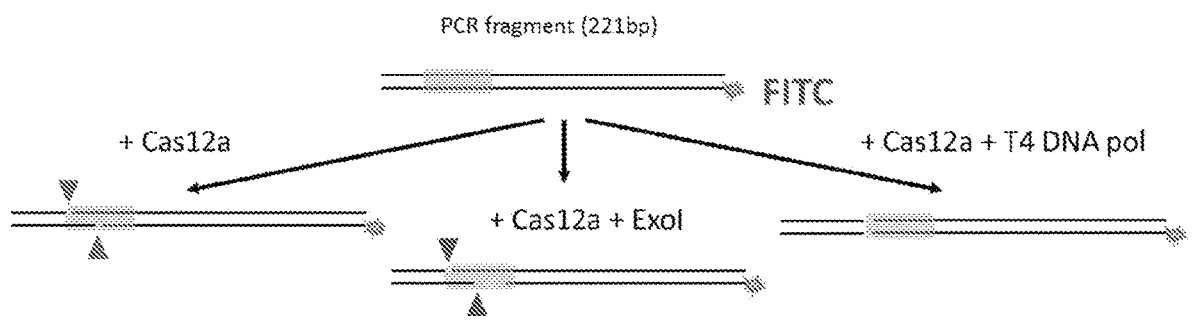

Specification includes a Sequence Listing.

(56) References Cited

OTHER PUBLICATIONS

Gahan, "Circulating nucleic acids in plasma and serum: applications in diagnostic techniques for noninvasive prenatal diagnosis," Int J Womens Health. 2013, 5: 177-186.

Ghorbian and Ardekani, "Non-Invasive Detection of Esophageal Cancer using Genetic Changes in Circulating Cell-Free DNA," Avicenna J Med Biotech. 2012, 4(1): 3-13.

Wojno et al., "Reduced Rate of Repeated Prostate Biopsies Observed in ConfirmMDx Clinical Utility Field Study," American health & drug benefits, 2014, 7(3): 129.

Karvelis et al., "Rapid characterization of CRISPR-Cas9 protospacer adjacent motif sequence elements" Genome Biology, 2015, 16:253.

Request for international preliminary examination under Chapter II PCT, filed in Application No. PCT/EP2019/084983, Oct. 12, 2020.

International Preliminary Report on Patentability, Application No. PCT/EP2019/084983, Oct. 28, 2020.

Hajizadeh Dastjerdi et al, 2019The Expanding Class 2 CRISPR Toolbox: Diversity, Applicability, and Targeting Drawbacks, BioDrugs. Oct. 2019;33(5):503-513.

Tong B et al. The Versatile Type V CRISPR Effectors and Their Application Prospects. Front. Cell Dev. Biol. 2021, 8:622103, 1-11. doi: 10.3389/fcell.2020.622103.

Tong et al., The Versatile Type V CRISPR Effectors and Their Application Prospects, Front. Cell Dev. Biol, 2021, 8, 622103, 1-11.

| Gene | Target | Disease | Chr | Start | End | Target Size |
|---|---|---|---|---|---|---|
| FMR1 | GCC-repeat | Fragile X syndrome | X | 147911033 | 147912743 | 1710 |
| C9orf72 | CpG+GGGGCC-repeat | amyotrophic lateral sclerosis | 9 | 27572678 | 27574118 | 1440 |
| SEPT9.1 | CpG | colorectal cancer | 17 | 77372516 | 77374810 | 2294 |
| SEPT9.2 | CpG | colorectal cancer | 17 | 77450851 | 77451948 | 1097 |
| CNRIP1 | CpG | colorectal cancer | 2 | 68319021 | 68320292 | 1271 |
| FBN1 | CpG | colorectal cancer | 15 | 48644393 | 48646658 | 2265 |
| INA | CpG | colorectal cancer | 10 | 103276677 | 103278492 | 1815 |
| MAL | CpG | colorectal cancer | 2 | 95024889 | 95026822 | 1933 |
| SNCA | CpG | colorectal cancer | 4 | 89836537 | 89837940 | 1403 |
| SPG20 | CpG | colorectal cancer | 13 | 36345467 | 36347222 | 1755 |
| HTT | CpG+CAG-repeat | huntington | 4 | 3073479 | 3075121 | 1642 |
| EGFR | CpG | lung cancer | 7 | 55018205 | 55020556 | 2351 |
| NDRG4.1 | CpG | myofibromatosis | 16 | 58462874 | 58465447 | 2573 |
| NDRG4.2 | CpG | myofibromatosis | 16 | 58500516 | 58501908 | 1392 |
| DMPK | CTG-repeat | Myotonic dystrophy | 19 | 45770028 | 45772277 | 2249 |

Fig. 16A

SEQUENCE LISTING

```
Sequence total quantity: 104
SEQ ID NO: 1            moltype = RNA   length = 44
FEATURE                 Location/Qualifiers
misc_feature            1..44
                        note = Generic single guide RNA for Cpf1
misc_feature            21..44
                        note = n is a, c, g, or u
```

```
source                    1..44
                          mol_type = other RNA
                          organism = synthetic construct
SEQUENCE: 1
taatttctac tcttgtagat nnnnnnnnnn nnnnnnnnnn nnnn              44

SEQ ID NO: 2              moltype = RNA  length = 24
FEATURE                   Location/Qualifiers
misc_feature              1..24
                          note = Target specific sequence of the Cpf1-SETP9.2-crRNA#1
                            (TargetSETP9.2)
source                    1..24
                          mol_type = other RNA
                          organism = synthetic construct
SEQUENCE: 2
tcccctctac cccaggtgct tgct                                    24

SEQ ID NO: 3              moltype = DNA  length = 221
FEATURE                   Location/Qualifiers
misc_feature              1..221
                          note = PCR fragment of SETP9.2 target
source                    1..221
                          mol_type = other DNA
                          organism = synthetic construct
SEQUENCE: 3
tgctccttct cccttccatg gtcccagcca gcaagcacct ggggtagagg ggacaaaccc    60
aggtggctgt gttccagccc tggctgcagg tctgaatggc tttctggggt ggctggccat   120
gctccctgag agcccagctg tggcgatgtc tgagcaggta ggtggggag cacctaggaa    180
gcaggggtgt caggcagagc acaaggagag agggtgtcca g                      221

SEQ ID NO: 4              moltype = DNA  length = 20
FEATURE                   Location/Qualifiers
misc_feature              1..20
                          note = PS1462 PCR oligonucleotide
source                    1..20
                          mol_type = other DNA
                          organism = synthetic construct
SEQUENCE: 4
tgctccttct cccttccatg                                         20

SEQ ID NO: 5              moltype = DNA  length = 20
FEATURE                   Location/Qualifiers
misc_feature              1..20
                          note = PS1464 PCR oligonucleotide tagged with FITC in 5'
source                    1..20
                          mol_type = other DNA
                          organism = synthetic construct
SEQUENCE: 5
ctggacaccc tctctccttg                                         20

SEQ ID NO: 6              moltype = DNA  length = 128
FEATURE                   Location/Qualifiers
misc_feature              1..128
                          note = 129bp FITC tagged PCR fragment
source                    1..128
                          mol_type = other DNA
                          organism = synthetic construct
SEQUENCE: 6
gaatggcttt ctggggtggc tggccatgct ccctgagagc ccagctgtgg cgatgtctga    60
gcaggtaggt gggggagcac ctaggaagca ggggtgtcag gcagagcaca aggagagagg   120
gtgtccag                                                           128

SEQ ID NO: 7              moltype = DNA  length = 272
FEATURE                   Location/Qualifiers
misc_feature              1..272
                          note = 273bp FITC tagged PCR fragment
source                    1..272
                          mol_type = other DNA
                          organism = synthetic construct
SEQUENCE: 7
ggaggaagag ctcagggtga gctgcgcccc catcccctgc cctcctctc ctgctccttc     60
tcccttccat ggtcccagcc agcaagcacc tggggtagag gggacaaacc caggtggctg   120
tgttccagcc ctggctgcag gtctgaatgg cttctgggg tggctggcca tgctccctga    180
gagcccagct gtggcgatgt ctgagcaggt aggtggggga gcacctagga agcaggggtg   240
tcaggcagag cacaaggaga gagggtgtcc ag                                 272

SEQ ID NO: 8              moltype = DNA  length = 503
FEATURE                   Location/Qualifiers
misc_feature              1..503
```

```
                        note = 503bp FITC tagged PCR fragment
source                  1..503
                        mol_type = other DNA
                        organism = synthetic construct
SEQUENCE: 8
cagaggtcgt ggcactgaga tgggtctggc agatcccagc gtccaggccc agccctata     60
gtgtcagctc cctcctctgg ggacccctt gcttgtgccc ctctgggtcc cagcacatcc    120
caggcctgca gggaggggga gaggaagaga ctgactcact ggccaggtcc cccaggggct    180
ggagaggctg gagaggcagg agctggatca gatctgaatc cagaggctct cggaggaaga    240
gctcagggtg agctgcgccc ccatccctg cccctcctct cctgctcctt ctcccttcca    300
tggtcccagc cagcaagcac ctgggggtaga ggggacaaac ccaggtggct gtgttccagc    360
cctggctgca ggtctgaatg gctttctggg gtggctggcc atgctccctg agagcccagc    420
tgtggcgatg tctgagcagg taggtggggg agcacctagg aagcagggt gtcaggcaga    480
gcacaaggag agagggtgtc cag                                             503

SEQ ID NO: 9            moltype = DNA   length = 5225
FEATURE                 Location/Qualifiers
source                  1..5225
                        mol_type = genomic DNA
                        organism = Escherichia coli
SEQUENCE: 9
cagacggtaa ttgttcacct tcgccaaatt cacgacgcg gatcatctgt tccagctctt     60
cttccaccat ttcggagagt ttttacgcg ccagcgggcg gctacgcaag ttgcgaccaa    120
ttgcaggtga agaatcttcg gtttgcgaat caaatgcgtt cataaggccc attctgtaag    180
gtcagtgtga ttaacatcat cagtgacatc ctatcacagg attgaaagta ggggaaaatg    240
gcagggtttt ctctttgtgc ctcatcatta ccataattaa cggaataatt aactattgcg    300
aaaaattaat gtaacgcaga taaaaacatc ccgtttgaat tatttataag actattcacg    360
agcattatga atattatgaa tgtgttctta caaaataatc ataagcgcat attttttaat    420
gaaaaatcac ctcacctaca attaaaaaca cgacatccgc accataaata gccttgcaaa    480
aaatataaca tcgttgtttt caatctgccg tttatggat tgaccgtttt cttttgacac    540
ggagttcaac aatgttcggc ataattatat ctgtcatcgt attaattacg atgggctatt    600
tgatcctgaa aaactacaaa cctcaggtgg tgctggctgc cgcaggtatc ttcctgatga    660
tgtgcggtgt ctggttaggg ttcggtggtg tactcgatcc caccaaaagc agcggctact    720
tgatcgtcga tatttataat gaaatcctgc gcatgctgtc caaccgcatt gccggattgg    780
ggctgtcgat tatggcgtg ggcggttatg cccgctacat ggagcgcata ggggccagtc    840
gcgcgatggt gagcttgtta agccgcccgt taaaactcat tcgctcgccg tatattattc    900
tgtcggcaac ttacgtcatc ggccaaatca tggcgcagtt tattaccagc gcctccggtc    960
tgggtatgtt gctgatggtc accttatttc gacgctggt gagtctggga gtaagtcgtc   1020
tctctgcggt ggcagttatc gcaaccacga tgtccattga gtgggggatt ctggaaacga   1080
actccatttt tgctgcccag gtagcgggaa tgaaaattgc cacatacttc ttccactacc   1140
agcttccggt cgcctcttgc gtcattatct cggtggcgat ctcccacttt ttcgtgcaac   1200
gcgcttttga caaaaagat aaaaatatca atcacgaaca ggcagagcaa aaagctctcg   1260
ataatgtccc gccgctctat tacgccattt tacctgtgat gccgttaatc ctgatgctcg   1320
gctcgctgtt cctcgcccac gtcgggctga tgcagtcaga actgcatctg gtggtggtga   1380
tgttactgag tttgactgtg acgatgtttg ttgagttctt ccgcaagcat aacttgcgcg   1440
aaacaatgga cgatgtgcag gcgttttttg acggcatggg tacgcagttt gccaacgtgg   1500
taacgctggt ggtcgcgggt gaaatatttg ccaaaggctt aacgacgatt ggcactgtcg   1560
atgcggttat caggggggcg gagcattctg gtctgggcgg tattggcgtg atgattatta   1620
tggcgctggt cattgccatt tgtgccattg tgatgggctc tggcaatgcg ccgtttatgt   1680
catttgccag tcttattccg aatatcgcag ccggactaca tgtaccagcg gttgtaatga   1740
ttatgccgat gcattttgcc acgacgctag cgcgcgcggt ttcgccgatt actgcggtag   1800
tggtcgttac gtcaggaatt gcaggcgttt cgccttttgc ggtggtgaag cggacagcga   1860
tccccatggc agtcggtttc gtggtgaata tgattgccac aatcacgcta ttttattaag   1920
tcattaaaaa gacaaaacag gccgcctggg cctgttttgt attacttcac aacgcgtaat   1980
gccggtcgac caccgcgtgg tggctgcgga ggttcatcgt caggatgagt gtcatcatcg   2040
tgatctggct tgtcgccatc aataaccgac ataacggttt cgttgtctgc cgatgcctct   2100
tcatcattca tgatgctggt atcttcatcg taggcagctt caggctcaaa catcgtgcct   2160
gcgccatttt cacgggcgta gatagccagc acggcagcca gcggcacaga aacctgacgc   2220
ggaatgccac caaagcgcgc gttaaagcgc acctcatcat tcgccagttc cagattgccg   2280
acagcacgcg gcgcaatgtt gagtacgatt tgcccgtcac gcgcatattc cataggaacc   2340
tgcacgccag ggagcgtcac atccaccacc aggtgcggcg tgagctggtt atccagcaac   2400
cactcataga atgcacgcag cagataggga cgacgtggtg ttagctgtga caaatccata   2460
cagattaact ccggcccaga cgcatttcac gttctgcttc agttaaagaa gcaaggaaag   2520
agtcacgctc aaagacgcgg gtcatatagc cttcagctc tttcgcaccc gggccgctga   2580
actcgatgcc cagttgcggc agacgccaca gcagcggagc aagatagcaa tcgaccaggc   2640
tgaactcatc gctcaggaag tacggcttct gaccggaagac cggcgcaatc gccagcagtt   2700
cttcgcgcag ttgcttacgt gcggcatctg cttcagaagc tgaaccgttg atgatggtgt   2760
tcatcagcgt gtaccagtct ttttcgatgc gatgcatgta cagacggctt tcaccgcgag   2820
ctacccggta aacaggcatc agtggcggat gcgggaaacg ctcatccaga tattccataa   2880
tgatgcgaga ttcccacagg gtcagctcac gatccaccag ggtcggaacg ctctgattcg   2940
ggttgaggtc aatcagatcc tgaggcggat tgtcctttc cacgtgttcg atctcgaaac   3000
ttacacccttt ctcagccagc acaatgcgga cctgatggct atagatgtca gtaggaccgg   3060
aaaacagcgt cattaccgaa cgtttgttgg cagcgacagc catgaaaacc tccaggtata   3120
gtcagaattt ttactgctac cagccaccag gtggccagtc agaagttgtg ttacccaata   3180
aggaacgact ctctttgttc gaaaatcaaa caaaaaatga gcaatacccg acatttgggc   3240
agaaaattgg atgatagttt accagatttt gcgaccattg tggtgagtcg atgccggaaa   3300
tggggaaaaa gagatgcgct ttagtctgaa atagttgact tagtccctta ttggcgatgt   3360
ggttttgtt ttacctgtct gtcaggtggc agcaaaaagc aactttccag ttttacgct    3420
gattcagatt ttagctataa aaaaacccgc cgaagcgggt ttttcgaaa attgttttct   3480
```

```
gccggagcag aagccaatta acgtttggag aactgcggac gacgacgtgc tttacgcaga   3540
ccgactttct tacgttcaac ctgacgagcg tcacgagtaa cgaagccagc tttacgcagt   3600
tcagaacgca gggactcgtc gtattccatc agagcgcggg tgataccgtg acggatcgca   3660
ccagcctgac cagagatacc accaccttta acgtgatgt  acaggtccag tttctcaacc   3720
atgtcgacca gttccagcgg ctgacgaact accatgcggg cagtttcacg accgaagtac   3780
tgttccagag aacgttggtt gattacgatt ttaccgttgc ccggtttgat gaaaacgcga   3840
gctgcggaac ttttgcggcg accagtgccg tagtattgat tttcagccat tgcctataat   3900
cccgattaga tgtcaagaac ttgcggttgc tgtgccgcgt ggttgtgctc gttacccgcg   3960
taaactttca gtttacggaa catagcacga cccagcgggc cttttggcaa catgccttta   4020
accgcgattt caatcacacg ctcaggacgg cgagcaatca tctcttcaaa ggtcgcttgt   4080
ttgataccac cgatgtggcc ggtgtggtga tagtacactt tgtcagtacg cttgttgccg   4140
gttacagcaa ctttgtcagc gttcagaacg atgatgtaat caccggtatc tacgtgcgga   4200
gtgtattccg ctttgtgctt accgcgcagg cgacgagcca gttcagtagc cagacgggcc   4260
agagttttac cggtcgcgtc aacaacatac cagtcgcgtc tggtttagct   4320
gtaaaagttt tcattaaaag cttacccaat aaatagttac acgttggtga acacccaaac   4380
gtcttcaatt gttgaggttc acgacaaa  gtccggcaaa cctaccccectt cgaatagcct   4440
atgccagcac acaaaaagtt tgggaaaaa  aactttcttg taacgtgggg tcgcaggatt   4500
atagagaagt cggggtcaaa gatcgacccc ttttttgtgat ttgtgacagg ttttaaccccg  4560
ccaaatgctc gcgcttcaga tactcttcgc tttgcatctc ttgcagacgt gacaggcaac   4620
gctggaactc aaacttcagc cgatcgccct gataaatttc atacagcggc acttctgcac   4680
tcaccactaa tttgacatgg cgctcgtaaa actcatccac cagcgcaata aagcgccgcg   4740
cttcgctctc catcaaccgc gtcataactg gtacatcaaa caacatgacc gtatgaaaga   4800
gacgtgagag cgcaatatag tcatgctgac tgcgggcgtc gacgcacagc gtagtaaaag   4860
agaccgccag cgtctggttc tcgacgccca ttgttgctaa tggccgatgg ttgatttcta   4920
acgtcggtga attttctcgt ttccccccccg ccagcgccaa ccatagttta tccatttgcg   4980
cccgggtttc atcgtgaagt ggcgaaagcc acagatgcgc ctgagtgagt gtacgcagac   5040
gataatcaac accagcgtcc acgttcatta catcacaatg ctgtttaatg gcatcgattg   5100
caggcagaaa acgcgcacgt tgcaggccat ttcgataaag ttcatccggc ggaatatttg   5160
acgtcgctac cagggtaata ccgcgagcga acagggcttt catcagaccg ccaagtagca   5220
tggca                                                                5225

SEQ ID NO: 10           moltype = DNA   length = 1643
FEATURE                 Location/Qualifiers
source                  1..1643
                        mol_type = genomic DNA
                        organism = Escherichia coli
SEQUENCE: 10
ttgctaaaga catacgggtt ctccgaaaat taatatttcc aaatttatca agtgcttaaa   60
taattaaatc tgtgctaaaa accaggtaag gatcagtagg tcagcactgc cgcctggact   120
gagatttcgt tcgatacact ccctgtcgaa ctgccggaga taatcgagat cggcgggggt   180
tcgaatgccc cctttttgca ataatgtttg cgcctcgcgc tgtagccagc gcaggccccc   240
ctcgccaccg cgcgatgcaa cgttggtatc gcgttgatc  gccatcagta ggagcaaggt   300
atcgagcaat gccagttcag gatctaaccc ctgatccagc aggatgaggt aatgcggcaa   360
ggcgtgattg atcaccagtg gataacccgc ttcggcttca ccgcgtgcgc cggtaaggcc   420
aagctgttgg tacaaccgtt gacctgccgt cagttgtgaa ttattggtac gcagttcgcg   480
atcggtcagg ccacggcaga aacttgccgc cgtagaacaa acgttgttg  gcgttaccgg   540
ttggttgagt tgaagcaaac ggccaattgc cgcacatagc agccctaaag aaaaaatgct   600
gcctttatgc gtgtttacgc ccgcagtggc gcgaacata  tcaccttcgc aagccatacc   660
aattgggcgt aatccgtgga gtaccgcttc tggtgccatt tccgcactac aggcaccaaa   720
ttcaatgaaa cggggtagcc agccctgaat cgccagcgcg ctgcggtgga atcttccag    780
cgccatatct ttgtgcgcac gcagttaat  gcgatccaac aggcctggtt tcggtgacga   840
attgacttca gtcagcatgg cgcgccagcc cagcaggggcg tactcatcga ttaatgacgt   900
cgcaagcttt gtggttttag ttgacgttgc aggcatcgac atcgttcagc agtgcctcca   960
tgcggttgag taaatcggtc agttgatggg ttttttcacg cgcgcagacg gctgcgcttt   1020
gttcgcacaa caggcagcgg cgaggcggca gtgaatagtc gcggcgggag agaatttcgc   1080
cttcgggcgt caggacatcg atatcccata accgccgag  aggatgacta tgttcaagct   1140
caatggtggc gagcttgagg tcgcgagccg gggcggcaat gctcaacatg ccctccggcc   1200
cgctggcgga aaccagtgca gcctgctcct gaatttgcca gccctgtttt gcggctaagg   1260
cacgcaaggc tgtcacgcca tgattaaaaa ttcggcgtgt gacctcgctg tcttttaatcg   1320
gcccaggcgc aaccacggta aaggagacca gtggaacagg atggcgcttg agccagacgt   1380
gttgccgtgc ttgcctttca tcccggctga cgagcagctc gggaattgat accgcatggt   1440
ggctggcgag ttcaggaagc aggtgcatgg cttattcctt cacctgatgc acaacatcga   1500
tcaccgagcc atcgcggtaa cgcacaacgg caacgacgcg gtctgtgaat tcaatcggct   1560
gtggttcacc ggtcagcaga cgcgcacgtt cgcgcagcca ctcaatggaa accactttaa   1620
tgcccgcttc ctgcagacgt tct                                            1643

SEQ ID NO: 11           moltype = RNA   length = 24
FEATURE                 Location/Qualifiers
misc_feature            1..24
                        note = Target specific sequence of the Cpf1-Ecoli#1-crRNA#1
                        (Target#1)
source                  1..24
                        mol_type = other RNA
                        organism = synthetic construct
SEQUENCE: 11
gcgaaggtga acaattaccg tctg                                            24

SEQ ID NO: 12           moltype = RNA   length = 24
FEATURE                 Location/Qualifiers
```

```
misc_feature          1..24
                      note = Target specific sequence of the Cpf1-Ecoli#1-crRNA#2
                          (Target#1)
source                1..24
                      mol_type = other RNA
                      organism = synthetic construct
SEQUENCE: 12
atcagaccgc caagtagcat ggca                                              24

SEQ ID NO: 13         moltype = RNA   length = 24
FEATURE               Location/Qualifiers
misc_feature          1..24
                      note = Target specific sequence of the Cpf1-Ecoli#2-crRNA#1
                          (Target#2)
source                1..24
                      mol_type = other RNA
                      organism = synthetic construct
SEQUENCE: 13
ggagaacccg tatgtcttta gcaa                                              24

SEQ ID NO: 14         moltype = RNA   length = 24
FEATURE               Location/Qualifiers
misc_feature          1..24
                      note = Target specific sequence of the Cpf1-Ecoli#2-crRNA#2
                          (Target#2)
source                1..24
                      mol_type = other RNA
                      organism = synthetic construct
SEQUENCE: 14
atgcccgctt cctgcagacg ttct                                              24

SEQ ID NO: 15         moltype = DNA   length = 99
FEATURE               Location/Qualifiers
misc_feature          1..99
                      note = PS1466, Oligonucleotide probe for Target#1
source                1..99
                      mol_type = other DNA
                      organism = synthetic construct
SEQUENCE: 15
gtgaatttgg cgaaggtgaa caattaccgt ctgaacgcag aatagggtg aagtagctgg        60
gtcagtgctg caacccactt cctaatctgt catcttctg                              99

SEQ ID NO: 16         moltype = DNA   length = 99
FEATURE               Location/Qualifiers
misc_feature          1..99
                      note = PS1468 Oligonucleotide probe for Target#2
source                1..99
                      mol_type = other DNA
                      organism = synthetic construct
SEQUENCE: 16
ttaattttcg gagaacccgt atgtctttag caaaagatag aatagggtg aagtagctgg        60
gtcagtgctg caacccactt cctaatctgt catcttctg                              99

SEQ ID NO: 17         moltype = DNA   length = 40
FEATURE               Location/Qualifiers
misc_feature          1..40
                      note = PS1467 Oligonucleotide with 5'biotin
source                1..40
                      mol_type = other DNA
                      organism = synthetic construct
SEQUENCE: 17
catcgatctg atgcaagcta cttcacccct attctgcgtt                             40

SEQ ID NO: 18         moltype = DNA   length = 40
FEATURE               Location/Qualifiers
misc_feature          1..40
                      note = PS1469 Oligonucleotide with 5'biotin
source                1..40
                      mol_type = other DNA
                      organism = synthetic construct
SEQUENCE: 18
catcgatctg atgcaagcta cttcacccct attctatctt                             40

SEQ ID NO: 19         moltype = DNA   length = 287
FEATURE               Location/Qualifiers
misc_feature          1..287
                      note = PCR fragment of NDRG4.1 crRNA#1 region
source                1..287
                      mol_type = other DNA
```

```
                                           -continued organism = synthetic construct
SEQUENCE: 19
tgtctttagc tgtcttgtcc aaataaaatt tttcaggcca tcagatttcc gtactccctg    60
gagtgggact tcatctggga ccaaaggagg gctggtgagg ggagtggcag gagggaggag   120
tgcctcgggg ccccgagcag gatgagcctg aggaagagag gggtccccat gttccctttc   180
ccgctcagat aatggaggtg aattgaggga agcagagacc tccccacctt cagggtggga   240
ccctgaggga ccaggacacc tttgctagac ctgtgggaga gaggaac                 287

SEQ ID NO: 20              moltype = RNA   length = 24
FEATURE                    Location/Qualifiers
misc_feature               1..24
                           note = Target specific sequence of the Cpf1-NDRG4.1-crRNA#1
source                     1..24
                           mol_type = other RNA
                           organism = synthetic construct
SEQUENCE: 20
gtcccagatg aagtcccact ccag                                           24

SEQ ID NO: 21              moltype = DNA   length = 58
FEATURE                    Location/Qualifiers
misc_feature               1..58
                           note = Capture Oligonucleotide for NDRG4.1 Target
source                     1..58
                           mol_type = other DNA
                           organism = synthetic construct
SEQUENCE: 21
cctcctttgg tcccagatga agtcccactc cagggagtga ctcagctaac actgagtc      58

SEQ ID NO: 22              moltype = DNA   length = 19
FEATURE                    Location/Qualifiers
misc_feature               1..19
                           note = PS1463 primer
source                     1..19
                           mol_type = other DNA
                           organism = synthetic construct
SEQUENCE: 22
gaatggcttt ctggggtgg                                                 19

SEQ ID NO: 23              moltype = DNA   length = 19
FEATURE                    Location/Qualifiers
misc_feature               1..19
                           note = PS1461 primer
source                     1..19
                           mol_type = other DNA
                           organism = synthetic construct
SEQUENCE: 23
ggaggaagag ctcagggtg                                                 19

SEQ ID NO: 24              moltype = DNA   length = 20
FEATURE                    Location/Qualifiers
misc_feature               1..20
                           note = PS1131 primer
source                     1..20
                           mol_type = other DNA
                           organism = synthetic construct
SEQUENCE: 24
agaggtcgtg gcactgagat                                                20

SEQ ID NO: 25              moltype = RNA   length = 24
FEATURE                    Location/Qualifiers
misc_feature               1..24
                           note = Target specific sequence of the Cpf1-NDRG4.1-crRNA#2
source                     1..24
                           mol_type = other RNA
                           organism = synthetic construct
SEQUENCE: 25
ttaatgaaga aggaggtggc atta                                           24

SEQ ID NO: 26              moltype = RNA   length = 24
FEATURE                    Location/Qualifiers
misc_feature               1..24
                           note = Target specific sequence of the Cpf1-C9orf72-crRNA#1
source                     1..24
                           mol_type = other RNA
                           organism = synthetic construct
SEQUENCE: 26
ccgtaagaca ctgttaagtg catt                                           24

SEQ ID NO: 27              moltype = RNA   length = 24
```

```
FEATURE                 Location/Qualifiers
misc_feature            1..24
                        note = Target specific sequence of the Cpf1-C9orf72-crRNA#2
source                  1..24
                        mol_type = other RNA
                        organism = synthetic construct
SEQUENCE: 27
tattcagaaa caggagggag gtcc                                                  24

SEQ ID NO: 28           moltype = RNA   length = 24
FEATURE                 Location/Qualifiers
misc_feature            1..24
                        note = Target specific sequence of the Cpf1-FMR1-crRNA#1
source                  1..24
                        mol_type = other RNA
                        organism = synthetic construct
SEQUENCE: 28
cattccactg tgaaacaaac ctca                                                  24

SEQ ID NO: 29           moltype = RNA   length = 24
FEATURE                 Location/Qualifiers
misc_feature            1..24
                        note = Target specific sequence of the Cpf1-FMR1-crRNA#2
source                  1..24
                        mol_type = other RNA
                        organism = synthetic construct
SEQUENCE: 29
cggtctagca ttgggacttc ggag                                                  24

SEQ ID NO: 30           moltype = RNA   length = 24
FEATURE                 Location/Qualifiers
misc_feature            1..24
                        note = Target specific sequence of the Cpf1-CNRIP1-crRNA#1
source                  1..24
                        mol_type = other RNA
                        organism = synthetic construct
SEQUENCE: 30
gcttgtattc ctccattctc gctt                                                  24

SEQ ID NO: 31           moltype = RNA   length = 24
FEATURE                 Location/Qualifiers
misc_feature            1..24
                        note = Target specific sequence of the Cpf1-CNRIP1-crRNA#2
source                  1..24
                        mol_type = other RNA
                        organism = synthetic construct
SEQUENCE: 31
cacagatttt gaagggtgag ctat                                                  24

SEQ ID NO: 32           moltype = RNA   length = 24
FEATURE                 Location/Qualifiers
misc_feature            1..24
                        note = Target specific sequence of the Cpf1-DMPK-crRNA#1
source                  1..24
                        mol_type = other RNA
                        organism = synthetic construct
SEQUENCE: 32
ttgtgcatga cgccctgctc tggg                                                  24

SEQ ID NO: 33           moltype = RNA   length = 24
FEATURE                 Location/Qualifiers
misc_feature            1..24
                        note = Target specific sequence of the Cpf1-DMPK-crRNA#2
source                  1..24
                        mol_type = other RNA
                        organism = synthetic construct
SEQUENCE: 33
ctgctggcct ctccagcctt ctca                                                  24

SEQ ID NO: 34           moltype = RNA   length = 24
FEATURE                 Location/Qualifiers
misc_feature            1..24
                        note = Target specific sequence of the Cpf1-EGFR-crRNA#1
source                  1..24
                        mol_type = other RNA
                        organism = synthetic construct
SEQUENCE: 34
gagaggctaa gtgtcccact gccc                                                  24
```

```
SEQ ID NO: 35               moltype = RNA   length = 24
FEATURE                     Location/Qualifiers
misc_feature                1..24
                            note = Target specific sequence of the Cpf1-EGFR-crRNA#2
source                      1..24
                            mol_type = other RNA
                            organism = synthetic construct
SEQUENCE: 35
agccaaccaa aatattaaac ctgt                                              24

SEQ ID NO: 36               moltype = RNA   length = 24
FEATURE                     Location/Qualifiers
misc_feature                1..24
                            note = Target specific sequence of the Cpf1-FBN1-crRNA#1
source                      1..24
                            mol_type = other RNA
                            organism = synthetic construct
SEQUENCE: 36
tgccccaaag gagaggacgt ggtt                                              24

SEQ ID NO: 37               moltype = RNA   length = 24
FEATURE                     Location/Qualifiers
misc_feature                1..24
                            note = Target specific sequence of the Cpf1-FBN1-crRNA#2
source                      1..24
                            mol_type = other RNA
                            organism = synthetic construct
SEQUENCE: 37
gtggctttga aagtatagt attt                                               24

SEQ ID NO: 38               moltype = RNA   length = 24
FEATURE                     Location/Qualifiers
misc_feature                1..24
                            note = Target specific sequence of the Cpf1-HTT-crRNA#1
source                      1..24
                            mol_type = other RNA
                            organism = synthetic construct
SEQUENCE: 38
tgggagtgca ccctgctct gacc                                               24

SEQ ID NO: 39               moltype = RNA   length = 24
FEATURE                     Location/Qualifiers
misc_feature                1..24
                            note = Target specific sequence of the Cpf1-HTT-crRNA#2
source                      1..24
                            mol_type = other RNA
                            organism = synthetic construct
SEQUENCE: 39
ggcccgctgc agctccctgt cccg                                              24

SEQ ID NO: 40               moltype = RNA   length = 24
FEATURE                     Location/Qualifiers
misc_feature                1..24
                            note = Target specific sequence of the Cpf1-INA-crRNA#1
source                      1..24
                            mol_type = other RNA
                            organism = synthetic construct
SEQUENCE: 40
cagttacagt gaggacctgc agag                                              24

SEQ ID NO: 41               moltype = RNA   length = 24
FEATURE                     Location/Qualifiers
misc_feature                1..24
                            note = Target specific sequence of the Cpf1-INA-crRNA#2
source                      1..24
                            mol_type = other RNA
                            organism = synthetic construct
SEQUENCE: 41
tgtccctgcc ccagcccttc aaac                                              24

SEQ ID NO: 42               moltype = RNA   length = 24
FEATURE                     Location/Qualifiers
misc_feature                1..24
                            note = Target specific sequence of the Cpf1-MAL-crRNA#1
source                      1..24
                            mol_type = other RNA
                            organism = synthetic construct
SEQUENCE: 42
cctgcctgtt gactgccggt gttt                                              24
```

```
SEQ ID NO: 43           moltype = RNA  length = 24
FEATURE                 Location/Qualifiers
misc_feature            1..24
                        note = Target specific sequence of the Cpf1-MAL-crRNA#2
source                  1..24
                        mol_type = other RNA
                        organism = synthetic construct
SEQUENCE: 43
cggcacccca ccctcagaag tgtc                                              24

SEQ ID NO: 44           moltype = RNA  length = 24
FEATURE                 Location/Qualifiers
misc_feature            1..24
                        note = Target specific sequence of the Cpf1-NDRG4.2-crRNA#1
source                  1..24
                        mol_type = other RNA
                        organism = synthetic construct
SEQUENCE: 44
ctgcagatat gtcacccacc cccc                                              24

SEQ ID NO: 45           moltype = RNA  length = 24
FEATURE                 Location/Qualifiers
misc_feature            1..24
                        note = Target specific sequence of the Cpf1-NDRG4.2-crRNA#2
source                  1..24
                        mol_type = other RNA
                        organism = synthetic construct
SEQUENCE: 45
gaaggcaccg ccctgggctc tcga                                              24

SEQ ID NO: 46           moltype = RNA  length = 24
FEATURE                 Location/Qualifiers
misc_feature            1..24
                        note = Target specific sequence of the Cpf1-SEPT9.1-crRNA#1
source                  1..24
                        mol_type = other RNA
                        organism = synthetic construct
SEQUENCE: 46
cgaaggaagg tgtgaaggaa ggag                                              24

SEQ ID NO: 47           moltype = RNA  length = 24
FEATURE                 Location/Qualifiers
misc_feature            1..24
                        note = Target specific sequence of the Cpf1-SEPT9.1-crRNA#2
source                  1..24
                        mol_type = other RNA
                        organism = synthetic construct
SEQUENCE: 47
gctggacgcc aagcagagtg ccag                                              24

SEQ ID NO: 48           moltype = RNA  length = 24
FEATURE                 Location/Qualifiers
misc_feature            1..24
                        note = Target specific sequence of the Cpf1-SEPT9.2-crRNA#2
source                  1..24
                        mol_type = other RNA
                        organism = synthetic construct
SEQUENCE: 48
tctaaaatca ctccgctcaa gtta                                              24

SEQ ID NO: 49           moltype = RNA  length = 24
FEATURE                 Location/Qualifiers
misc_feature            1..24
                        note = Target specific sequence of the Cpf1-SNCA-crRNA#1
source                  1..24
                        mol_type = other RNA
                        organism = synthetic construct
SEQUENCE: 49
gtcctgcttc tgatattccc ttct                                              24

SEQ ID NO: 50           moltype = RNA  length = 24
FEATURE                 Location/Qualifiers
misc_feature            1..24
                        note = Target specific sequence of the Cpf1-SNCA-crRNA#2
source                  1..24
                        mol_type = other RNA
                        organism = synthetic construct
SEQUENCE: 50
```

```
ccatcagtgg aacaaggaat aaat                                                24

SEQ ID NO: 51          moltype = RNA   length = 24
FEATURE                Location/Qualifiers
misc_feature           1..24
                       note = Target specific sequence of the Cpf1-SPG20-crRNA#1
source                 1..24
                       mol_type = other RNA
                       organism = synthetic construct
SEQUENCE: 51
cgttccaggt tgttacagcc tttg                                                24

SEQ ID NO: 52          moltype = RNA   length = 24
FEATURE                Location/Qualifiers
misc_feature           1..24
                       note = Target specific sequence of the Cpf1-SPG20-crRNA#2
source                 1..24
                       mol_type = other RNA
                       organism = synthetic construct
SEQUENCE: 52
gaaccagttt tgttgttgtt gtgt                                                24

SEQ ID NO: 53          moltype = DNA   length = 2250
FEATURE                Location/Qualifiers
source                 1..2250
                       mol_type = genomic DNA
                       organism = Homo sapiens
SEQUENCE: 53
cccagagcag ggcgtcatgc acaagaaagc tttgcacttt cgaaccaac gataggtggg          60
ggtgcgtgga ggatggaaca cggacggcc ggcttgctgc cttcccaggc ctgcagtttg         120
cccatccacg tcagggcctc agcctggccg aaagaaagaa atggtctgtg atccccccag        180
cagcagcagc agcagcagca gcagcagcag cagcagcagc agcagcagca gcagcagcat        240
tcccggctac aaggaccctt cgagcccgt tcgccggccg cggacccggc ccctccctcc         300
ccggccgcta gggggcgggc ccggatcaca ggactggagc tgggcggaga cccacgctcg        360
gagcggttgt gaactggcag gcggtgggcg cggcttctgt gccgtgcccc gggcactcag        420
tcttccaacg ggccccgga gtcgaagaca gttctagggt tcaggagcg cggggcggctc         480
ctgggcggcg ccagactgcg gtgagttggc cggcgtgggc caccaaccca atgcagccca        540
gggcggcggc acgagacaga acaacggcga acaggacag ggaaagcgcc tccgataggc         600
caggcctagg gacctgcggg gagagggcga ggtcaacacc ggcatgggc ctctgattgg         660
ctcctgggac tcgccccgcc tacgcccata ggtgggcccg cactcttccc tgcgccccgc        720
ccccgcccca acagcctaca gctgttgtta gtccactcgc acgcctcgaa tcccgtccga        780
actcgtcatt ggctgcttcc tagcggcctg tgttgattgg ctgcccgaag atccgccctc        840
ctgccgtggg cccagccccg caaatgcgca gctaagcgtg tggcaaggg cgggtggagc         900
gcggggcgcg acggcggagg ggggcgtggg cagccggacg tacccttggca gggagcagca        960
ggtggcggcg gtgcatgggg cctggcccca ccagcgggca ctggcccaca gccacggccg       1020
gggggccatc tagctggaga gagaaggac aggtgacccg atcggagccc agcccagccc        1080
tcagcggtgg ggcgagagac agcgagggga atcgaggttg gggaggttat ctagggagat       1140
cccggaggga atctggtgag gcctgaacg agggagatct ggggctgaat aaagggcttc        1200
tgccctctaa agtcgcaaag acgtaggtg agccctatat ctggacgggg agaccaggag        1260
ccagggaggg gatctgcaga atgggcagca ggtctgaggc aggggaaaga gagggtctt        1320
acatggagaag gtgatccgt ggcccgggga ctggggaaca ccgtgacagc tggaaggaga       1380
agaaagaggc atagggcgcg tggagggcg aaggagggcg gtggcgcggc gtgcccagc         1440
gtgggtccct tccctcctcc aggtgtctat acacgccccg cggagcagac ggcccacctc       1500
ctcccggtcc tccggggaag gggacacatg agggactcac ctgtggctcc ctctgcctgc       1560
agcaactcca tccgctcctg caactgccgg acgtgtgcct ctaggtcccg gttccgagcc       1620
tctgcctcgc gtagttgact gtggggaggt aaggacggtg agtccgtccg ggccggacga       1680
gaggggatgc caagggttgc caccggcccg catcccggcc ccggcccggg ccccgatccc       1740
gacctggcga agttctggtt gtccgtgcgg atggcctcca tctcccggct caggctctgc      1800
cgggtgagca cctcctcctc cagggcttcc tggagctccc gcagcgtcac ctcggcctca      1860
gcctctgccg cagggacagc cgctggaact gccacttcag cctgtgtatg gggaccaggc      1920
ttaaggctgc ctgtggctcc tggaagactc aggacttggg cactggttcc aggctaggaa      1980
tccttgttta tccctactc ctccgtcccc tcaacatttc tggaatcccc atagctcctg      2040
caatgatcca agcccctcc cttccctacc tccctcagcc ccatccctga gtctggtcct      2100
ctaaatctac acagggacca gagggctggt gctcaaacac taacacaacc tatgtccctc      2160
tgctgctcaa aatccctcca gctccctaat gcccctcacga caaaaggcct tgctgggttt      2220
tgtttcctgc tggcctctcc agccttctca                                        2250

SEQ ID NO: 54          moltype = DNA   length = 1487
FEATURE                Location/Qualifiers
source                 1..1487
                       mol_type = genomic DNA
                       organism = Homo sapiens
SEQUENCE: 54
aatgcactta acagtgtctt acggtaaaaa caaatttca tccaccaatt atgtgttgag          60
cgccactgc ctaccaagca caaacaaaac cattcaaaac cacgaaatcg tcttcacttt        120
ctccagatcc agcagcctcc cctattaagg ttcgcacacg ctattgcgcc aacgctcctc        180
cagagcgggt cttaagataa aagaacagga caagttgccc cgcccatttt cgctagcctc        240
gtgagaaaac gtcatcgcac atagaaaaca gacagcgta acctacgtg tccgctagg          300
aaagagaggt gcgtcaaaca gcgacaagtt ccgcccacgt aaaagatgac gcttggtgtg        360
```

```
tcagccgtcc ctgctgcccg gttgcttctc ttttggggc gggtctagc aagagcaggt    420
gtgggtttag gaggtgtgtg tttttgtttt tcccaccctc tctccccact acttgctctc    480
acagtactcg ctgagggtga acaagaaaag acctgataaa gattaaccag aagaaaacaa    540
ggagggaaac aaccgcagcc tgtagcaagc tctggaactc aggagtcgcg cgctaggggc    600
cggggcgggg gccggggcgt ggtcgggcg gccccgggcg cgggccgg cggggctgc        660
ggttgcggtg cctgcgcccg cggcggcgga ggcgcaggcg gtggcgagtg ggtgagtgag    720
gaggcggcat cctggcgggt ggctgtttgg ggttcggctg ccgggaagag gcgcgggtag    780
aagcgggggc tctcctcaga gctcgacgca ttttactttt ccctctcatt tctctgaccg    840
aagctgggtg tcgggctttc gcctctagcg actggtggaa ttgcctgcat ccggggcccg    900
ggcttcccgg cggcggcggc ggcggcggcg gcgcaggac aagggatggg gatctggcct    960
cttccttgct ttcccgccct cagtacccga gctgtctcct tcccggggac ccgctgggag   1020
cgctgccgct gcgggctcga gaaaaggag cctcgggtac tgagaggcct cgcctgggg   1080
aaggccggag ggtgggcggc gcgcggcttc tgcggaccaa gtcgggggttc gctaggaacc   1140
cgagacggtc cctgccggcg aggagatcat gcgggatgga atgggggtgt ggagacgcgt   1200
gcacaatttc agcccaagct tctagagagt ggtgatgact tgcatatgag ggcagcaatg   1260
caagtcggtg tgctccccat tctgtgggac atgacctggt tgcttacag ctccgagatg   1320
acacagactt gcttaaagga agtgactatt gtgacttggg catcacttga ctgatggtaa   1380
tcagttgtct aaagaagtgc acagattaca tgtccgtgtg ctcattgggt ctatctggcc   1440
gcgttgaaca ccaccaggct ttgtattcag aaacaggagg aggtcc                  1487

SEQ ID NO: 55         moltype = DNA  length = 1272
FEATURE               Location/Qualifiers
source                1..1272
                      mol_type = genomic DNA
                      organism = Homo sapiens
SEQUENCE: 55
aagcgagaat ggaggaatac aagccaaagg gaaggaaggg gacgaaggcg gacagggagt     60
gacctcttcc tccaacccc gggcccgctg ggagcggcgc gaggcagag gcccttgaga     120
ggctcgggct gtcctggggg cctcagtcct ctgcctgtac cccatggggg accctgctgc    180
caccaggcca cccgcactca ctcgacctgc agcgtgctgg gtttaatctt cacctcaacc    240
ttgtaggagg agccggtgag cagcttgatg gtgcggttct ggccaagcg ctgcccgtcc     300
accttgtaaa agaccgggcc gtcattaggc tggatgcgca gcgcgatgga gaggcgcacg    360
aggcccggca ggtcccccat gtctgggcga gggtctggcg cggcggctcc ggggggcgga    420
ggacagcggg ggctgcggcc gagtggctgg agcgcgaggg gcggagagga agcgcgggga    480
gggtgaggga ggtggtggag ctgaggctgc cgctaggaac ccgcgccgtc gccgccgtcc    540
gcccgggctt ttgaggagca gctccttagg ctgtggcccc cctccccact cggcgaggaa    600
gcgggcccaa gagacggctc caaggccgcg cgcttcccca tccccgctc cagtgctgcg     660
ccctccacgc acccgaaggc tcgctctggc ccgcaggccg ccgcgcagat ccgcgcagct    720
gggggcgagg gagttaatcc tgtttacgca ccacaatccc cttcagctgg gtgaagcgag    780
atttaggctc ctcctagaac agccccgggc aggaggagga gaggtttggg aggcactggg    840
aaggcgctgg agttaagcga ccactatgcc aaggagcgag accccggaa tctggatacc     900
gcctcggcca gctacgtgag gtggacactg ctgctcgcgg atccggcgcc agccaggcgg    960
gaggagccga aggggggta aagggaggcg ggaagggacg acaggaaacc gctagccggt    1020
gatttaaatt tcaggaaata tgagtctttc caaagcttag gggaaatggc cgaggaaagg   1080
cgcaattcca cgtgatggag ccacgctgga tgaggaatgg atgcaagagg aagaaaataa   1140
ccatattcaa ggagctacat cttccttgtgg gtgtacattt ccattatacg tatgctcgtc   1200
ccaaaaatga cacatacata aatatatgta atgaatcaca tatatttaca cagattttga   1260
agggtgagct at                                                       1272

SEQ ID NO: 56         moltype = DNA  length = 2352
FEATURE               Location/Qualifiers
source                1..2352
                      mol_type = genomic DNA
                      organism = Homo sapiens
SEQUENCE: 56
gggcagtggg acacttagcc tctctaaaag cacctccacg gctgtttgtg tcaagccttt     60
attccaagag cttcactttt gcgaagtaat gtgcttcaca cattggcttc aaagtaccca    120
tggctggttg caataaacat taaggaggcc tgtctctgca cccggagttg ggtgccctca    180
tttcagatga tttcgagggt gcttgacaag atctgaagga ccctcggact ttagagcacc    240
acctcggacg cctggcaccc ctgccgcgcg ggcacggcgg cctcctcagc tgccaggcca    300
gcctctgatc cccgagaggg tcccgtagtg ctgcagggga ggtggggacc cgaataaagg    360
agcagtttcc ccgtcggtgc cattatccga cgctggctct aaggctcggc cagtctgtct    420
aaaagctggta caagtttgct ttgtaaaaca aagaagggaa aaggggggaag gggaccctgg   480
cacagatttg gctcgacctg gacataggct gggcctgcaa gtccgcgggg accgggtccg    540
gagggggcagt gctgggaacg cccctctcgg aaattaactc ctcagggcac ccgctcccct    600
ccatgcgcc gccccactcc cgccggagac taggtcccgc ggggccacc gctgtccacc      660
gcctccggcg gccgctggcc ttgggtcccc gctgctggtt ctcctccctc ctcctcgcat    720
tctcctcctc ctctgctcct cccgatccct cctccgccgc ctggtccctc ctcctcccgg    780
cctgcctccc cgccgcctcgg cccgcgcgag ctagacgtcc ggggcagccc cggccgcagc    840
cggccgcagc agcctccgcc cccgcacgg tgtgagcgcc cgacgcggcc gaggcggccg     900
gagtcccgag ctagccccgg cggccgccgc cgcccagacc ggacgacagg ccacctcgtc    960
ggcgtccgcc cgagtcccg cctcgccgcc aacgccacaa ccaccgcgca cggccccctg   1020
actccgtcca gtattgatcg ggagagccgg agcgagctct cggggagca gcgatgcgac   1080
cctccgggac ggccgggga gcgctcctgg cgctgctggg gtcgcggggt acctagccgt   1140
gggctctgga ggaaaagaaa ggtaagggc tgtctcgccg gctcccgcg cgccccgga     1200
tcgcgccccg gaccccgcag cccgcccaac cgcgcaccgg cgcaccggct cggcgcccgc   1260
gccccgcc gtccttcct gtttccttga gatcagctgc ccgccgacc gggaccgcgg      1320
gaggaacggg acgtttcgtt cttcggccgg gagagtctgg ggcgggcgga ggaggagacg   1380
cgtgggacac cggggctgcag gccaggcggg aacggccgc cgggacctcc ggcgccccga   1440
```

```
accgctccca actttcttcc ctcactttcc ccgcccagct gcgcaggatc ggcgtcagtg   1500
ggcgaaagcc gggtgctggt gggcgcctgg ggcggggtc  ccgcacgtgc gccccgcgct   1560
gtcttcccag ggcgcgacgg ggtcctggcg cgcacccgag gggcgggcgc tgcccacccg   1620
ccgagactgc actgtttagg gaagctgagg aaggaaccca aaaatacagc ctcccctcgg   1680
accccgcggg acaggcggct ttctgagagg acctcccccgc ctccgccctc cgcgcaggtc  1740
tcaaactgaa gccggcgccc gccagcctgg ccccggcccc tctccaggtc ccgcgatcc   1800
tcgttcccca gtgtggagtc gcagcctcga cctgggagct gggagaactc gtctaccacc   1860
acctgcggct cccggggagg ggtggtgctg gcggcggtta gtttcctcgt tggcaaaagg   1920
caggtggggt ccgacccgcc ccttgggcgc agacccggc  cgctcgcctc gcccggtgcg   1980
ccctcgtctt gcctatccaa gagtgccccc cacctcccgg ggacccagc  tccctcctgg   2040
gcgcccgcgc cgaaagcccc aggctctcct tcgatggccg cctcgcggag acgtccgggt   2100
ctgctccacc tgcagccctt cggtcgcgcc tgggcttcgc ggtggagcgg gacgcggctg   2160
tccggccact gcagggggg  atcgcgggac tcttgagcgg aagccccgga agcagagctc   2220
atcctggcca acaccatggt gttcaaaat  ggggctcaca gcaaacttct cctcaaaacc   2280
cggagacttt ctttcttgga tgtctctttt tgctgtttga agaatttgag ccaaccaaaa   2340
tattaaacct gt                                                        2352

SEQ ID NO: 57           moltype = DNA  length = 1711
FEATURE                 Location/Qualifiers
source                  1..1711
                        mol_type = genomic DNA
                        organism = Homo sapiens
SEQUENCE: 57
tgaggtttgt ttcacagtgg aatgtaaagg gttgcaagga ggtgcatcgg cccctgtgga     60
caggacgcat gactgctaca cacgtgttca ccccaccctc tggcacaggg tgcacataca    120
gtaggggcag aaatgaacct caagtgctta acacaatttt taaaaaatat atagtcaagt    180
gaaagtatga aaatgagttg aggaaaggc  agtacgtggg tcaaagctgg gtctgaggaa    240
aggctcacat tttgagatcc cgactcaatc catgtccctt aaagggcaca gggtgtctcc    300
acagggccgc ccaaaatctg gtgagagagg gcgtagacgc ctcaccttct gcctctacgg    360
gtcacaaaag cctgggtcac cctggttgcc actgttccta gttcaaagtc ttcttctgtc    420
taatccttca cccctattct cgccttccac tccacctccc gctcagtcag actgcgctac    480
tttgaaccgg accaaaccaa accaaaccaa accaaaccaa accagaccag acaccccctc    540
ccgcggaatc ccagagaggc cgaactggga taaccggatg catttgattt cccacgccac    600
tgagtgcacc tctgcagaaa tgggcgttct ggccctcgcg aggcagtgcg acctgtcact    660
gcccttcagc cttccgcccc tccaccaagc ccgcgcccgc ccggccccgc cgtctgtctt    720
tcgacccggc accccggccg gttcccagca gcgcgcatgc gcgcgctccc aggccacttg    780
aagagagagg gcggggccga ggggctgagc ccgcgggggg agggaacagc gttgatcacg    840
tgacgtggtt tcagtgttta cacccgcagc gggccggggg ttcggcctca gtcaggcgct    900
cagctccgtt tcggtttcac ttccggtgga gggccgcctc tgagcgggcg gggcggcgcg    960
ggcgagcgcg ggcggcggcg gtgacggagg cgccgctgcc aggggcgtg  cggcagcgcg   1020
gcggcggcgg cggcggcggc ggcggcggag gcggcggcgg cggcggcggc ggcggcggct   1080
gggcctcgag cgcccgcagc ccacctctcg ggggcgggct cccggcgcta gcagggctga   1140
agagaagatg gaggagctgg tggtggaagt gcggggcgtc aatggcgctt tctacaaggt   1200
acttggctct agggcaggcc ccatcttcgc ccttccttcc ctcccttttc ttcttggtgt   1260
cggcgggagg caggcccggg gccctcttcc cgagcaccgc gcctgggtgc cagggcacgc   1320
tcggcgggat gttgttggga gggaaggact ggacttgggg cctgttggaa gcccctctcc   1380
gactccgaga ggcctagcg  cctatcgaaa tgagagacca gaggagagg  ggttctcttt   1440
cggcgccgag ccccgccggg gtgagctggg gatgggcgag ggccggcggc aggtactaga   1500
gccgggcggg aagggccgaa atcgcgcta  agtgacggcg atggcttatt ccccttccc    1560
taaacatcat ctcccagcgg gatccgggcc tgtcgtgtgg gtagttgtgg aggagcgggg   1620
ggcgcttcag ccggccgcc  tcctgcagcg ccaagagggc ttcaggtctc ctttggcttc   1680
tcttttccgg tctagcattg ggacttcgga g                                  1711

SEQ ID NO: 58           moltype = DNA  length = 2266
FEATURE                 Location/Qualifiers
source                  1..2266
                        mol_type = genomic DNA
                        organism = Homo sapiens
SEQUENCE: 58
aaccacgtcc tctcctttgg ggcagaaatc tctgggagta ggggcaaggt agtttaacca     60
cgaacgggt  ggggactaaa caaccctagc acctctaagg tgcccccagg aggtcttgcc    120
aaggagtctt ccacagggag agtcatcctg ccgttgttc  tggatcttga aacttgggag    180
acccacacca aaggagggaa ccggttcctt tacccttaa  gcgcgtcgtg tcctccaccg    240
cctcttctct tggcccgact ggctctgtt  tccttcacgt tccagcctc  caaattgcag    300
tccgccccat ggctcgtgta ggacgctaaa agcacgtaa  atcccagggc gatctccagc    360
agacgccctc gacgcatgat gccgagccgc caccggctcc cgccgcctct tgccgcgccc    420
ggggctcggt ctgcggccgc cgctgcgccc tgaagcgcac cgcgccgccg ggtcccgct     480
atccgcgc   ccgtcccccg ggcgggctc  ctccccgctt ctccaggcgc tgctcccact    540
tcaggcggg  cctgccagct gcaacacaga gacaaatccc cgaggcgggg agactttcag    600
ggcatcggga tgctgaagcc tcgcggtccc cattcccaag cccaaccgt  gcgccgcctg    660
cgcgtggcgc agttaattg  ggtaagggaa gaccgtttgg tccacagctg gctgaaaagc    720
ccaggccccc ggcggcagca gcccggccg  atccctcggc ctcccgggcc ccgccagaag    780
agcgcggcgc aaagtaccca tatccccagc ggtcctaagc ccgggcgag  ctctctgggt    840
ttatttttt  tagcggacg  aattgcgcgc ggctgcgcgt ctgaacgccc cactcctcag    900
cctgccctcc ccgccaggct ggaagccagc cgcgccgtcc ccgccgactc cgggcgatgc    960
caccgcccc  cgaacatctg acgcggagcc cggcaccaag agccccgggc caggaagctg   1020
tcaggcaggg gagggccagc gccagctgtg gacgttccgg gacagcccct caccccagtc   1080
cctgtccctg ccctcggcgc ggcgcaaacg caaaagcctc cgtggccgca gctccagccc   1140
cggtggccgc ccgacccccg tcgggacccc ggctgcaccc actggagaag cggcggctcc   1200
```

```
gactcccgag gaggcggcgg cggctgctcc cagtcgtggc cgctacagcc actgctcggc   1260
tccgctcgca gctgtcccag ctgtggctcc tgtccgcttg tggcaccac  agtctctgcc   1320
gcggctcccg cagcccctc  cttcccac   ctcttcaagt atcgtccgcg cagcggtttc   1380
tcgcgagaga aatacttttt ttaaaaaag  aagaaaaag  aaaatgacac cccctccttc   1440
gtcgccctca tcaccacccc acccccggc  cccatccatc ctcccttcc  actcccttt    1500
gccagcctcc gcctcggtgc ggggcctctc gctcgcagga ttagcgcagt gggaggaggc   1560
agaggtgatc aggtcctgcc cggcctggga ctttttgtct tgaggtgggg aggggagaaa   1620
tgggaagagg tggagtagcg gttttagccc gctctgcggc tgcgaggttt agatccgaga   1680
ttaacctctc ccgcgatagg tgaagcccta ccggagcaga aagctgttcc acctgcacca   1740
agaatgcgcg ctggagacgg ttgccccgga ggcctggcc  cgagagaaaa ccagtccccg   1800
ctgcccgcgc ctcccggtag cgcgctccct gcgcctctcc cgccgacac  tcagcagacg   1860
ccggaggccg ggaggctaag actgggcgcg tcgcaggccg ggaccgcggc agaggctgct   1920
gtgccgaccg aggagagggc tctgccgccc ccacttgccc tgggtgtcga gagcccactc   1980
cagacgcggc tcttctgagg ctcaattcaa gccacccagg cctgaatcca gggtgctctc   2040
tctaagtcgg tgtccaaccc aggggcctgt aaatgttgga acctaggatg taggatggga   2100
gcggtgaagg gatggtcctc ttgcccagcc cagattaaga ctgggggttca tctggaggac   2160
tctacttaca ccctcccggt ccctcgccc  tccccacac  acagctgcct ctccccagga   2220
tatgcgcggc acagtgaatt tagtggcttt gaaaggtata gtattt                 2266

SEQ ID NO: 59          moltype = DNA   length = 1643
FEATURE                Location/Qualifiers
source                 1..1643
                       mol_type = genomic DNA
                       organism = Homo sapiens
SEQUENCE: 59
ggtcagagca ggggtgcact cccataaaga aacgccccca ggtcgggact cattcctgtg    60
ggcggcatct tgtggccata gctgcttctc gctgcactaa tcacagtgcc tctgtgggca   120
gcaggcgctg accacccagg cctgcccag  accctctcct ccttccggg  gcgctgcgct   180
gggaccgatg ggggcgcca  ggcctgtgga caccgccctg caggggcctc tccagctcac   240
tggggtggg  gtgggggtca cacttggggt cctcaggtcg tgccgaccac gcgcattctc   300
tgcgctctgc gcaggagctc gcccaccctc tccccgtgca gagagccccg cagctggctc   360
cccgcagggc tgtccgggtg agtatggctc tggccacggg ccagtgtggc ggggagggcaa   420
accccaaggc cacctcggct cagagtccac ggccggctgt cgccccgctc caggcgtcgg   480
cgggggatcc tttccgcatg ggcctgcgcc cgcgctcggc gcccctccca cggccgcgcc   540
ccgtccatgg cccccgtcct catgggcgag ccctccatcg gcctgccctc tccgcgcccc   600
acccctccct cgcccacct  ctcaccttcc tgccccgccc ccagcctccc cacccctcac   660
cggccagtcc cctcccctat cccgctccgc ccctcagccg ccccgccct  cagccggcct   720
gcctaatgtc cccgtcccca gcatcgcccc gccccgcccc cgtctcgccc cgccctcag    780
gcggcctccc tgctgtgccc cgccccgcc  tcgccacgcc cctacctcac cacgccccc    840
gcatcgccac gcccccgca  tcgccacgcc tcccttacca tgcagtcccg ccccgtccct   900
tcctcgtccc gcctcgccgc gacacttcac acacagcttc gcctcacccc attacagtct   960
caccacgccc cgtcccctct ccgttgagcc ccgcgccttc gcccgggtgg ggcgctgcgc  1020
tgtcagcggc cttgctgtgt gaggcagaac ctgcgggggc agggcgggc  tggttcccgc  1080
gccagccatt ggcagagtcc gcaggctagg gctgtcaatc atgctggccg gcgtggcccc  1140
gcctccgccg gcgcggcccc gcctccgccg gcgcagcgtc tgggacgcaa ggcgccgtgg  1200
gggctgccgg gacgggtcca agatggacgg ccgctcaggt tctgcttta  cctgcgggcc  1260
agagcccccat tcattgcccc ggtgctgagc ggcgccgcga gtcggcccga ggcctccggg  1320
gactgccgtg ccgggcggga gaccgccatg gcgaccctgg aaaagctgat gaaggccttc  1380
gagtccctca agtccttcca gcagcagcag cagcagcagc agcagcagca gcagcagcag  1440
cagcagcagc agcagcaaca gccgccaccg ccgccgccgc cgccgccgcc tcctcagctt  1500
cctcagccgc ctcagcaggc acagccgctg ctgcctcagc cgcagccggc cccgccgccg  1560
ccccgccgcc cacccggccc ggctgtggct gaggagccgc tgcaccgacc gtgagtttgg  1620
gcccgctgca gctccctgtc ccg                                          1643

SEQ ID NO: 60          moltype = DNA   length = 1816
FEATURE                Location/Qualifiers
source                 1..1816
                       mol_type = genomic DNA
                       organism = Homo sapiens
SEQUENCE: 60
ctctgcaggt cctcactgta actgaaaaa  cacgacctcg ccctcgggaa ggctttctgt    60
gcgcctcacc tcaggatgag ggtgggtgta ggggacacct cccagaaacc cctaacctcc   120
cagtcggtta aagaagaggg gatagggtca agggatgcga cagagctgtg tggtttccgg   180
atgggaaacc tcagtcgttt aggcacccct ccgctcgagt cacttccgaa gcagtcgatt   240
cttggggaga agcgctgcgg aaaggggcga ctccgatgca gatggccctg tcccggcgca   300
ccaggtcgtc gcgcgcgcag ctgcgtagtc cactgcgcct ccccgcccc  actcctggat   360
gcccccttc  cctctcccgg ccagactctg agcaggagct ccgcccccag cgcgccgccc   420
cagccccggc gccttaaaag ccggggcgac cgccccgccg cgcctgcct  gccgcacctc   480
tccttttcttc tgtagctcgc gttgaagccg cacgtccgcc ccgatccgg gcaccatgag   540
cttcggctcg gagcactacc tgtgctcctc ctcctcctac cgcaaggtgt tcggggatgg   600
ctctcgcctg tccccgccc  tctctggggc cggggcgcg  ggcggcttcc gctcgcagtc   660
gctgtcccgc agcaatgtgg cctctcggc  cgcctgctcc tcggcctcgt cgctcggcct   720
cggcctgggc tatcgccggc gccggcgtc  cgacgggctg gacctgagcc aggcggcggc   780
gcgcaccaac gagtacaaga tcatccgcac caacgagaag gagcagctca agggcctcaa   840
cgaccgcttc gccgtgttca tcgagaaggt gcatcagctg gagacgcaga accgcgcgtt   900
ggaggccgag ctgccgcgc  tgcgacacgc ccacgctgag ccgtcgcgcg tcggcgagct   960
cttccagcgc gagctgcgcg acctgcgcgc cagctggag  gaggccagct cggctcgctc  1020
gcaggccctg ctggagcgcg acgggctggc ggaggaggtg cagcggctgc gggcgcgctg  1080
cgaggaggag agccgcggac gcgaaggcgc cgagcgcgcc ctgaaggcgc agcagcgcga  1140
```

```
cgtggacggc gccacgctgg cccgcctgga cctggagaag aaggtggagt cgctgctgga    1200
cgagctggcc ttcgtacgcc aggtgcacga cgaggaggta gccgagctgc tggccacgct    1260
gcaggcgtcg tcgcaggccg cggccgaggt ggacgtgact gtggctaaac cagacctgac    1320
ctcggctctg agggagatcc gcgcccagta tgagtccctg gccgctaaga acctgcagtc    1380
cgcggaagaa tggtacaagt ccaagtttgc caacctgcac gagcaggcgg cgcgcagcac    1440
cgaggccatc cgggccagcc gcgaggagat ccacgagtat cggcgccagc tgcaggcgcg    1500
caccatcgag atcgagggcc tgcgcggggc caacgagtcc ttggagaggc agatcctgga    1560
gctggaggag cggcacagtg ccgaggtagc tggctaccag gtaagggccg gggctgggcg    1620
tggggagggg tgccctgccc tcttccgcgc gtaccctctt cctctggtaa aactgggccc    1680
caggacttaa ggggagggca aaagagagga gagaagagcc gcggctggag cgctggtta    1740
acaaaaaacc ctggagtctt taatgttaat tttagggaac gcccctcatt tatgtccctg    1800
ccccagccct tcaaac                                                    1816

SEQ ID NO: 61       moltype = DNA  length = 1934
FEATURE             Location/Qualifiers
source              1..1934
                    mol_type = genomic DNA
                    organism = Homo sapiens
SEQUENCE: 61
aaacaccggc agtcaacagg caggcaaaga acctgggggt gggggtagca gcggtccac     60
cctcaaaagg cccgggctgc ccagaccaag agaaagcgat gaatctcttc tggtaacgtc    120
ccttcctgtc gcatggattc aaggccgacc tgccccagca ccaccaccag cagccttctg    180
ctggggccgg cacagctggg agcaacctcc tactctcagg cagacgcgca gcaccaagca    240
gagaggcccg gtgcaggatc ccagcgccga accagcgccg gctcagtgga cgcggaaggg    300
gccggcggcc gcggccggtc ccatccccca ctgcagaccc ccagcctgtg gcggtggtcc    360
agttccgcca ggaaaccgcc gcctggagct gtgggtcgcg cacattaacg catccagcgg    420
aaaaatgaag gagacccaaa ttcaaagtta aagtaatggt gacccgagag gtgccttgat    480
gagaaggttt ggggtcccgg ttactgatgg ttatcattct tacgagatgc tggtcaccta    540
cgaagggaga aaggcacgag gagcgcctga ccaaagtggt tttgccctgc ttcccgcaag    600
aggtggcacc cacggctgga acgcaggagt cagacccaca gtcccagct ctggacgccc     660
gcagcggggc ctcgaagagg ttcaggggcgg tgcccgcggc gctcgggccg gtctcccggg    720
ggcgtggggc gggggggcggg gttgggcggc ggccggggct cctccctctt ctgccccggg    780
ctcccctgct cttaacccgc gcgcggggc gcccaggcca ctgggctccg cggagccagc     840
gagaggtctg cgcggagtct gagcggccgc cgtcccgtcc caaggccgac gccagcacgc    900
cgtcatggcc cccgcacgcg cgacgggcag cagcaccctg cccagtggct tctcggtctt    960
caccaccttg cccgacttgc tcttcatctt tgagtttgtg agtggctcct ggccggggaa    1020
gggacggggt gggctgagcc gtgcgctctc tcgggcgccc agcacagctg tcggacggga    1080
tccgctagct gcgcaggttc tgggagcatc ggggcagcag gcgcagggcg gggactaagc    1140
cagggaagtc ccctcccacc tccggtcctt tgtgcccttc tagaccaaca gaatgagggg    1200
aacagtctac aggactatgg aggaaaaact gggttcccaa ctggggtcag atgtaggcag    1260
cggggcaggg gggacggct cttggttcgc tggtcccaaa gctgcgcgcg gggcccactt     1320
gacgcgcgca gcgccaccga agctcccgcc gcgctttgcg cggttgggta gaagtgcgca    1380
gcttttacaa gggagaaggt ttcgttaaaa aagaaaaaaa aatcagcaag agaaaacatta    1440
gtattaccaa ccgagatttg gagatgagag ggagctgaat ccggtttatt ttcttctggc    1500
cttttaaagt ttctggcgag ggaacgtatt tgcgaccaat tcgatctgga aatgaggcca    1560
tcgtttgctt ggccgcagtc cttctgcccc gtgtgcgggg tgggggtgga gggagatgggg    1620
ggtggggggt gggggggtggc ggcgagagcg atccgcgacg ctcgactgac cttgggcagg    1680
cccgggggcct ctgcacctgc ggtcggtccc gccttgcacg cacggtctct gcctgaggct    1740
gcaggaaagc gcttcctact gagaactcct gataagcgct cacggtgtcg cgaagccgaa    1800
gtgacctccc tcagcctcaa ctcccgggg ccgctggcc ttcacctggg aggggtgtgc      1860
cctgtatgtc ctgtgggtgc ggtccgtcac cgcctgaggg acacctttc cggcacccca    1920
ccctcagaag tgtc                                                     1934

SEQ ID NO: 62       moltype = DNA  length = 2574
FEATURE             Location/Qualifiers
source              1..2574
                    mol_type = genomic DNA
                    organism = Homo sapiens
SEQUENCE: 62
ctggagtggg acttcatctg ggaccaaagg agggctggtg aggggagtgg caggagggag     60
gagtgcctcg gggccccgag caggatgagc ctgaggaaga gacgggtccc catgttccct    120
ttcccgctca gataatggag gtgaattgag gggagcagaa acctcccac cttcagggtg     180
ggaccctgag ggaccaggac accttttgcta ggggatgtcc ctcctcactc ctgcacaagt    240
tcctcaagga cacctcggg ctccgaaaac gggggacgc ccagatgccc ccagaggccc       300
ctgagccct ggttcttccc gaccctaagg gcttttctcc ctcggttccc aggcggggac      360
ggcgggtagc gcgaagcagc aggcgcaggg gcgctgggat ggggatgtct ctgcaggtct    420
aaggttcccc ttgggagtct aaacaaagac tacggcagcg ccgtccctc cccgggaac      480
ccgacgccgc gcggccacag ggggcctgga ggggcgggca gggcctcgca gcgcacccag    540
cacagtccgc gcggcgagc gggtgagaag tcggcgggag gcggatcga cggggtgtc      600
ccccaggctc cgcgtcgcgg tcccgctctc ccctccgcc cgccaccgg gcacccagc       660
cgcgcagaag gcgaagcca cgcgcgaggg accgcgtcc gtcgggact agccccaggc       720
ccggcaccgc cccgcgggcc gagcgcccac accgccaaa cccacgcggg cacgccccg     780
cggcgcaccc cccagccc ggcctccgcc cctgcagccg cgggcacgcg gagggggctcc    840
tggctgccc cacctgcacc cctgctgcgg cccggccgga ggacgacgaag gaccgccag     900
gtctgtctcg tccgcatctc cgcggtgagt cggcggcgcc ctcgccctg agcccagggc    960
cagcttctct cgccgcgcgcg gctgctgcgc gcgtcccgc ccagcccagc ccagcccga    1020
gcacgacccc agcccacgc acgacccctag cccgcgagt cccgcaccga ctcgctcccg    1080
cccccattcgc cctccgcggg ggcggcgccc cctcctcccg gcggctcccg ctctccttcc    1140
tcgccttccc ggccgcgctg ggaccccca gccgccgtcc gcgacccccc accgcgacgc    1200
```

```
ccggaggcgg cggggtctct ttgttcgggc ggcgggcacg ggggaccacc tcccacggtg 1260
tcaccgcacc caccccgcgc ccttcctccg cctcctggag ttcaccggga ccaggtggcg 1320
gcgggtgcct ttttggggt gcgcggccat gcaattggtg gattttttta aaccgttttg 1380
gagggggggag cgcggcgttg ggggcgggag agcgctcctg gctgtgagct gctcctgccg 1440
cttcgctccg cgctctcctg ccgctccgct ccgggtctcc cgcgctcctc tccccggctc 1500
ggccgagcgc gctgccccga cgccgccacc cagagccggg ccgcgccggg cgccgagatg 1560
aaggtgctgg acaccggct ggagctgctc acaggtaccg cccgcctgcc ccgcagccgg 1620
ccgccacttt ccgagttgga gcggactccg ggcgcggcgg ccggggactg gggcggctcg 1680
ggtctgagca ggaaggggtg cggaccccaa ctaagtccta gttttgtgct acctgtttgt 1740
gtgcggagcc cagccccggg agaggacttg aggttgtggc gagtccctgg cgctggcgtc 1800
cgggctgcgg gagcaccggt caggggtgg cccatggggg tctctgacca gcggagctcg 1860
gattaggacc ctgaaagcta gctcagggct cctgccctcc aatcagtgtc gcttgtcccc 1920
taagaaagga cccgtgggct tctggcagga cccgcgccat ggacctctta tttctgcgc 1980
ctgtgacaat ctgagccgtc tttctctggg ggagaagttt cttgctgcag gtggaggcga 2040
cgccaagtgg cctgggaagt gggaagccag attggaccct actgactggg gaccctcagc 2100
cttgggctc ctctggagaa gtgatcagtt gccctgctgg aaactcacat ccaggggggca 2160
gtggctggag agcaagagcg aacggtcagg aagaggaggt gggaaaggga gcaggacgg 2220
ggggaggat tcgaggggagtg acttctgtgt tctccccggt gtggagagac ccagacagga 2280
ggaaaggaaa gcaaccccggt ttcctccagc tctgggactt ataggtgctc catccgtgta 2340
tgtcagatga gcacagattc cagtaagtgt cctccgacac ctgggggagg gggctgatca 2400
ctgccttcca ggaccttaat gtccgatgag ggagcagagc cccggagccc tgttacaagg 2460
ctggaagggg cagccgtctg tgggtgcgct caggaaacgt tggaatccga gtcggggca 2520
gcttttgaag acctcgaaaa acaatttttg ttaatgaaga aggaggtggc atta      2574

SEQ ID NO: 63          moltype = DNA   length = 1393
FEATURE                Location/Qualifiers
source                 1..1393
                       mol_type = genomic DNA
                       organism = Homo sapiens
SEQUENCE: 63
gggggggtggg tgacatatct gcaggaaatg gaacgtggaa ggcactgtct gacttggctg  60
cattgcccgt gtggacccgg gcgctagtgc ctgcatgtcc ctctgaccgt gtgccctctg 120
gtgtgcgctt ggatggtgtc tgccttggtg atgcctgggg ccatcaggcc aggggggcggg 180
ggtgtccttg gtgagccccc gaggctgtgt gcccagtgtg cgtgccgggt ctgtgcgtgc 240
aggggctgcc gtcccagtgg gcggccgtct agcttgtttg gatgcgtgcc cagtgtgat 300
gggaaggaca ggcggcctct tccttaggag ccacctcaca gttcccaggg ctctgctgcg 360
ccagccgggc agaggcaagg aggtctgggc cacacaggaa tgacagcctt tcaggcaggg 420
gtccctgctg ggaggaacg aggagggggtt gcctgcctgc cttatttgt aggtggggga 480
aggcaacgct ggagccgtga agctggcagg gctaggggac cccaggtgga gcccagggca 540
cctcctctcg ccggggcatc aggtaccccg gccccattct tcctcaggag ggagaggcag 600
gggcagactc accccccaccc ccgggcccca cacgcctgcc ctgccggttc cgcagacgat 660
aggtcacccc gcacgcacgg aggtgacgac gtcagcacct gccgcccat gcagaccctg 720
tccctgaat tattgatgcg gctgacaggc cgaaccacag caccaccagc aaccaactgc 780
acaccggcgc aaagcccggc tcaaagcccc actccccctcc agtgctcaag gtcacaggcg 840
agggagacg gaccgaccga gaggagccgc cacagccccc tccccctgctg ccgcagtgct 900
tcccgcctgc gcctacctgg aggcggggcc ggctctgacg tcacccagag ccaatgggag 960
tgctcgggcc tgaggggttgg gggcctcaga gtgcaccggg ctgtggccct tgtgggcg 1020
ccccttgcgca cgctccaag ggacgggat gtttggcttc gatcaggctg aactgagtcc 1080
tgagctctcc gcagagggtg agagaaggcg ttagggaggt tcgcagcagg gttcagcgaa 1140
ggtcactgga cttcgtagga caggtagccc ggtgacgccc aggcccagcc ccagcccttc 1200
ccatcctggg agatgagccc tagtagagcc tgatcacgtc acctcagggg gatgggggca 1260
ggggcggcca caccagggct gggagaagac agtgggggcct cctcagcagc agagagcaga 1320
caccccctcac acccctcagg cggacccgca cgctgcgggt ctgggttttgg aaggcaccgc 1380
cctgggctct cga                                                    1393

SEQ ID NO: 64          moltype = DNA   length = 2295
FEATURE                Location/Qualifiers
source                 1..2295
                       mol_type = genomic DNA
                       organism = Homo sapiens
SEQUENCE: 64
ctccttcctt cacaccttcc ttcggaaacg tctgctcctg acaaggtcta cttcctgctc  60
tcaggaggcc ttattgtgg aggaagggag gcgtcgcccg tccctggctt ctctgacagc 120
cgtgttccat cccccgcctg tgccccttct cccggacagt gccttctcca gggctcaccc 180
aggagggtgc agcggtggcc cccggggcgg tggtcgtgga ggggggtgtta gctgcagggg 240
tgccctcggt gggtgggagt tggtggcctc tcgctggtgc catgggactc gcatgttcgc 300
cctgcgcccc tcggctcttg agcccacagg ccgggatcct gcctgccagc cgcgtgcgct 360
gccgttttaac ccttgcaggc gcagagcgcg cggcggcggt gacagagaac tttgtttggc 420
tgcccaaata cagcctcctg cagaaggacc ctgcgcccgg ggaaggggag gaatctcttc 480
ccctctgggc gcccgccctc ctcgccatgc cccggcctcc acatccgccc acatctggcc 540
gcagcggggc gccgggggg agggctgag gccgcgtctc tcgccgtccc ctgggcgcgg 600
gccaggcggg gaggagggg gcgctccggt cgtgtgccca ggactgtccc ccagcggcca 660
ctcgggcccc agccccccag gctggcctt acaggcgggg cggagcagcc agtgcagac 720
agggagccg gtgggtggc gggaacctga tccgcccggg aggcgggggc gggggggggg 780
cgcagcgcgc gggagggggc cggcgcccgc cttcctcccc cattcattca gctgagcag 840
ggggcctagg ggctcctccg gcgctagct ctgcactgca ggagcggggg cgcggcgccc 900
cagccagcgc gcagggcccg ggccccgccg gggcgcttc ctccgcctg ccctccgcgc 960
gaccccgctgc ccaccagcca tcatgtcgga ccccgcggtc aacgcgcagc tggatgggat 1020
catttcggac ttcgaaggtg ggtgctgggc tggctgctgc ggccgcggac gtgctggaga 1080
```

```
ggaccctgcg ggtgggcctg gcgcgggacg ggggtgcgct gaggggagac gggagtgcgc    1140
tgaggggaga cgggacccct aatccaggcg ccctcccgct gagagcgccg cgcgcccccg    1200
gccccgtgcc cgcgccgcct acgtggggga ccctgttagg ggcacccgcg tagaccctgc    1260
gcgccctcac aggaccctgt gctcgttctg cgcactgccg cctgggtttc cttccttta    1320
ttgttgtttg tgtttgccaa gcgacagcga cctcctcgga ggctcgcgag gctgcctcgg    1380
aactctccag gacgcacagt ttcactctgg gaaatccatc ggtcccctcc ctttggctct    1440
ccccggcggc tctcgggccc cgcttggacc cggcaacggg ataggggagt cgttcctcac    1500
ctccgactga gtggacagcc gcgtcctgct cgggtggaca ccctcccct cccccacgcc    1560
agtttcgggg ccgccaagtt gtgcagcccg tgggccggga gcaccgaacg gacacagccc    1620
aggtcgtggc agggtctaga gtgggatgtc ccatggcccc catccaggcc tggggatatc    1680
ctcatccgcc tcccagaatc gggccgtggg ggacagaagg ggcctgcgtg cgggcaggga    1740
gagtattttg gctctctcct gtcttcgggg tttacaaagt gtgttgggac ttgcggggct    1800
gctctgtcca agcctgggtc tggcgtccgc gtctctgagc ctgtgagtgc gtgcgctttc    1860
ctgcgtcctc ttgactgccg gtgctggggc tctgcgtcct gcgtccgcgg gagtaaatac    1920
agcaggcgaa ggggaagctc acacaatggt ctccagcgct ctggggcagg gcttctgagg    1980
ggcgggcctg cctctgccgg gacctggagc ccccgcccct cggagaggct cctaggctga    2040
cttgggcaga gccctctggt gggccgggag ggggaaaggc tgtgttgaaa tgagcaaact    2100
gtccaggtgt caggccaagc tgggaggtga ccagcctcag gtcctcccg ctccatgcc     2160
agaaccaggg ctgacatctg ggtgtcctga gcccagctgc ccacacgcc cacctggggt     2220
cagccctatc tgagtggggg aggcggggcc tcctggggga ccagaacttt ggctggacgc    2280
caagcagagt gccag                                                     2295

SEQ ID NO: 65          moltype = DNA  length = 1711
FEATURE                Location/Qualifiers
source                 1..1711
                       mol_type = genomic DNA
                       organism = Homo sapiens
SEQUENCE: 65
tgaggtttgt ttcacagtgg aatgtaaagg gttgcaagga ggtgcatcgg cccctgtgga    60
caggacgcat gactgctaca cacgtgttca ccccaccctc tggcacaggg tgcacataca    120
gtaggggcag aaaatgaacct caagtgctta acacaatttt taaaaaatat atagtcaagt    180
gaaagtatga aaatgagttg aggaaaggcg agtacgtggg tcaaagctgg gtctgaggaa    240
aggctcacat tttgagatcc cgactcaatc catgtccctt aaagggcaca gggtgtctcc    300
acagggccgc ccaaaatctg gtgagagagg gcgtagacgc ctcaccttct gcctctacgg    360
gtcacaaaag cctgggtcac cctggttgcc actgttccta gttcaaagtc ttcttctgtc    420
taatccttca ccctattct cgccttccac tccacctccc gctcagtcag actgcgctac    480
tttgaaccgg accaaaccaa accaaaccaa accaaaccaa accaaaccaa accagaccag acacccctc    540
ccgcggaatc ccagagaggc cgaactggga taaccggatg catttgattt cccacgcac     600
tgagtgcacc tctgcagaaa tgggcgttct ggccctcgcg aggcagtgcg acctgtcacc    660
gcccttcagc cttcccgccc tccaccaagc ccgcgcacgc ccggcccgcg cgtctgtctt    720
tcgacccggc accccggccg gttcccagca gcgcgcatgc gcgcgctccc aggccacttg    780
aagagagagg gcggggccga ggggctgagc ccgcgggggg agggaacagc gttgatcacg    840
tgacgtggtt tcagtgttta cacccgcagc gggcgggggg ttcggcctca gtcaggcgct    900
cagctccgtt tcggtttcac ttccggtgga gggccgcctc tgagcgggcg gcgggccgac    960
ggcgagcgcg ggcggcggcg gtgacgtgagg cgccgctgcc aggggggtg cggcagcgcg     1020
gcggcggcgg cggcggcggc ggcggcggag gcggcggcg cggcggcggc ggcggcggct      1080
gggcctcgag cgcccgcagc ccacctctcg ggggcgggct ccccggcgcta gcagggctga    1140
agagaagatg gaggagctgg tggtggaagt gcgggctcc aatgcgcgtt tctacaaggt     1200
acttggctct agggcaggcc ccatcttcgc ccttccttcc ctcccttttc ttcttggtgt    1260
cggcgggagg caggcccggg gccctcttcc cgagcaccgc gctgggtgc cagggcacgc     1320
tcggcgggat gttgttggga gggaaggact ggacttggaa cctgttggaa gccccctcg     1380
gactccgaga ggcccctagcg cctatcgaaa tgagagacca gcgaggagag ggttctcttt    1440
cggcgccgag ccccgccggg gtgagctggg gatgggcgag ggccggcggc aggtactaga    1500
gccgggcggg aagggccgaa atcggcgcta agtgacggcg atggcttatt ccccctttcc    1560
taaacatcat ctcccagcgg gatccgggcc tgtcgtgtgg gtagttgtgg aggagcgggg    1620
ggcgcttcag ccgggccgcc tcctgcagcg ccaagagggc ttcaggtctc ctttggcttc    1680
tcttttccgg tctagcattg ggacttcgga g                                   1711

SEQ ID NO: 66          moltype = DNA  length = 1404
FEATURE                Location/Qualifiers
source                 1..1404
                       mol_type = genomic DNA
                       organism = Homo sapiens
SEQUENCE: 66
agaagggaat atcagaagca ggacgaaagc caggtcaagt ctctttcctt aggctcccca    60
aagggacaag tactcacctc ccagagacct ggcccagcgg gtcctcatgg cagcaccacc    120
ccctcccggt gcccacgacc attcgtctcc catccgcgt tctccaggat ttccaaagac     180
gcccgtttag atccacaggt acttacctga gtccctctgc ttctccacaa ttcccaaata atatttaata    240
tccccgcctc tctcttttt taaaaaaaaa atttaaacaa ttcccaaata atatttaata    300
ggaaagaaga aggaaaagga gcgcacagga agggcggagg cggcaccggg ggggactgt     360
ccccagagga ggccgctgtg agccggcgac gcgaggctgg gggagtggga ggcaaacccg    420
ctaacctgtc gtcgaatggc cactcccagt tctccgctca cgaggtggaa aaggcagaag    480
gcttgaaggc aaggcgtgag ggagcgccca ggacgctctc cgaggggccg ggccgggtc     540
tgcgctgcag cccgcacgca cctcacttcc cgtcgcggc ggctcggtcg ctgccccctc     600
tcttgggccc cttctggtcg tcgccgtcct cctcctccta gtcctcctcc ttctccttct    660
cctcggctct ccgccccac cgctgatttt cagcgcttc tgcccgcccc tctcccggcc     720
ctcgctgctt tccctgcagc gtgctcctcg tccctatctc ggatgggat ggggcagggg     780
gcgcggggtg agccatcaac tccagccgcc tgcctgcccg cgcaaggcgg gaaagtgggg    840
gcgcttttgc gcctcacgtt aagtttaggg tcacgagcac tcttgtggag atcggagcg     900
```

```
gttgggctag ggatgatgcc tcttcctctt tccccttccc ctcccttctt gtccccgcct  960
ttcctctggg tcctcccggg gaccaccccc taccccctcgt cagagtcgcc ctggagagc  1020
cgagggcctg agggtcgacc accaagggca gagcctatcc cttggggagc tgctggagga  1080
gacaggcagc gccgggaggt ggctcacacc gcaccgccga gagcgctttg ccctcgcatc  1140
gctgaaattt aatcacggtc acaggttaca acgttaggtc tcgctttagt tcaaatatct  1200
tcaaggtttt cgtttgctct taatctagga agagccggaa agggtcctga gggtgaaagg  1260
gagactacta aggaagagtc acaggttgag gaggcaggaa aaggctcagc aaatcctctt  1320
tccacgccac tatcaccatt ttcctttcca ccaatcagcg cctgccagac gctgattttc  1380
ccatcagtgg aacaaggaat aaat                                        1404

SEQ ID NO: 67           moltype = DNA  length = 1756
FEATURE                 Location/Qualifiers
source                  1..1756
                        mol_type = genomic DNA
                        organism = Homo sapiens
SEQUENCE: 67
caaaggctgt aacaacctgg aacgcaaatt cgttaaatta tgatacaata aggccaacct   60
cgaggatcct cggtggacta ctagcgcact tcctacaat tagaaagtga aaaactgggt   120
cagccctaga gtcacgcaat aatgctgcgt cacgaaactg cgcattccaa gagaaacttt   180
tctcaggccc agaattaagt cggagggatc cgccgcgcag ctcaatccct aggaagcatg   240
aaagaatgta ttgtaaagag taaaatcacg cgcaatccat cccaatataa ccgcagttgt   300
tcgtggggcct tcttgcagag aaaggctgcc caaccttgac ggggccatgg gcgctgcggg  360
agggcaaaag accacagaga tctgcgaagc caaagtaaac aacggggttg gggcggcgag  420
aatgatcaat agcgatgctc cgaaaggact ccgcgatagg aatcgagcgg aaggattcc   480
ctccatccta acagtccatg ggttaagagg ccgaagcttc cctaaatacc acactcccgc  540
gagagaaggg actgagaaca acttctcaaa ctattctctc tcgaaatcgt tcccttcctc  600
gaaaattcca tctctgagac tcggatgagg tccccacccc ctccacccctt gtcccgtgac  660
cgtcgcccgc tcagcctccc agccgagtcc gcggggcctg gggcgcccac cccgcccacc  720
caagggaccg cgcaggggtg aactccccccg cgccccacct gcgccttcca gacctcgggc  780
gcccgcgcgt tgcctcgaga gctccctgcg cggccgccgc ggcacggacc agctcccact  840
cccttacact gggcgccgct gcgctcgccg ggggccggtc ccgaggttcc caaggcctcg  900
cgcgcgcgct tgccgtggca accaagacgt tccacgacgc gcgctctcga acgcttcgcg  960
tcacgcggcc gcgcggcccc gcccgtcggc ctcgctcccg ccacagagcc cgcagcacgc  1020
cgccgccgca gcctaggtca cgtgagtacc cacgcgcgcg tcttgccagc ggattcatca  1080
ccggcctgct cagactaggt tctgcccact ctgaccttct aaatggtacg tgggaggacg  1140
tccgtccccct tcggacccaa gagtcaccgt aacactctag aaggggagaa aaggagcgag  1200
ggcggcaggc gacagagaac ctcgcgagtc agcggccccg cgcagacccc ccaggcacg  1260
gtcccctgcg gccacgtcgg ctgctcggcg cctgcgcaat ctctttctct ccagcgaaac  1320
cgaggcctcc ggagagccta gtagagagtg tgggcagtga gcgcttgtag ccgctagagg  1380
gagcgctggg cacagtgcac gagagacaat aaaggctgat tatcccctca atgtctctgc  1440
agcctgagct ttgtgacttc tgtatccaga gcacagttaa tttccaaaag cccgcctgca  1500
ccacgtgttt taagtcttgg tgtgtgtgta aagtctatat cactatcata aaactgttag  1560
ttcctgattc cggatacaa agagtaaaat caagatgaac atactttacc cttcttgaca  1620
agtgtttttta aattagtaaa atattgtaga tgcagactc ttcaataggg ctgccttagg  1680
gaaaaaaaaa cagaaaaaag aaaaagcagt atgtacttgc ccggagcatt tagaaccagt  1740
tttgttgttg ttgtgt                                                 1756

SEQ ID NO: 68           moltype = DNA  length = 2161
FEATURE                 Location/Qualifiers
source                  1..2161
                        mol_type = genomic DNA
                        organism = Homo sapiens
SEQUENCE: 68
agaggtcgtg gcactgagat gggtctggca gatcccagcg tccaggccca gcccctatag   60
tgtcagctcc ctcctctggg gaccccctttg ctttgtgccu tctgggtccc agcacatcc   120
aggcctgcag ggaggggggag aggaagagac tgactcactg gccaggtccc ccaggggctg  180
gagaggctgg agaggcagga gctggatcag atctgaatcc agaggctctc ggaggaagag  240
ctcagggtga gctgcgcccc catcccctgc ccctcctctc ctgctccttc tcccttccat  300
ggtcccagcc agcaagcacc tggggtagag gggacaaacc caggtggctg tgttccagtc  360
ctggctgcag gtctgaatgg ctttctgggg tggctggcca tgctcccctga gagcccagct  420
gtggcgatgt ctgagcaggt aggtggggga gcacctagga agcagggtg tcaggcagag  480
cacaaggaga gagggtgtcc aagtcagttt caggacctgg ctgagaggag ggggctcctc  540
acgggcaccg cctctggcaa gcacaggac aagggcaagg acggcatggc cagaggtccc  600
tgggaggctc ttcccctctc ttcttcctag cagctccccg tcactcttcc caggggaccct  660
gtcactttcc tttagcgtgt ggcagctcct tggcgtccct cccgtgcctt caggttgctt  720
ctgcgccggg cctgccgctg ggcgccccta tctctgcctg cccctcctc ctgctccct  780
cgccctgccc ccttggagca attccccacc gagcctccct tccaggcag tcgaggtccc  840
tccctacctc tgcccgcgc tctgggaggc tccttgttcc gcgaccacaa agcccctttg  900
atcctctgct cggctctgag ccatgtgacc cggtgggcgg gcgcggctc tcggcgctgc  960
cagcgcagcc cgacgttccg ctgctggggt gagtcctgct cctttgttct tcccagcctt  1020
gcaccactgg ctcgggggct ctcaggtggc gcggccgcga gcggaccct gatgccatg  1080
gtggcggtgc cggagccac gctgtccctg gccccggcc cgaggccggc aggaccgagc  1140
ggggtccccca ggagagggt ggcggggagc tcgatctcca cgcggggacc agattttcgg  1200
cctcaaaata gaagaatagg gctttgtgtg tcacagcta tctcttttgta aatatttggc  1260
caactaagct gagtggctaa gttcctcctgc tgcccggagc ttcttggaac atgtttcctt  1320
ttcgcaaggg gtttccctgg cttccaggag ggcaggaag aaattcgaat ggccaccgc  1380
tttctctaaa atcactccgc tcaagttatc acccctctgg gctcccgaag accggctggc  1440
tggaggctga agatagtctc aatgctcgaa atgccgtaac cgaagctccc gcggcgccg  1500
gcactgggat ccagggagct gctgctacag cgcagctctg gattcctgga tgtgttggat  1560
```

-continued

```
atgtgcaggg cgttcctggg aggagcgggg agggagggtg ctgctggcgg ggctggtctg   1620
cgtgtgcttt gcttctctac aatggcatgc tgcgtgtcgg ccatgcagag gcatgtcagt   1680
gagcagggc tgagggatct ccctaacgga cctgctttca gagggtcttt tcatgctggg    1740
agaaccccag agactaaatc atgcagccaa cggggtggtc cccggcctca aagcaggag    1800
gggcgaggag ctttgtaggc aatgccatct gctcctgaaa cgccgtccca gtgactctgg   1860
ggactgactc agcctccagc ctgctgcact tcatccctgg cccctctctc tttgcttttt   1920
catgtgaaat ctgctgtgtt ttggtcagag gtttggggaa cagctctctg ctcatctaag   1980
ataagtttgt aattcctttc ctggagaaaa atatgccacc cggaagcagg ttgagcagtg   2040
gttttctggc aggtctgttc ggggctgtgg agacagcacc tgctggatca ggatggagtt   2100
ggaatttggt ttggatccca catgagaaaa cccgttggaa gaggaggaag cagaaaaagg   2160
c                                                                  2161
```

SEQ ID NO: 69           moltype = DNA   length = 26
FEATURE                 Location/Qualifiers
misc_feature            1..26
                        note = PS421 Loop oligonucleotide with 5' phosphate
source                  1..26
                        mol_type = other DNA
                        organism = synthetic construct
SEQUENCE: 69
taaagcactg agatttttct cagtgc                                        26

SEQ ID NO: 70           moltype = DNA   length = 58
FEATURE                 Location/Qualifiers
misc_feature            1..58
                        note = Capture Oligonucleotide for FMR1 Target
source                  1..58
                        mol_type = other DNA
                        organism = synthetic construct
SEQUENCE: 70
aaccctttac attccactgt gaaacaaacc tcaactttga ctcagctaac actgagtc     58

SEQ ID NO: 71           moltype = DNA   length = 58
FEATURE                 Location/Qualifiers
misc_feature            1..58
                        note = Capture Oligonucleotide for CNRIP1 Target
source                  1..58
                        mol_type = other DNA
                        organism = synthetic construct
SEQUENCE: 71
ttcccttttgg cttgtattcc tccattctcg cttccctcga ctcagctaac actgagtc    58

SEQ ID NO: 72           moltype = DNA   length = 58
FEATURE                 Location/Qualifiers
misc_feature            1..58
                        note = Capture Oligonucleotide for MAL Target
source                  1..58
                        mol_type = other DNA
                        organism = synthetic construct
SEQUENCE: 72
ggttctttgc ctgcctgttg actgccggtg tttcatgtga ctcagctaac actgagtc     58

SEQ ID NO: 73           moltype = DNA   length = 58
FEATURE                 Location/Qualifiers
misc_feature            1..58
                        note = Capture Oligonucleotide for HTT Target
source                  1..58
                        mol_type = other DNA
                        organism = synthetic construct
SEQUENCE: 73
gtttctttat gggagtgcac ccctgctctg accttccgga ctcagctaac actgagtc     58

SEQ ID NO: 74           moltype = DNA   length = 58
FEATURE                 Location/Qualifiers
misc_feature            1..58
                        note = Capture Oligonucleotide for SNCA Target
source                  1..58
                        mol_type = other DNA
                        organism = synthetic construct
SEQUENCE: 74
ctggctttcg tcctgcttct gatattccct tctccacaga ctcagctaac actgagtc     58

SEQ ID NO: 75           moltype = DNA   length = 58
FEATURE                 Location/Qualifiers
misc_feature            1..58
                        note = Capture Oligonucleotide for EGFR Target
source                  1..58
                        mol_type = other DNA
                        organism = synthetic construct

```
SEQUENCE: 75
gtgcttttag agaggctaag tgtcccactg ccctgtaga ctcagctaac actgagtc    58

SEQ ID NO: 76           moltype = DNA   length = 58
FEATURE                 Location/Qualifiers
misc_feature            1..58
                        note = Capture Oligonucleotide for C9orf72 Target
source                  1..58
                        mol_type = other DNA
                        organism = synthetic construct
SEQUENCE: 76
ttgttttac cgtaagacac tgttaagtgc attcaaaaga ctcagctaac actgagtc    58

SEQ ID NO: 77           moltype = DNA   length = 58
FEATURE                 Location/Qualifiers
misc_feature            1..58
                        note = Capture Oligonucleotide for INA Target
source                  1..58
                        mol_type = other DNA
                        organism = synthetic construct
SEQUENCE: 77
gtgttttcc agttacagtg aggacctgca gagcgagcga ctcagctaac actgagtc    58

SEQ ID NO: 78           moltype = DNA   length = 58
FEATURE                 Location/Qualifiers
misc_feature            1..58
                        note = Capture Oligonucleotide for SPG20 Target
source                  1..58
                        mol_type = other DNA
                        organism = synthetic construct
SEQUENCE: 78
acgaatttgc gttccaggtt gttacagcct ttgaaataga ctcagctaac actgagtc    58

SEQ ID NO: 79           moltype = DNA   length = 58
FEATURE                 Location/Qualifiers
misc_feature            1..58
                        note = Capture Oligonucleotide for FBN1 Target
source                  1..58
                        mol_type = other DNA
                        organism = synthetic construct
SEQUENCE: 79
agagatttct gccccaaagg agaggacgtg gttaaatgga ctcagctaac actgagtc    58

SEQ ID NO: 80           moltype = DNA   length = 58
FEATURE                 Location/Qualifiers
misc_feature            1..58
                        note = Capture Oligonucleotide for NDRG4.2 Target
source                  1..58
                        mol_type = other DNA
                        organism = synthetic construct
SEQUENCE: 80
ttccatttcc tgcagatatg tcacccaccc cccaaccaga ctcagctaac actgagtc    58

SEQ ID NO: 81           moltype = DNA   length = 58
FEATURE                 Location/Qualifiers
misc_feature            1..58
                        note = Capture Oligonucleotide for SEPT9.1 Target
source                  1..58
                        mol_type = other DNA
                        organism = synthetic construct
SEQUENCE: 81
agacgtttcc gaaggaaggt gtgaaggaag gagctaggga ctcagctaac actgagtc    58

SEQ ID NO: 82           moltype = DNA   length = 58
FEATURE                 Location/Qualifiers
misc_feature            1..58
                        note = Capture Oligonucleotide for SEPT9.2 Target
source                  1..58
                        mol_type = other DNA
                        organism = synthetic construct
SEQUENCE: 82
ctgggtttgt ccctctacc ccaggtgctt gctggctgga ctcagctaac actgagtc    58

SEQ ID NO: 83           moltype = DNA   length = 58
FEATURE                 Location/Qualifiers
misc_feature            1..58
                        note = Capture Oligonucleotide for DMPK Target
source                  1..58
                        mol_type = other DNA
```

```
                             organism = synthetic construct
SEQUENCE: 83
aaagctttct tgtgcatgac gccctgctct ggggagcgga ctcagctaac actgagtc      58

SEQ ID NO: 84           moltype = DNA  length = 26
FEATURE                 Location/Qualifiers
misc_feature            1..26
                        note = Targeted sequence
source                  1..26
                        mol_type = other DNA
                        organism = synthetic construct
SEQUENCE: 84
cctttgcttg cgtttagtat cccaaa                                         26

SEQ ID NO: 85           moltype = DNA  length = 22
FEATURE                 Location/Qualifiers
misc_feature            1..22
                        note = Targeted sequence
source                  1..22
                        mol_type = other DNA
                        organism = synthetic construct
SEQUENCE: 85
cctttgcttg cgtttagtat cc                                             22

SEQ ID NO: 86           moltype = DNA  length = 94
FEATURE                 Location/Qualifiers
misc_feature            1..94
                        note = Oligonucleotide probe
source                  1..94
                        mol_type = other DNA
                        organism = synthetic construct
SEQUENCE: 86
tttgggatac taaacgcaag caaaggacct gagtacggtg atacacctag atagggtcag    60
tgctgcaacc cacttcctaa tctgtcatct tctg                                94

SEQ ID NO: 87           moltype = DNA  length = 24
FEATURE                 Location/Qualifiers
misc_feature            1..24
                        note = Region in oligonucleotide probe
source                  1..24
                        mol_type = other DNA
                        organism = synthetic construct
SEQUENCE: 87
ggatactaaa cgcaagcaaa ggac                                           24

SEQ ID NO: 88           moltype = DNA  length = 15
FEATURE                 Location/Qualifiers
misc_feature            1..15
                        note = 5' flap structure
source                  1..15
                        mol_type = other DNA
                        organism = synthetic construct
SEQUENCE: 88
tttgggatac taaac                                                     15

SEQ ID NO: 89           moltype = DNA  length = 24
FEATURE                 Location/Qualifiers
misc_feature            1..24
                        note = Universal sequence on which the single stranded
                         oligonucleotidewill bind
source                  1..24
                        mol_type = other DNA
                        organism = synthetic construct
SEQUENCE: 89
ctgagtacgg tgatacacct agat                                           24

SEQ ID NO: 90           moltype = DNA  length = 40
FEATURE                 Location/Qualifiers
misc_feature            1..40
                        note = Sequence required for attachment to the surface
source                  1..40
                        mol_type = other DNA
                        organism = synthetic construct
SEQUENCE: 90
ggtcagtgct gcaacccact tcctaatctg tcatcttctg                          40

SEQ ID NO: 91           moltype = DNA  length = 60
FEATURE                 Location/Qualifiers
misc_feature            1..60
```

```
                            note = Region within PCR fragment of SEPT9.2 target
source                      1..60
                            mol_type = other DNA
                            organism = synthetic construct
SEQUENCE: 91
agcaagcacc tggggtagag gggacaaacc caggtggctg tgttccagcc ctggctgcag    60

SEQ ID NO: 92               moltype = DNA  length = 24
FEATURE                     Location/Qualifiers
misc_feature                1..24
                            note = Region within PCR fragment of SEPT9.2 target
source                      1..24
                            mol_type = other DNA
                            organism = synthetic construct
SEQUENCE: 92
agcaagcacc tggggtagag ggga                                           24

SEQ ID NO: 93               moltype = DNA  length = 26
FEATURE                     Location/Qualifiers
misc_feature                1..26
                            note = TaqMan probe specific to FMR1 (5' FAM and 3' MGB)
source                      1..26
                            mol_type = other DNA
                            organism = synthetic construct
SEQUENCE: 93
aagagggctt caggtctcct ttggct                                         26

SEQ ID NO: 94               moltype = DNA  length = 19
FEATURE                     Location/Qualifiers
misc_feature                1..19
                            note = qPCR oligonucleotide A for FMR1
source                      1..19
                            mol_type = other DNA
                            organism = synthetic construct
SEQUENCE: 94
tgtcgtgtgg gtagttgtg                                                 19

SEQ ID NO: 95               moltype = DNA  length = 20
FEATURE                     Location/Qualifiers
misc_feature                1..20
                            note = qPCR oligonucleotide B for FMR1
source                      1..20
                            mol_type = other DNA
                            organism = synthetic construct
SEQUENCE: 95
ctccgaagtc ccaatgctag                                                20

SEQ ID NO: 96               moltype = DNA  length = 17
FEATURE                     Location/Qualifiers
misc_feature                1..17
                            note = qPCR oligonucleotide C for FMR1
source                      1..17
                            mol_type = other DNA
                            organism = synthetic construct
SEQUENCE: 96
gcccagaaca gtggagc                                                   17

SEQ ID NO: 97               moltype = DNA  length = 26
FEATURE                     Location/Qualifiers
misc_feature                1..26
                            note = qPCR oligonucleotide D for FMR1
source                      1..26
                            mol_type = other DNA
                            organism = synthetic construct
SEQUENCE: 97
gtattagctg aggattaggt cacagg                                         26

SEQ ID NO: 98               moltype = DNA  length = 59
FEATURE                     Location/Qualifiers
misc_feature                1..59
                            note = Target specific adaptor for FMR1 crRNA#2
source                      1..59
                            mol_type = other DNA
                            organism = synthetic construct
SEQUENCE: 98
ctagcattgg gacttcggag cctgtgacct aatcctcagc taatacagct agactacgt     59

SEQ ID NO: 99               moltype = DNA  length = 59
FEATURE                     Location/Qualifiers
```

```
misc_feature            1..59
                        note = Target specific adaptor for FMR1 crRNA#2 where n is
                         an abasicsite modification, specifically tetrahydrofuran
                         (THF)
misc_feature            43
                        note = n is a, c, g, or t
source                  1..59
                        mol_type = other DNA
                        organism = synthetic construct
SEQUENCE: 99
ctagcattgg gacttcggag cctgtgacct aatcctcagc tantacagct agactacgt    59

SEQ ID NO: 100          moltype = DNA  length = 75
FEATURE                 Location/Qualifiers
misc_feature            1..75
                        note = Target specific adaptor for FMR1 crRNA#1
source                  1..75
                        mol_type = other DNA
                        organism = synthetic construct
SEQUENCE: 100
ccactgtgaa acaaacctca ggcctaggga gccgcacctt gttctgcaac ccacttccta   60
atctgtcatc ttctg                                                    75

SEQ ID NO: 101          moltype = DNA  length = 43
FEATURE                 Location/Qualifiers
misc_feature            1..43
                        note = Oligonucleotide to generate a Y-shape for FMR1
source                  1..43
                        mol_type = other DNA
                        organism = synthetic construct
SEQUENCE: 101
tgccggatta tgcggataag tacaaggtgc ggctccctag gcc                     43

SEQ ID NO: 102          moltype = DNA  length = 26
FEATURE                 Location/Qualifiers
misc_feature            1..26
                        note = Specific loop adaptor on the abasic site for FMR1
                         (5' phosphate)
source                  1..26
                        mol_type = other DNA
                        organism = synthetic construct
SEQUENCE: 102
atacgcactg agatttttct cagtgc                                        26

SEQ ID NO: 103          moltype = DNA  length = 20
FEATURE                 Location/Qualifiers
misc_feature            1..20
                        note = 5' biotin linker
source                  1..20
                        mol_type = other DNA
                        organism = synthetic construct
SEQUENCE: 103
ccatgattac gccaagctcg                                               20

SEQ ID NO: 104          moltype = DNA  length = 40
FEATURE                 Location/Qualifiers
misc_feature            1..40
                        note = Complementary sequence to the linker and the hairpin
                         molecule
source                  1..40
                        mol_type = other DNA
                        organism = synthetic construct
SEQUENCE: 104
cttatccgca taatccggca cgagcttggc gtaatcatgg                         40
```

METHOD OF NUCLEIC ACID ENRICHMENT USING SITE-SPECIFIC NUCLEASES FOLLOWED BY CAPTURE

CROSS-REFERENCE TO RELATED APPLICATIONS

This application is a continuation of U.S. application Ser. No. 17/312,998 filed Jun. 11, 2021, now U.S. Pat. 11,473, 124, which is the U.S. Natl. Stage of International Appln. PCT/EP2019/084983, filed on Dec. 12, 2019, which itself claims the benefit of European Appln. EP 18306679.4 filed on Dec. 12, 2018, the contents of each of which are incorporated herein by reference in their entireties for all purposes.

REFERENCE TO SEQUENCE LISTING SUBMITTED ELECTRONICALLY

The instant application contains a Sequence Listing which has been submitted electronically in ST.26 format and is hereby incorporated by reference in its entirety. Said ST.26 copy, created on Aug. 16, 2022, is named B381791US_D39002.xml and is 167,490 bytes in size.

INTRODUCTION

The present invention relates to methods of nucleic acid isolation and enrichment. Indeed, isolation and enrichment of target nucleic acids represent critical first steps in the study of nucleic acids, influencing both nucleic acid quantity and quality, which in turn directly impacts the quality of data obtained in downstream applications (e.g. sensitivity, coverage, robustness, and reproducibility). This is particularly important in applications in which only certain target nucleic acids are analysed from a more complex mixture, or in cases where a low amount of target nucleic acid is present. As an example, the human "exome" (regions coding for proteins) represents only about 1% of the total genome, yet harbours 85% of DNA variations known to be associated with genetic disease. Thus, isolation and enrichment are of particular interest in clinical applications associated with the exome, such as diagnostics and genetic risk assessment.

While whole-genome analyses may be used even when few nucleic acid targets are of interest, it is often not feasible to sequence an entire genome, due to technical, economical, and/or time constraints. Furthermore, whole-genome sequencing requires vastly increased computing power and storage to analyse the large amount of data generated. Nucleic acid isolation is therefore desirable in order to limit analyses to a specific subset of nucleic acid molecules.

To date, the main approaches used to isolate a subset of specific nucleic acid fragments are based on hybrid capture and/or targeted amplification techniques (see, for example, Mertes et al., *Brief Funct Genomics*, 2011, 10 (6): 374-86 and WO 2016/014409). However, current methods of hybrid capture have low enrichment efficiency, with 15-25% of capture being off-target (Garcia-Garcia, *Sci Rep.*, 2016, 6:20948), and generally requires at least two rounds of selection. Nucleic acids also are denatured prior to capture, thereby removing any information encoded via the complementarity of the two strands or on the complementary strand itself. When using hybrid capture, amplification is also often required to increase the amount of nucleic acid material. However, amplification generates bias depending on the AT:GC ratio and the secondary structure of the fragments being amplified and becomes less efficient as the length of the amplified fragments increases. Furthermore, the number of target regions that can be amplified in a multiplexed fashion is limited due to primer cross-reactivity. In addition, all chemical modifications (e.g. base modifications) present in the original sequence are lost during the amplification process. Finally, amplification may introduce artifacts (i.e. unwanted or non-specific nucleic acid sequences) or errors in the nucleic acid.

Given these limitations, there is a need for new methods of isolation and/or enrichment of target nucleic acids, in particular, methods of nucleic acid isolation and enrichment that conserve the characteristics of the original nucleic acid molecule of interest (e.g. chemical modifications, such as base modifications, and nucleic acid sequence information, such as mismatches or SNPs), that do not require multiple rounds of selection, and that are compatible with downstream analysis technologies, such as nucleic acid sequencing.

DETAILED DESCRIPTION OF THE INVENTION

Before describing the present invention in detail, it is to be understood that the invention is not limited to particularly exemplified aspects and may, of course, vary. It is also to be understood that the terminology used herein is for the purpose of describing particular embodiments of the invention only, and is not intended to be limiting.

All publications, patents and patent applications cited herein, whether supra or infra, are hereby incorporated by reference in their entirety. Furthermore, the practice of the invention employs, unless other otherwise indicated, conventional techniques of protein chemistry, molecular biology, microbiology, recombinant DNA technology, and pharmacology, which are within the skill of the art. Such techniques are explained fully in the literature. See, for example, Ausubel et al., Current Protocols in Molecular Biology, Eds., John Wiley & Sons, Inc. New York, 1995, Remington's Pharmaceutical Sciences, 17th ed., Mack Publishing Co., Easton, Pa., 1985, and Sambrook et al., Molecular cloning: A laboratory manual 2nd edition, Cold Spring Harbor Laboratory Press-Cold Spring Harbor, NY, USA, 1989.

In the claims which follow and in the preceding description, the words "comprise," "comprises," "comprising," and other variations are used in an inclusive sense, i.e. to specify the presence of the stated features but not to preclude the presence or addition of further features in various embodiments of the invention, except where the context requires otherwise due to express language or necessary implication. Furthermore, the terms "a," "an," and "the," as used herein include plural forms unless the content of the present application clearly dictates otherwise. As an example, "a target region" therefore also includes two or more target regions.

In a first aspect, the present invention is directed to a novel method for the isolation of nucleic acid target regions from a population of nucleic acid molecules, comprising contacting said population with a Class 2 Type V Cas protein-gRNA complex, followed by an enzyme having single-stranded 3' to 5' exonuclease activity. Indeed, the inventors have surprisingly found that these steps generate nucleic acid molecules having 5' single-stranded overhangs of at least 9 nucleotides in length. As a result, capture methods such as hybrid capture may then be advantageously performed by hybridizing oligonucleotides to said overhang, thereby specifically enriching the adjacent target region. Advantageously, only target regions of interest are isolated as Class 2 Type V Cas protein-gRNA complexes target and cleave at highly specific sites, that may occur only once in an entire genome. In notable contrast, restriction enzymes recognize and cleave shorter sites that are therefore present multiple times within a given sequence, and furthermore generate relatively short overhangs (e.g. 3 bases).

The present method is highly advantageous over current methods as all characteristics of the target nucleic acid (e.g. chemical modifications, mismatches) are conserved, as the original nucleic acid molecule remains intact in all steps of the present method. In contrast to existing methods of hybrid capture, the nucleic acids isolated via the present method need not be denatured. As amplification steps are unnecessary in the present method, bias is also reduced. In addition, multiplex assays can be easily designed with no risk of primer interactions or cross-recognition. Small sample sizes and samples with low levels of target nucleic acid may also be used in the present method without target amplification, as the efficiency of nucleic acid target isolation is high and with good specificity. Advantageously, isolation is sufficient when only a single round is performed. Furthermore, as all steps can be performed in the same container, this method is simple, with reduced possibility for error, when compared to the methods of the prior art. Sample loss is further reduced due to the absence of material transfer between containers. Finally, the method of the invention is advantageous over current methods as it is quick and inexpensive, may be performed directly on samples, has few processing steps, and is compatible with existing downstream nucleic acid analysis platforms, including "third-generation" sequencing technologies, wherein single nucleic acid molecules are analysed within micro-structures, such as nanopores, zero-mode wave guides, or microwells. Notably, the present method provides isolated specific nucleic acid target regions that may comprise specific single-stranded nucleic acid overhangs on either or both ends, onto which various adaptors or linkers can be specifically ligated, providing flexibility for use of target regions in a wide variety of downstream analyses and applications.

More specifically, said method of isolating a nucleic acid target region from a population of nucleic acid molecules comprises the steps of:
a) contacting said population of nucleic acid molecules with a Class 2 Type V Cas protein-gRNA complex, wherein the gRNA comprises a guide segment that is complementary to a first site adjacent to said target region, thereby forming a Class 2 Type V Cas protein-gRNA-nucleic acid complex,
b) contacting the population of nucleic acid molecules comprising said Class 2 Type V Cas protein-gRNA-nucleic acid complex with at least one enzyme having single-strand 3' to 5' exonuclease activity, thereby forming a 5' single-stranded overhang in said first site,
c) removing the Class 2 Type V Cas protein-gRNA complex from the population of step b),
d) contacting the population of step c) with an oligonucleotide probe, said probe comprising a sequence that is at least partially complementary to said overhang, thereby forming a duplex between said probe and said overhang, and
e) isolating said duplex from the population of nucleic acid molecules of step d), thereby isolating said nucleic acid target region.

In the method described above, the steps are performed sequentially in the order provided, with step a) performed first followed by step b) then step c) then step d). Alternatively, step a and step b) may be performed simultaneously, in particular when the target nucleic acid regions or molecules are double-stranded.

In some cases, additional steps may be included in the method. As a non-limiting example, an additional step of fragmenting one or more nucleic acid molecules to obtain a population of nucleic acid molecules may be included in the above method at any stage, for example prior to step a), simultaneously to step a), between steps a) and b), or simultaneously to step b), step c) or step e). As a non-limiting example, an additional step of incubation may be further comprised before, during, or after any steps of the above method. As a non-limiting example, a step of storage may be further comprised after step c), after step d), or after step e). These optional additional steps are further detailed below.

The term "contacting" as used herein refers to placing of two or more molecules and/or products in a same solution such that said molecules and/or products may interact with one another. Contacting a population of nucleic acid molecules with a Class 2 Type V Cas protein-gRNA complex, for example, allows for the interaction of these molecules and the formation of complexes in which the Class 2 Type V Cas protein-gRNA complex has bound to the nucleic acid molecule at a specific site. Similarly, contacting a population of nucleic acid molecules with an oligonucleotide probe will result in the hybridization of at least single-stranded regions of the probe with single-stranded regions comprised within the population of nucleic acid molecules that are at least partially complementary. In step d) of the method provided herein, this corresponds more specifically to the hybridization of a single-stranded region of said probe to a 5' overhang that is at least partially complementary. As a further example, "contacting" a molecule or product with an enzyme, such as an exonuclease, will result in an enzymatic reaction when said molecule or product is or comprises the substrate of said enzyme. For example, contacting a population of nucleic acid molecules with an enzyme having single-strand 3' to 5' exonuclease activity will result in the interaction of these molecules, and the degradation of the enzyme substrate (e.g. single stranded nucleic acid molecules or regions having a 3' free end) that is accessible to said enzyme.

The terms "isolation" or "isolating" as used herein refer to an increase in the proportion of one or more nucleic acid target regions with respect to one or more other regions or molecules in a sample. As a non-limiting example, these other molecules may comprise proteins, lipids, carbohydrates, metabolites, nucleic acids, or combinations thereof. As a non-limiting example, these other regions may correspond to nucleic acid regions present on the same molecule as said target region but that are not comprised in the target region (i.e. "non-target regions"). The "isolation" of the target nucleic acid region, as used herein, may refer more specifically to an increase in the proportion of the one or more target nucleic acid regions in a sample by at least 2-fold (e.g. 2, 3, 4, 5, 10, 20, 30, 40, 50, 60, 70, 80, 90, 100, 250, 500, 750, 1000, or 10,000-fold or more), as compared to the one or more other molecules in a sample, or as compared to the total number of molecules in the initial sample (i.e. prior to performing the method of isolating a target region of the invention). Isolation of the target nucleic acid region may also refer to an increase in the proportion of the target nucleic acid region in the sample by at least 5% (e.g. 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100%) when compared to the level of the one or more other molecules in a sample. When the proportion of the target nucleic acid region is 100%, no other molecules are comprised in the sample. The term "enrichment" as used herein refers more specifically to the isolation of one or more target nucleic acid regions with respect to the other nucleic acid molecules in the sample. As an example, enrichment of the target region refers to an increase in the proportion of the isolated target region as compared to the amount of total initial nucleic acid, wherein the proportion of the isolated target region is increased by at least 10%, 20%, 30%, 40%, 50%, 60%, 65%, 70%, 75%, 80%, 85%, 90%, 95%, 96%, 97%, 98%, 99% or 100%. According to a preferred embodiment, the proportion of the isolated target region, as compared to the amount of total initial nucleic acid is increased by at least 10%, more preferably at least 20%, at least 30%, at least 40%, at least 50%, at least 60%, at least 65%, at least 70%, at least 75%, at least 80%, at least 85%, at least 90%, at least 95%, at least 96%, at least 97%, at least 98%, even more preferably at least 99% or 100%.

According to one embodiment, the isolated nucleic acid target region is enriched by at least 10-fold, at least 20-fold, at least 50-fold, at least 100-fold, at least 250-fold, at least 500-fold, at least 750-fold, preferably by at least 1000-fold, at least 10,000-fold, at least 100,000-fold, even more preferably by at least 1,000,000-fold, at least 2,000,000-fold, or at least 3,000,000-fold. As a particular example, the 100% enrichment of a single 1 kb fragment from a population of nucleic acid molecules equivalent to the human genome of approximately 3.2 billion bp represents a 3,000,000-fold increase.

According to an alternative embodiment, the isolated target region is substantially pure. By "substantially pure" is meant that the isolated target region comprises at least 99%, preferably at least 99.5%, of the total nucleic acid in the sample following isolation of the target region according to the method of the present invention.

According to a preferred embodiment, the target region comprises less than 10% of the total nucleic acid in the initial sample (e.g. prior to isolating the target region according to the present method), preferably less than 5%, more preferably less than 2%, less than 0.05%, less than 0.02%, even more preferably less than 0.01%, less than 0.005%, less than 0.001%, less than 0.0005%, less than 0.0001%, less than 0.00005%, less than 0.00001%, or less than 0.0000005%. The skilled person will realize that the amount or percent of the target region within the total nucleic acid of a sample will vary depending on the number of target regions to be isolated and the length of the target regions(s) to be isolated. As a non-limiting example, a 1 kb target region of interest within the human genome of approximately 3.2 billion bp represents less than 0.0000005% of the total genome.

The nucleic acid target region is isolated from a population of nucleic acid molecules, said population of nucleic acid molecules being generally comprised in a sample. The term "sample" as used herein refers to any material or substance comprising a population of nucleic acid molecules, including, for example, biological, environmental, or synthetic samples. A "biological sample" may be any sample which may contain a biological organism, such as, for example, bacteria, viruses, archaea, animals, plants, and/or fungi. A "biological sample" according to the invention also refers to a sample which may be obtained from a biological organism, such as a cellular extract obtained, for example, from bacteria, viruses, archaea, plants, fungi, animals, and/or other eukaryotes. Molecules of the nucleic acid of interest can be obtained directly from an organism or from a biological sample obtained from an organism, e.g., from blood, urine, cerebrospinal fluid, seminal fluid, saliva, sputum, stool and tissue (such as cell tissue or plant tissue). Any cell, tissue or body fluid may be used as a source of nucleic acid in the context of the invention. Nucleic acid molecules may also be recovered or purified from cultured cells, such as a primary cell culture or a cell line. The cells or tissues from which nucleic acids of interest are obtained can be infected with a virus or other intracellular pathogen. A sample can also be total nucleic acids extracted from a biological specimen. An "environmental sample" may be any sample comprising nucleic acid that is not taken directly from a biological organism (e.g. soil, seawater, air, etc.), and may comprise nucleic acids that are no longer present within a biological organism. A "synthetic sample" comprises artificial or engineered nucleic acids. Alternatively, the sample may be from any source suspected of comprising a target nucleic acid region.

In certain embodiments, the method of the invention may comprise one or more steps of treating the sample to facilitate the isolation of the nucleic acid comprising the target region according to the method of the present invention. As a non-limiting example, the sample may be concentrated, diluted, or disrupted (e.g. by mechanical or enzymatic lysis). Nucleic acids may be completely or partially purified prior to step a) of the present method, or may be in non-purified form.

The terms "nucleic acid," "nucleic acid region," and "nucleic acid molecule" as used herein refer to a polymer of nucleotide monomers including deoxyribonucleotides (DNA), ribonucleotides (RNA), or analogs thereof, as well as combinations thereof (e.g. DNA/RNA chimeras). The deoxyribonucleotide and ribonucleotide monomers described herein refer to monomeric units which comprise a triphosphate group, the adenine ("A"), cytosine ("C"), guanine ("G"), thymine ("T"), or uracil (U) nitrogenous base, and a deoxyribose or ribose sugar, respectively. Modified nucleotide bases are also encompassed herein, wherein the nucleotide bases are, for example, hypoxanthine, xanthine, 7-methylguanine, inosine, xanthinosine, 7-methylguanosine, 5,6-dihydrouracil, 5-methylcytosine, pseudouridine, dihydrouridine, or 5-methylcytidine. In the context of the present invention, when describing nucleotides, "N" represents any nucleotide, "Y" represents any pyrimidine, and "R" represents any purine. Nucleotide monomers are linked by inter-nucleotide linkages, such as phosphodiester bonds, or phosphate analogs thereof and associated counter ions (e.g., $H^+$, $NH_4^+$, $Na^+$). Nucleic acid molecules of the invention may be double-stranded or single-stranded and will most often be double-stranded DNA. However, it is understood that the invention also applies to single-stranded DNA-single-stranded DNA duplexes, perfectly paired or not perfectly paired, or alternatively to single-stranded DNA-single-stranded RNA duplexes, perfectly paired or not perfectly paired, or alternatively to single-stranded RNA-single-stranded RNA duplexes, perfectly paired or not perfectly paired, as well as single-stranded DNA and single-stranded RNA. In particular, the invention applies to the secondary structures of a sole single-stranded DNA or of a sole single-stranded RNA. When the nucleic acid molecule is single-stranded RNA (e.g. mRNA) or a single-stranded RNA-single-stranded RNA duplex (e.g. viral dsRNA), said RNA may be reverse transcribed prior to being contacted with the Class 2 Type V Cas protein-gRNA complex. Duplexes may consist of at least partial re-pairing of two single nucleic acid strands obtained from samples of different origins. Nucleic acid molecules may be naturally occurring (e.g. of eukaryotic or prokaryotic origin), or synthetic. Nucleic acid molecules may comprise circular nucleic acid molecules, such as covalently closed circular DNA and/or circular RNA, including plasmids and/or circular chromosomes, or linear nucleic acid molecules. Nucleic acid molecules may notably comprise genomic DNA (gDNA), cDNA, hnRNA, mRNA, rRNA, tRNA, microRNA, mtDNA, cpDNA, cfDNA (such as ctDNA or cffDNA), cfRNA and the like.

The length of a nucleic acid may range from only a few monomeric units (e.g. oligonucleotides, which may range, for example, from about 15 to about 200 monomers in length) to several thousand, tens of thousands, hundreds of thousands, or millions of monomeric units. Preferably, the nucleic acid molecules comprise one or more cfDNA molecules. In a first aspect, the length of the nucleic acid molecule is less than 300 bp, for example comprised between about 125 and 225 bp, preferably between 130 and 200 bp. In a second aspect, the length of the nucleic acid molecule is equal or superior to 300 bp. In the present application, it should be understood that nucleic acid molecules are expressed in the 5' to 3' direction from left to right, unless specified otherwise.

The term "population of nucleic acid molecules" as used herein refers to more than one nucleic acid molecule. Said population may comprise one or more different nucleic acid molecules, of any length, of any sequence, as defined above. A population of nucleic acid molecules may notably comprise more than 103, 104, 105, 106, 107, 108, 109, or 1010 different nucleic acid molecules.

The "nucleic acid target region," "target nucleic acid region" or "target region" as used herein refers to a specific nucleic acid molecule that is present within a more complex sample or population of nucleic acid molecules or a specific nucleic acid region that is present within a larger nucleic acid molecule, and that is to be specifically targeted for isolation or enrichment. The term "region" as used herein refers to an uninterrupted nucleotide polymer of any length. When the target region is present within a larger nucleic acid molecule, it is preferably flanked on its first side by a first site that is at least partially complementary to the guide segment of the crRNA molecule or gRNA comprised in a Class 2 Type V Cas protein-gRNA complex. In some cases, the nucleic acid target region is furthermore flanked on its second side by a second site. Thus, said first site and said second site are located on either side of the target region. Said first site (and said second site when present) is located adjacent to said target region, preferably immediately adjacent, to said target region. Said first site and said target region (and said second site when present), may furthermore be flanked on one side or on both sides by non-target region(s). The term "adjacent" as used herein refers to the presence of a first nucleotide or nucleic acid region and a second nucleotide or nucleic acid region, wherein the two nucleotides and/or regions are present on a same uninterrupted nucleotide polymer. Thus, as long as the site that is at least partially complementary to the guide segment of the crRNA molecule or gRNA comprised in a Class 2 Type V Cas protein-gRNA complex and the target region are present on the same nucleotide polymer, they are considered to be adjacent. The term "immediately adjacent" as used herein refers to the proximity of a first nucleotide or nucleic acid region with a second nucleotide or nucleic acid region, wherein the two nucleotides and/or regions are immediately contiguous in the nucleotide polymer (i.e. no intervening nucleotides are present).

In the context of the present invention, a "site" corresponds to an uninterrupted nucleotide polymer of no more than 100 nucleotides in length, preferably of no more than 60 nucleotides in length. Said site is preferably a double-stranded nucleotide polymer. Preferably, said "site" is at least partially complementary to the guide segment of a gRNA, preferably completely complementary to the guide segment of the gRNA. Preferably, said site is about 12 to about 35 nucleotides in length, preferably 15 to 35 nucleotides in length. Preferably, said site comprises both a sequence that is at least partially complementary to the guide segment of the gRNA, more preferably completely complementary to the guide segment of the gRNA, and a PAM. Said PAM is preferably immediately adjacent to said target region. Said PAM is preferably located on the nucleic acid strand that is not hybridized to the Class 2 Type V Cas protein-gRNA complex (i.e. the "non-target" strand).

Said second site is preferably at least partially complementary to the guide segment of the crRNA molecule or gRNA comprised in a Class 2 Cas protein-gRNA complex, preferably a second Class 2 Type V Cas protein-gRNA complex. Alternatively, said second site may comprise or consist of a restriction site. In this case, said second site is preferably about 4 to 8 nucleotides in length.

In some embodiments, two or more different nucleic acid target regions may be isolated. The "target nucleic acid region" of the invention may therefore comprise one or more different regions, preferably at least 2, 5, 10, 25, 50, 100, or more regions. The nucleic acid target region may be coding or non-coding, or a combination of the two. The target region may be genomic or episomic. The target region may comprise one or more repeat regions, rearrangements, duplications, translocations, deletions, mismatches, SNPs, and/or modified bases, such as epigenetic modifications. In some cases, the nucleic acid target regions may be identical (e.g. corresponding to repeat sequences). In other cases, the nucleic acid target regions may be different. Preferably, the target nucleic acid region will have a length of at least about 10, 20, 50, 100, 250, 500, 1,000, 5,000, 10,000, 20,000, 30,000, 40,000, 50,000, 60,000, 70,000, 80,000, 90,000, or 100,000 nucleotides. Although a given gRNA may permit the isolation of multiple nucleic acids comprising target regions (for example, due to non-specific binding, or recognition of a site that is present more than once in a nucleic acid molecule), in the context of the present invention, each gRNA preferably recognizes a single site within a population of nucleic acid molecules. In some cases, two or more Class 2 Type V Cas protein-gRNA complexes will bind at different sites adjacent to different target regions, thereby enabling 2 or more regions to be isolated. Preferably, when said target regions are present on the same nucleic acid molecule, said nucleic acid target regions are separated from one another by at least 100, 200, 300, 500, 750, 1000, 2000, 5000, or 10000 nucleotides.

In some cases, two Class 2 Type V Cas protein-gRNA complexes will bind to sites located on either side of a target region, such that a single target region located between the two sites is isolated. In some cases, when multiple target regions are isolated, both of the above cases may be used in tandem (i.e. some target regions are adjacent to a single site, while others are adjacent to two sites, said two sites being located on either side of said target region). The selection of the number of Class 2 Type V Cas protein-gRNA complexes binding to sites adjacent to a given target region may depend on the length of the nucleic acid molecule comprising the target region, the desired structure of the isolated nucleic acid molecule (e.g. presence of a single-stranded overhang at one or both sites adjacent to the target region, etc.), and/or the downstream applications in which the target region will be used.

According to a preferred embodiment, at least two target regions are isolated, more preferably at least 5, at least 10, at least 25, at least 50, or at least 100 target regions are isolated. Preferably, the nucleic acid molecule is contacted with at least two Class 2 Type V Cas protein-gRNA complexes each comprising a different gRNA. More preferably the nucleic acid molecule is contacted with at least 5, at least 10, at least 25, at least 50, or at least 100 Class 2 Type V Cas protein-gRNA complexes, each Class 2 Type V Cas protein-gRNA complex enabling the isolation of a different target region.

Cas Protein

The term "Cas protein" as used herein refers to an RNA-guided endonuclease which specifically recognizes and binds to a site within a nucleic acid molecule, in the present case to a site that is adjacent to a target region. In order to recognize and bind to a specific site, the Cas protein complexes with a "guide RNA," or "gRNA," to form a "Cas protein-gRNA complex." Binding specificity of the Cas protein is determined by the gRNA, which comprises a "guide segment," whose sequence must be at least partially complementary to that of a specific site in the nucleic acid molecule. The guide segment within the Cas protein-gRNA complex hybridizes with said site, thereby forming a Cas protein-gRNA-nucleic acid complex. Successful binding of the Cas protein-gRNA complex to the site further requires the presence of a short, conserved sequence in the nucleic acid molecule that is located immediately adjacent to the hybridized region. This sequence is known as the protospacer-associated motif or "PAM." Thus, Cas protein-gRNA complex binding to a specific site within a nucleic acid molecule comprises both nucleic acid hybridization to the site via the guide segment and interaction of the Cas protein itself with the PAM. Following binding of the Cas protein-gRNA complex to a site within a nucleic acid, the Cas protein typically cleaves the nucleic acid by breaking the phosphodiester bonds between two adjacent nucleotides in each of the strands of a double-stranded nucleic acid molecule. Specifically, one domain of the Cas protein cleaves the nucleic acid strand that is hybridized with the gRNA, while a second domain of the Cas protein cleaves the non-hybridized nucleic acid strand. Cleavage of the two strands of a double-stranded molecule may be staggered, generating a single-stranded overhang, or blunt.

Three main classes of Cas protein have been described to date (Class 1, Class 2, and Class 3). Among the Class 2 Cas proteins, at least five different types have been identified to date (i.e. Type I, II, III, IV, V). As a non-limiting example, a Cas protein may be selected from the Class 2 Cas proteins, specifically the Class 2 Type V and Class 2 Type II Cas proteins, more specifically from among the Cas9, Cas12a (also referred to as Cpf1), C2c1, C2c3, and C2c2 (Cas13a) proteins.

As a non-limiting example, a Class 2 Cas protein may be from one of the following species: *Streptococcus pneumoniae, Streptococcus pyogenes, Streptococcus thermophilus, Streptococcus canis, Staphylococcus aureus, Neisseria meningitidis, Treponema denticola, Francisella tularensis, Francisella novicida, Pasteurella multocida, Streptococcus mutans, Campylobacter jejuni, Campylobacter lari, Mycoplasma gallisepticum, Nitratifractor salsuginis, Parvibaculum lavamentivorans, Roseburia intestinalis, Neisseria cinerea, Gluconacetobacter diazotrophicus, Azospirillum, Sphaerochaeta globosa, Flavobacterium columnare, Fluviicola taffensis, Bacteroides coprophilus, Mycoplasma mobile, Lactobacillus farciminis, Streptococcus pasteurianus, Lactobacillus johnsonii, Staphylococcus pasteuri, Filifactor alocis, Veillonella sp. Suterella wadsworthensis, Leptotrichia sp., Corynebacterium diphtheriae, Acidaminococcus sp., or Lachnospiraceae sp., Prevotella albensis, Eubacterium eligens, Butyrivibrio fibrisolvens, Smithella sp., Flavobacterium sp., Porphyromonas crevioricanis,* or *Lachnospiraceae bacterium* ND2006.

As a non-limiting example, a Class 2 Cas protein may be J3F2B0, QOP897, Q6NKI3, AOQ5Y3, Q927P4, A1IQ68, C9X1G5, Q9CLT2, J7RUA5, Q8DTE3, Q99ZW2, G3ECR1, Q73QW6, G1UFN3, Q7NAI2, E6WZS9, A7HP89, D4KTZO, DOW2Z9, B5ZLK9, FORSVO, A0A1L6XN42, F2IKJ5, SOFEG1, Q6KIQ7, AOAOH4LAU6, F5X275, F4AF10, U5ULJ7, D6GRK4, D6KPM9, U2SSY7, G4Q6A5, R9MHT9, A0A111NJ61, D3NT09, G4Q6A5, AOQ7Q2, or U2UMQ6. Accession numbers are from UniProt (www.uniprot.org), version last modified on Jan. 10, 2017. As a non-limiting example, the gene encoding a Class 2 Cas protein may be any gene comprising a nucleotide sequence wherein said sequence generates the amino acid sequence of the corresponding Cas protein, such as one of those listed above. The skilled person will easily understand that the nucleotide sequence of the gene may vary due to degeneracy of the genetic code, without altering the amino acid sequence. The Class 2 Cas protein may furthermore be codon-optimized for expression in a bacterial (e.g. *E. coli*), insect, fungal, or mammalian cell.

Class 2 Cas proteins and protein orthologs have also been identified in other bacterial species and are notably described in Example 1 of PCT application no. WO 2015/071474, incorporated herein by reference. In some cases, the Cas protein may be a homolog or an ortholog, for example, to a Class 2 Cas protein of one of the species listed above.

Variants and mutants of the wild-type Cas protein have been described. As a non-limiting example, Cas variants that retain endonuclease activity but which have improved binding specificity (e.g. the Class 2 Cas protein eSpCas9, as described in Slaymaker et al., Science, 2015, 351 (6268): 84-86) have been described.

Class 2 Type V Cas Proteins

The Cas proteins used in the context of the present method of isolating a nucleic acid target region are Class 2 Type V Cas proteins. Indeed, as indicated above, the first step (step a)) of the method of isolating a target region comprises contacting a population of nucleic acid molecules with a Class 2 Type V Cas protein. Specifically, step a) comprises contacting a population of nucleic acid molecules with a Class 2 Type V Cas protein-gRNA complex, wherein the gRNA comprises a guide segment that is complementary to at least a first site adjacent to said target region, thereby forming a Class 2 Type V Cas protein-gRNA-nucleic acid complex. When catalytically active, a Class 2 Type V protein complexed with an appropriate gRNA typically generates a staggered cut (e.g. a short 5' overhang of 4 to 6 nucleotides) that is distal to the PAM sequence (e.g. that is located at least 10 nucleotides distant to the PAM) of a double-stranded nucleic acid molecule (see for example Zetsche et al., Cell, 2015, 163 (3): 759-771). It has been further observed that a Class 2 Type V protein-gRNA complex may remain bound to a nucleic acid molecule after cleavage. In addition, the inventors have surprisingly shown here that when a nucleic acid molecule to which a Class 2 Type V protein-gRNA complex is bound is contacted with an enzyme having 3' to 5' single stranded exonuclease activity, a long 5' overhang (e.g. at least 9 nucleotides in length, preferably at least 12 nucleotides in length) is surprisingly generated. Without being limited by theory, the Class 2 Type V protein-gRNA complex may remain bound to the nucleic acid target strand (that does not comprise the PAM sequence) after cleavage, while the opposite strand (i.e. the strand comprising the PAM sequence) dissociates from the complex and becomes available for 3' to 5' single strand exonuclease digestion. The inventors have also surprisingly found that the variability in the cleavage position may be reduced when the Class 2 Type V protein-gRNA complex cleaves in presence of a 3' to 5' single-stranded exonuclease (See for example FIGS. 1B, 1C).

The Class 2 Type V Cas protein of the present invention is catalytically active (i.e. cleaves both strands of a double stranded molecule). Preferably, the Class 2 Type V Cas protein of the invention is selected from Cas12a and C2c1, more preferably Cas12a. The Cas12a protein is preferably the Cas12a protein of one of the appropriate species listed above, more preferably of one of the following species or strains: *F. novicida* U112 (accession no: AJI61006.1), *P. albensis* (accession no: WP_024988992.1), *Acidaminococcus* sp. BV3L6 (accessoion no: WP_021736722.1), *E. eligens* (accession no: WP_012739647.1), *B. fibrisolvens* (accession no: WP_027216152.1), *Smithella* sp. SCADC (accession no: KFO67988), *Flavobacterium* sp. 316 (accession no: WP_045971446.1), *P. crevioricanis* (accession no: WP_036890108.1) Bacteroidetes oral taxon 274 (accession no: WP_009217842.1), or *Lachnospiraceae bacterium* ND2006 (accession no: WP_051666128.1). In a preferred embodiment, said *Acidaminococcus* sp. BV3L6 Cas12a is a variant comprising the following amino acid substitutions: S542R/K607R or S542R/K548V/N552R (Gao et al., *Nat Biotechnol.* 2017, 35 (8): 789-792). The Cas12a protein is even more preferably selected from *Acidaminococcus* sp. Cas12a (also referred to as "AsCas12a"), *Lachnospiraceae bacterium* ND2006 Cas12a (also referred to as "LbaCas12a"), and *F. novicida* U112 Cas12a (also referred to as "FnCas12a").

Guide RNA

The term "guide RNA" or "gRNA" as used herein, generally refers to a crRNA molecule. This is notably the case when said gRNA is a Class 2 Type V gRNA. However, in some cases, the term gRNA may refer to two guide RNA molecules, consisting of a crRNA molecule and a tracrRNA molecule, or to a single guide RNA molecule, or sgRNA, that includes both crRNA and tracrRNA sequence segments, for example when the gRNA is a Class 2 Type II gRNA. In some cases, the crRNA may comprise a tracr-mate segment. The characteristics of the tracr-mate segment and the tracrRNA (e.g. length, presence of secondary structures, etc) are well-known to the skilled person. Furthermore, the skilled person is aware of when such segments or molecules are to be included in the gRNA molecule. In particular, such segments or molecules need not be comprised in a Class 2 Type V gRNA.

The gRNA molecule may be chemically modified, for example comprising base, sugar, or phosphate modifications of one or more ribonucleotides. Optionally, the 5' and/or 3' ends of the gRNA molecule may be modified, for example by covalent conjugation to another molecule or a chemical group.

The crRNA molecule or segment is preferably 20 to 75 nucleotides in length, more preferably 30 to 60 nucleotides, even more preferably 40 to 45 nucleotides in length. The crRNA molecule or segment preferably comprises a first region, referred to herein as the "guide segment," whose sequence is at least partially complementary to a sequence present in a nucleic acid molecule, said sequence present in a nucleic acid molecule preferably being a sequence located at a first site adjacent to a target region. Preferably, the guide segment of the gRNA of the present invention comprises at least 70%, at least 80%, at least 85%, at least 90%, at least 95%, at least 96%, at least 97%, at least 98%, at least 99%, or more preferably 100% sequence complementarity with a sequence present in a nucleic acid molecule. Preferably, when complementarity is less than 100%, mismatches are located near the crRNA end that hybridizes farthest from the PAM. As an example, when the Class 2 Type V Cas protein is Cas12a, mismatches are preferably comprised at the 3' end of the crRNA molecule or segment (e.g. within the last 7 nucleotides), as Cas12a recognizes a PAM at the 5' end of the crRNA. The guide segment is preferably at least 10, 11, 12, 13, 14, 15, 16, 17, 18, 19, 20, 21, 22, 23, 24, or 25 nucleotides in length, more preferably 15, 16, 17, 18, 19, 20, 21, 22, 23, 24, or 25, even more preferably 17, 18, 19, 20, 21, 22, 23, or 24 nucleotides in length. Alternatively, the guide segment is preferably from 10 to 30, more preferably 15 to 25, even more preferably from 17 to 24, nucleotides in length.

Preferably, when the Class 2 Type V Cas protein is Cas12a, the gRNA consists only of a crRNA molecule. A "Cas12a-gRNA complex" may thus also be referred to interchangeably herein as a "Cas12a-crRNA complex." When the gRNA is only a crRNA molecule, at least the guide segment must be present. An exemplary generic crRNA nucleotide sequence is shown in SEQ ID NO: 1 with the guide segment represented by the stretch of 'N' nucleotides. Preferably, the crRNA molecule further comprises a secondary structure. As a non-limiting example, a "secondary structure" present in the gRNA may be a stem-loop or hairpin, bulge, tetraloop, and/or pseudoknot. The terms "hairpin" and "stem-loop" are used interchangeably herein in the context of the gRNA and are defined below (see "hairpin adaptor" section). According to a preferred embodiment, said gRNA comprises at least one hairpin secondary structure.

Preferably, the crRNA molecule does not comprise a tracr-mate segment. Preferably, the guide segment is located at the 3'-end of the crRNA molecule. Preferably the secondary structure is located at or near the 5'-end of the crRNA molecule. The term "at or near the 5'-end" of a nucleic acid molecule as used herein refers to placement of a segment or structure within the first half of the molecule, from 5' to 3'. Similarly, the term "at or near the 3'-end" of a nucleic acid molecule as used herein refers to placement of a segment or structure within the last half of the molecule. Preferably, said crRNA is 40 to 50 nucleotides in length.

The term "complementary" as used herein refers to ability of one nucleic acid sequence or molecule (e.g. the gRNA) to undergo sequence-specific antiparallel nucleotide base pairing interactions with another nucleic acid sequence or molecule (e.g. the sequence in a nucleic acid molecule), resulting in the formation of a duplex or other higher-ordered structure. The main type of interaction is nucleotide base specific, e.g., A:T, A:U, and G:C, by Watson-Crick and Hoogsteen-type hydrogen bonding. This is also known as "nucleic acid binding," "hybridization," or "annealing." Conditions under which a nucleic acid hybridizes to the complementary region of a target site are well-known in the art (see, for example, Nucleic Acid Hybridization, A Practical Approach, Hames and Higgins, eds., IRL Press, Washington, D.C. (1985)). Hybridization conditions depend upon the particular application, and can be routinely determined by a person skilled in the art.

In the context of the present invention, complementary binding does not mean that the two nucleic acid sequences or molecules (e.g. the gRNA and the target region) must be entirely complementary to each other. Furthermore, it is not necessary for the crRNA sequence segment or molecule to be entirely complementary to the sequence in the nucleic acid molecule. Indeed, it is known that a Class 2 Cas protein-gRNA complex can specifically bind to a nucleic acid sequence having as few as 8 or 9 bases of complementarity with the gRNA. Preferably, no mismatches are present between the 10 bases of the gRNA that are closest to the PAM and the corresponding 10 bases of the complementary nucleic acid sequence which are located closest to the PAM, more preferably between the 6 bases of the gRNA that are closest to the PAM and the corresponding 6 bases of the complementary nucleic acid sequence which are located closest to the PAM, even more preferably between the base(s) of the gRNA which are located 4, 5, and/or 6 bases from the PAM and the corresponding base(s) of the complementary nucleic acid sequence which are located 4, 5, and/or 6 bases from the PAM. Indeed, if a mismatch is present at one or more of said base locations, binding will be unstable and cleavage at the target site by the Class 2 Cas protein-gRNA complex will be reduced or even abolished. Off-target hybridization can be reduced by increasing the length of the crRNA segment, or by placing mismatches at or near the end of the crRNA segment that is furthest from the PAM, as indicated above. Alternatively, the gRNA may be modified to have increased binding specificity via the presence of one or more modified bases or chemical modifications, such as those described in Cromwell et al., *Nat Commun.* 2018 Apr. 13;9 (1): 1448 or Orden Rueda et al., *Nat Commun.* 2017; 8:1610, incorporated herein by reference. Moreover, a nucleic acid may hybridize over one or more regions such that intervening regions are not involved in the hybridization event (e.g., a loop or hairpin structure). The person skilled in the art can easily design one or more gRNA molecules based on their general knowledge and in view of the parameters detailed above, according to the nucleic acid sequence(s) that are to be hybridized.

The ratio of the number of molecules of nucleic acid to Cas protein to gRNA (nucleic acid:Cas protein:gRNA) has previously been shown to influence the efficacy of isolation of a target region. The ratio the number of molecules of nucleic acid comprising a target region:Cas protein:gRNA may notably be optimized here according to the nucleic acid target region and/or the origin and/or the complexity of the population of nucleic acid molecules. Without being limited by theory, optimization may particularly depend on DNA complexity, with more complex nucleic acid populations requiring higher quantities of Cas protein and gRNA. As a non-limiting example, less complex nucleic acid populations may essentially comprise repeating sequences or PCR amplified fragments, whereas more complex nucleic acid populations may comprise genomic DNA. As a non-limiting example, a ratio of at least 1:10:20 may be used to in the present method when said nucleic acid molecule is present within a population of nucleic acid molecules generated by PCR. In contrast, a ratio of at least 1:1600:3200 is preferable when said population comprises or consists of *E. coli* genomic DNA, while a ratio of at least 1:100000:200000 is preferable when said population comprises or consists of human genomic DNA. When multiple gRNAs are used (e.g. wherein two gRNAs recognize a first site and a second site, said sites being located adjacent to a target region and on either side of said target region, or in multiplexing to prepare multiple nucleic acid molecules comprising different target regions), a single optimized ratio of nucleic acid:Cas protein:gRNA may be selected for all gRNAs. Alternatively, an optimized ratio may be selected for each gRNA individually.

According to a preferred embodiment, the ratio is at least 1:10:10, more preferably at least 1:10:20, even more preferably at least 1:10:50. A ratio of at least 1:10:20 is particularly preferred when template DNA is generated by PCR. Preferably, guide RNAs are selected for efficiency using a PCR template, followed by optimization of the ratio of nucleic acid comprising a target region:Cas protein:gRNA on an appropriate template, if necessary (e.g. if said template differs). Preferably, cleavage efficiency of a wild type Cas protein-gRNA complex is at least 70%, more preferably at least 80%, even more preferably at least 90%. Preferably, the efficiency of protection of a target region by a Cas protein-gRNA complex is at least 70%, more preferably at least 80%, even more preferably at least 90%. Preferably, the ratio of the number of nucleic acid target regions:Cas protein:gRNA is at least 1:200:400, more preferably at least 1:400:800, even more preferably at least 1:800:1600, at least 1:1600:3200, or at least 1:3200:6400 when the nucleic acid is prepared from nucleic acids of bacterial origin, such as gram-negative bacteria, such as *E. coli*. According to an alternative preferred embodiment, the ratio of the nucleic acid target region:Cas protein:gRNA is at least 1:10,000:20,000, more preferably at least 1:100,000:200,000. The skilled person can easily adapt the ratio of the nucleic acid target region:Cas protein:gRNA according to the target region to be prepared and/or the origin and/or complexity of nucleic acid molecules in view of the ratios provided above. While the proportion of Cas protein to gRNA may vary, the gRNA is advantageously provided in at least two-fold excess to the Cas protein to ensure that the Cas protein is successfully loaded with gRNA. Higher ratios of Cas protein (e.g. 1:20:40, 1:50:100, etc. for a PCR target) and, optionally, of gRNA (e.g. 1:10:30, 1:10:40, etc. for a PCR target) may of course be used. The above ratios are preferably used in step a) of the method of the invention, in particular with regard to the ratio of nucleic acid comprising a target region:Class 2 Type V Cas protein:gRNA. In cases where a second Class 2 Cas protein is present, the above ratios may also be used.

Protospacer Adjacent Motif (PAM)

The term "protospacer adjacent motif" or "PAM" as used herein, refers to a short nucleotide sequence (e.g. 2 to 6 nucleotides) which is recognized directly by the Cas protein itself, such as the Class 2 Type V Cas protein. The PAM sequence and its placement will vary according to the Cas protein, and can easily be determined by the person skilled in the art according to his general knowledge, or using techniques such as that described in Karvelis et al., *Genome Biology*, 2015, 16:253. As an example, the Cas12a protein of *F. novicida* recognizes the PAM 5'-TTTN-3' or 5'-YTN-3' while the Cas12a protein of *Acidaminococcus* sp. recognizes the PAM 5'-TTTN-3. As a further example, the Cas9 protein of *S. pyogenes* recognizes the PAM 5'-NGG-3'. In contrast, the Cas9 protein of *S. aureus* recognizes the PAM 5'-NN-GRRT-3' while an engineered Cas9 protein derived from *F. novicida* recognizes the PAM 5'-YG-3'. The PAM motif is generally located on the non-hybridized (or "non-target") strand of a double-stranded nucleic acid molecule and is immediately adjacent to the 5' or 3' end of the nucleic acid site that is hybridized to the gRNA. The required placement of the PAM depends on the Cas protein used (e.g. the PAM is preferably located immediately adjacent to the 3'-end of the gRNA when using the Cas9 protein, while the PAM is preferably located immediately adjacent to the 5'-end of the gRNA when using the Cas12a protein). In some cases, the PAM motif may be comprised in the gRNA molecule itself or in a separate DNA oligonucleotide that is added to the sample. As an example, addition of a PAM to the sample via one of these means may be necessary when using the present method to isolate single-stranded RNA molecules. Binding of a Class 2 Cas protein to the PAM is thought to slightly destabilize a double-stranded nucleic acid, thereby allowing hybridization of the gRNA to the nucleic acid sequence.

When the Cas protein is of Class 2 Type V, the PAM is preferably located on the non-hybridized strand of the target region immediately adjacent to 5' end of the gRNA. In contrast, the PAM of a Class 2 Type II Cas protein is preferably located on the non-hybridized strand of the target region immediately adjacent to the 3' end of the gRNA. However, in some cases, the PAM is preferably comprised within the gRNA molecule itself or on a DNA oligonucleotide.

Enzyme Having Single Stranded 3' to 5' Exonuclease Activity

According to the methods described herein, after contacting a population of nucleic acid molecules with at least one Class 2 Type V Cas protein-gRNA complex (e.g. in step a)), said method further comprises the step of contacting the population of nucleic acid molecules with at least one enzyme having single-strand 3' to 5' exonuclease activity (e.g. in step b)). This step degrades single-stranded nucleic acid molecules or single-stranded regions of double-stranded nucleic acid molecules from their 3' end. The skilled person will understand that this step may be performed at the same time as step a) when the target nucleic acid is a double-stranded molecule, as the enzyme is specific for single-stranded regions or molecules. However, in cases where the target nucleic acid is single-stranded, this step must be performed posterior to step a) to prevent non-desired degradation of the nucleic acid target.

The "enzyme having single-stranded 3' to 5' exonuclease activity" as used herein may refer to an exoribonuclease or an exodeoxyribonuclease or both. Said enzyme having 3' to 5' exonuclease activity may or may not have one or more additional enzymatic activities (e.g. specific or non-specific endonuclease activity). However, said enzyme preferably does not comprise double-stranded exonuclease activity. According to a preferred embodiment, said enzyme will also have single-stranded 5' to 3' exonuclease activity. As a non-limiting example, enzymes having single-stranded 3' to 5' exonuclease activity that may be used in the invention include exonuclease I (ExoI), S1 exonuclease, exonuclease T, exonuclease VII (ExoVII), and the like. In some cases, combinations of two or more enzymes, for example selected from those listed above, may be used. As a particular example, ExoVII and Exo I may be used in combination. Enzymatic degradation may be partial (i.e. single-stranded nucleic acid regions or molecules may be present in the population even after the population has been contacted with an enzyme having single-stranded 3' to 5' exonuclease activity) or complete. This may depend on incubation conditions, sample composition, the nucleic acid population itself (e.g. nucleic acid structures), or other variables as known to the skilled person. Thus, the term "degrading" comprises at least partially degrading the single-stranded nucleic acid molecules or regions present within the population of nucleic acid molecules.

According to a preferred embodiment, said enzyme having exonuclease activity does not have endonuclease activity. This may be advantageous when the target region comprises a site that may be recognized by a site-specific endonuclease, or when the target region is susceptible to degradation by a non-specific endonuclease. According to a preferred embodiment, said at least one enzyme having single-stranded 3' to 5' exonuclease activity is selected from exonuclease I, S1 exonuclease, exonuclease T, exonuclease VII, or a combination of two or more thereof. Preferably, said enzyme having single stranded 3' to 5' exonuclease activity is Exo I and/or ExoVII.

Upon incubation of the population of nucleic acids of step a) of the method provided herein, comprising a Class 2 Type V Cas protein-gRNA-nucleic acid complex at at least a first site with the at least one enzyme having single-stranded 3' to 5' exonuclease activity, a 5' single-stranded overhang is generated in said at least first site. The 5' single-stranded overhang may have a length of at least 9 nucleotides, preferably 9, 10, 11, 12 or more nucleotides, as further described herein.

Removing the Class 2 Type V Cas Protein-gRNA Complex

The Class 2 Type V Cas protein-gRNA complex stably and tightly binds to a nucleic acid molecule at a specific site to form a Class 2 Type V Cas protein-gRNA-nucleic acid molecule complex (also referred to herein as a Class 2 Type V Cas protein-gRNA-nucleic acid complex). Thus, in order to render the 5'-overhang bound by the Class 2 Type V Cas protein-gRNA complex accessible for downstream steps, it is necessary to remove the Class 2 Type V Cas protein-gRNA complex from the Class 2 Type V Cas protein-gRNA-nucleic acid molecule complex. Thus, the method provided herein further comprises a step c), of removing the Class 2 Type V Cas protein-gRNA complex from the population of step b). The term "remove" as used herein refers to the physical separation of the Class 2 Type V Cas protein-gRNA complex from the Class 2 Type V Cas protein-gRNA-nucleic acid molecule complex. Removal may be partial or complete. Preferably, removal is complete. In some cases, the Class 2 Type V Cas protein-gRNA complex may remain present in solution though unbound to the nucleic acid molecule, while in other cases it may be eliminated from the solution. The Class 2 Type V Cas protein-gRNA complex may notably be removed from solution by degradation of the Class 2 Type V protein and/or the gRNA. As a non-limiting example, Class 2 Type V Cas protein-gRNA complex may be removed by contacting the population of nucleic acid molecules with at least one protease, thereby degrading the Class 2 Type V Cas protein. Advantageously, contacting the population of nucleic acid molecules with at least one protease will also degrade any other proteins that may be present (i.e. other site-specific endonucleases, such as Class 2 Cas proteins that may be present in additional Class 2 Cas protein-gRNA complexes, contaminating proteins that remain from the initial sample, etc.). As a non-limiting example, the protease may be selected from serine proteases, cysteine proteases, threonine proteases, aspartic proteases, glutamic proteases, metalloproteases, and/or asparagine peptide lyases.

Additionally, or alternatively, Class 2 Type V Cas protein-gRNA complexes may be removed by contacting the population of nucleic acid molecules with a compound capable of chelating divalent cations (in particular $Mg^{2+}$), such as EDTA or EGTA. Indeed, the inventors have surprisingly shown that Class 2 Type V Cas protein-gRNA complexes may be removed when such a compound is added, without the need for enzymes or other chemicals degrading the Class 2 Type V Cas protein. Thus, according to a preferred embodiment, Class 2 Type V Cas protein-gRNA complexes are removed by contacting the population of nucleic acid molecules with a chelator of divalent cations, preferably a chelator chelating $Mg^{2+}$ cations. Preferably, said chelator is EDTA or EGTA. The quantity of EDTA or EGTA added is preferably at least 2-fold greater than the quantity of divalent cations to be chelated, more preferably at least 3-fold, 4-fold, 5-fold greater, even more preferably at least 10-fold greater than the quantity of divalent cations that are present. The skilled person can easily determine the appropriate quantity of chelator in view of the composition of the solution comprising the population of nucleic acid molecules (e.g. according to the presence and quantity of cations), and in further view of the embodiments provided herein. According to a particular example, EDTA is added at a concentration of at least 20 mM, more preferably at least 25 mM. In cases where at least one protease and a chelator of divalent cations are used in step c), said at least one protease and said chelator of divalent cations may be added simultaneously, wherein said chelator does not inhibit the activity of said at least one protease.

Additionally, or alternatively, Class 2 Type V Cas protein-gRNA complexes are removed by contacting the population of nucleic acid molecules with at least one RNase, such as RNaseA, RNase H, or RNase I, thereby degrading the gRNA. In another embodiment, as RNA is unstable at elevated temperatures, the sample may be heated (e.g. to at least 65° C.), optionally in the presence of divalent metal ions and/or under alkaline pH.

Oligonucleotide Probe

According to the method provided herein, after removing the Class 2 Type V Cas protein-gRNA complex(es), the population of nucleic acid molecules is contacted with an oligonucleotide probe (e.g. as provided in step d)). The term "oligonucleotide probe" as used herein refers to a polynucleotide molecule comprising a single-stranded region that is at least partially complementary to the 5' single-stranded overhang. The oligonucleotide probe may be a single-stranded polynucleotide or may comprise both single-stranded and double-stranded regions. In some cases, the oligonucleotide probe may be a hairpin adaptor. The oligonucleotide probe may notably comprise the DNA sequence that is equivalent to the guide segment of the gRNA molecule (i.e. with uracil bases replaced with thymine bases and ribose sugars substituted with deoxyribose sugars). Thus, said probe will comprise a region that is complementary to the 5' overhang, thereby enabling a double-stranded region, or duplex, to be formed between said oligonucleotide probe and said 5' overhang by hybridization. As a non-limiting example, the region of the oligonucleotide probe that is at least partially complementary to a 5' single-stranded overhang comprises fewer than 4, 3, or 2 mismatches with the 5' single-stranded overhang, more preferably fewer than 3 or 2 mismatches with the 5' single-stranded overhang, even more preferably the region of the oligonucleotide probe that is at least partially complementary to the 5' single-stranded overhang is fully complementary to said 5' single-stranded overhang (i.e. comprises no mismatches). As a non-limiting example, said 5' single-stranded overhang comprises 9 to 24 nucleotides. Thus, said 5' single-stranded overhang preferably comprises 9 to 24 nucleotides, preferably at least 9, 10, 11, 12, 13, 14, 15, 16, 17, 18, 19, 20, 21, 22, 23 or 24 nucleotides.

Given that the 5' overhang may vary (as illustrated for example in FIG. 1C), the sequence of said probe is preferably complementary to the region which continues up to, and which may include, the PAM site. Alternatively, the population of nucleic acid molecules may be contacted with multiple oligonucleotide probes (e.g. two, three, four, or more oligonucleotide probes) comprising sequences that are complementary to the different possible or expected 5' overhangs, such that a probe will successfully hybridize with most (e.g. at least 80%, 90%, 95%, 99%) if not all of the 5' overhangs that may be present, thereby forming duplexes. Alternatively, said oligonucleotide probe may further comprise a sequence which is complementary to that of the target region (i.e. that extends beyond the PAM site) at its 5' end. The oligonucleotide probe may further comprise additional nucleotides at its 3' extremity (i.e. the 3' region that does not bind to the 5' overhang), of any sequence and of any length, as is desired, for example for downstream applications. Thus, additional sequences may be comprised in the oligonucleotide probe, wherein said sequence(s) are present on one side or both sides of the sequence that is at least partially complementary to a 5' single-stranded overhang. A non-limiting illustration of an oligonucleotide probe is provided in FIG. 8.

While the oligonucleotide probe may be of any length, it is preferable that said probe has a length equal or inferior to 200 nucleotides, preferably equal or inferior 100 nucleotides, even more preferably equal or inferior to 50 nucleotides.

After hybridization, said probe is preferably ligated to the nucleic acid using methods well-known in the art, preferably via an enzyme having ligase activity, for example via a ligase such as a Taq DNA ligase. This step is particularly preferred when the 5' overhang has a length of 12 nucleotides or less, but may also be used when the 5' overhang has a length superior to 12 nucleotides.

In one aspect, the population of nucleic acid molecules obtained in step c) of the method described herein is further contacted with an enzyme having ligase activity. Preferably, said population of nucleic acid molecules is contacted with an enzyme having ligase activity during step d) or in a separate step after step d) but prior to step e). More preferably, said population of nucleic acid molecules is simultaneously contacted with said oligonucleotide probe and said enzyme having ligase activity, thereby generating at least one continuous nucleic acid molecule (i.e. having no nicks) in the form of a duplex. The simultaneous use of said oligonucleotide probe and said enzyme having ligase activity advantageously reduces the time necessary to perform the method.

In another further aspect, said population of nucleic acid molecules obtained in step c) of the method described herein is contacted with at least one enzyme catalysing the cleavage of a 5' nucleic acid flap from a double stranded nucleic acid molecule. Said enzyme thereby preferably phosphorylates the 5' end of the oligonucleotide probe after cleavage. Said 5' end may then be ligated to the nucleic acid molecule at the resulting nick site. In cases where said enzyme does not phosphorylate the 5' end, said population of nucleic acid molecules may be contacted with an enzyme phosphorylating 5' ends, such as a T4 polynucleotide kinase prior to ligation.

Figure 5:
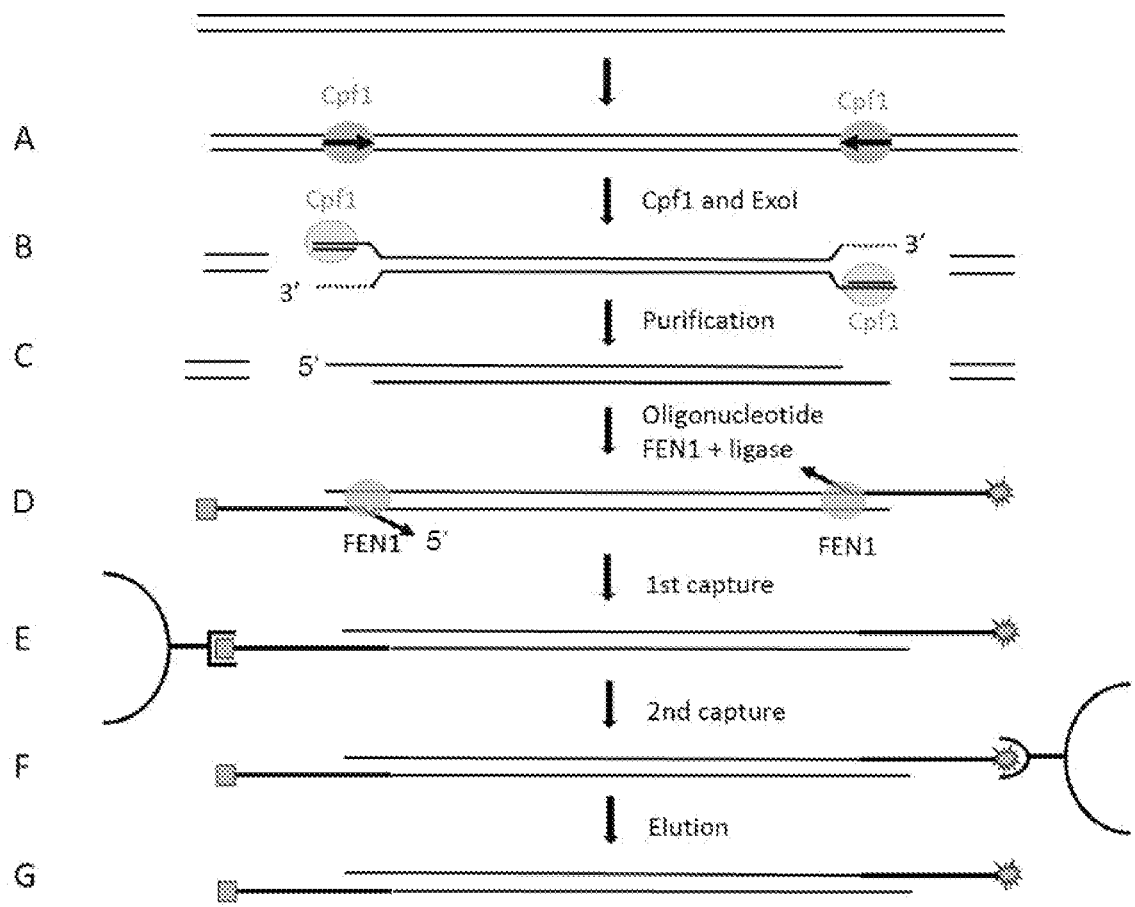
Figure 6:
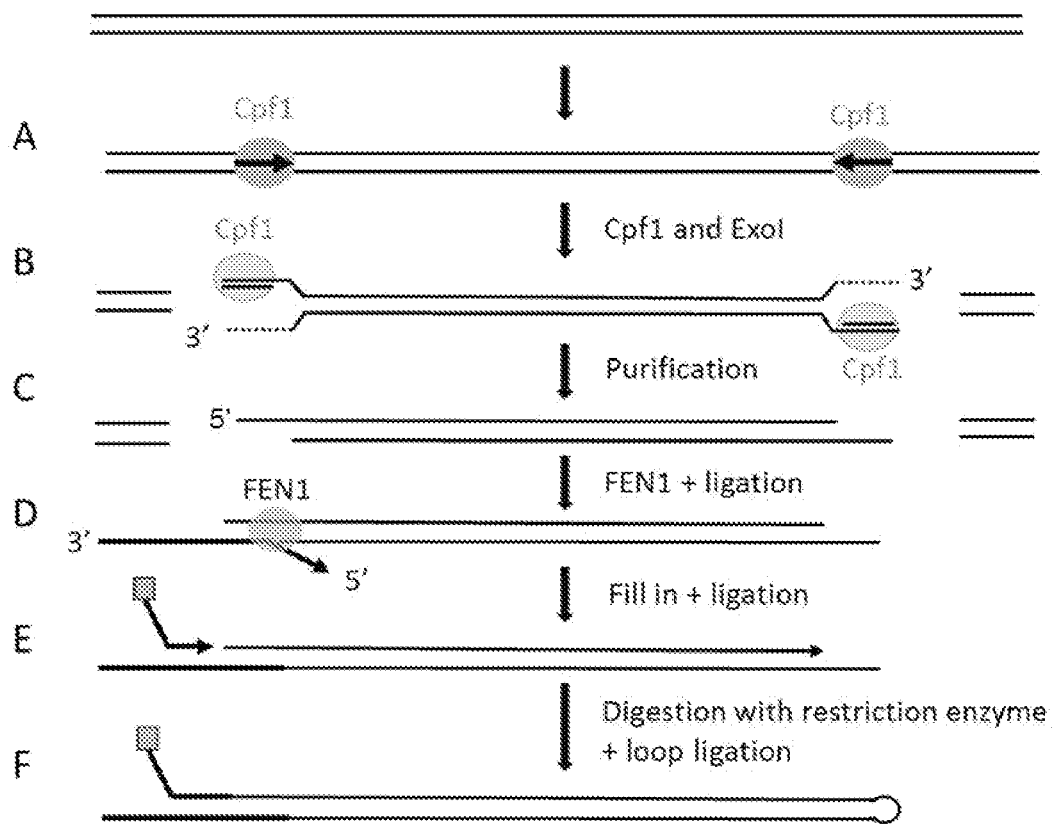

In a particular embodiment, the population of nucleic acid molecules is advantageously contacted with the FEN1 enzyme, which cleaves any 5'DNA flaps that may be present in the oligonucleotide probe after hybridization (as illustrated for example in FIGS. 5 and 6). Said step of contacting the population of nucleic acid molecules with the FEN1 enzyme may be performed during step d) or in a separate step after step d) but prior to step e). After or simultaneously to being contacted with the FEN1 enzyme, said population of nucleic acid molecules may be contacted with a ligase, thereby sealing the nick remaining after FEN1 cleavage.

Thus, the method provided herein may notably further comprise a step of cleaving a 5' nucleic acid flap from a double stranded nucleic acid molecule and/or a step of ligation. According to a particular embodiment, the exact position of the 3' end of the overhang obtained after cleavage with the Class 2 Type V Cas protein-gRNA complex may be determined, and said oligonucleotide probe designed such that no excess oligonucleotides are present at its 5' end. In this case, there is no need to contact the population of nucleic acid molecules with FEN1. Alternatively, the probe may comprise modifications that increase the strength of hybridization of the probe to the 5' overhang, such as base modifications, backbone modifications or 5' or 3' oligonucleotide modifications (e.g. the use of LNA, acridine, etc.), or strand displacement may be performed, such that the entire length of the oligonucleotide probe, including the sequence that is complementary to the target region, is hybridized. In these cases, ligation is not necessarily performed.

The oligonucleotide probe may further comprise a ligand capable of binding to a capture agent (e.g. a capture protein). The term "ligand" as used herein refers to a molecule, peptide, substrate, etc. that has an affinity with a capture agent. Said ligand may comprise a functional group. When said ligand is a peptide it may notably comprise natural, non-natural, and/or artificial amino acids. Said ligand may form a noncovalent or covalent bond with said capture agent upon interaction therewith. Ligand-capture agent interactions are further detailed below. In some cases, said ligand may be a single-stranded nucleotide overhang that is at least partially, preferably completely, complementary to an oligonucleotide that is anchored to a support. When multiple oligonucleotide probes are used to isolate a plurality of target regions, said probes may comprise the same or different ligands (e.g. a different ligand per target region, or a different ligand per group of target regions). Preferably, when isolating a plurality of target regions, all oligonucleotide probes will comprise a same ligand. Thus, the term "hybrid capture" as used herein refers to the hybridization of an oligonucleotide to a 5' overhang to form a duplex (e.g. as in step d) of the method provided herein), preferably wherein said oligonucleotide is ligated to said target nucleic acid to form a continuous duplex, followed by a step of isolating said duplex from said population of nucleic acid molecules (e.g. as in step e) of the method provided herein), preferably by directly or indirectly capturing said duplex (e.g. via a ligand on the oligonucleotide probe or a ligand on another molecule binding to said probe, such as a second oligonucleotide molecule, a protein, etc.).

The oligonucleotide probe may further comprise a cleavage site, such as an uracil base, an abasic site, or a restriction site. Preferably, said uracil base or abasic site is comprised within a single-stranded region of the oligonucleotide that is not complementary to the 5' overhang, and which therefore is not comprised in the duplex. Preferably, said restriction site is comprised within a double-stranded region of the oligonucleotide. In some cases, said restriction site may be generated by formation of the duplex. This is advantageous as the duplex may be separated from the ligand by cleavage at said cleavage site. Thus, according to a preferred embodiment, said oligonucleotide probe preferably comprises a cleavage site, even more preferably an uracil base, an abasic site, or a restriction site.

Duplex

After contacting said population of nucleic acids with an oligonucleotide probe as described above, the duplex is isolated from the population of nucleic acid molecules of step d), thereby also isolating the nucleic acid target region from the population of nucleic acid molecules (e.g. as in step e) of the method provided herein). Preferably, the population of nucleic acid molecules of step d) (i.e. comprising the duplex between the 5' overhang and the oligonucleotide probe) are contacted with a capture agent. This is particularly preferable when said probe comprises a ligand.

The term "capture agent" as used herein refers to an oligonucleotide, a protein or other molecule which forms a noncovalent or covalent bond with its ligand upon interaction therewith. Noncovalent bonds will typically include several weak interactions, such as hydrophobic, van der Waals, and hydrogen bonding which generally take place simultaneously. In a first example, when said ligand is a substrate for an enzyme, and said enzyme is the capture agent, said substrate may noncovalently bond with the enzyme. In a second example, a biotin ligand (or a biotin analogue such as desthiobiotin) will bond with the streptavidin capture agent, forming a quasi-covalent bond. As a third example, a digoxigenin ligand will noncovalently bond with a capture agent, said capture agent being an antibody directed against digoxigenin (anti-DIG). According to a particular example, said oligonucleotide probe is a hairpin adaptor, said hairpin adaptor comprising a digoxigenin ligand to which an anti-DIG capture agent may bond.

Alternatively, a "covalent bond" refers to a form of chemical bonding which is characterized by the sharing of pairs of electrons between atoms, or between atoms and other covalent bonds. As a first example, when said ligand comprises an amino acid, said amino acid may covalently bind to a capture agent. In a further example, said ligand will comprise a first functional group while said capture agent will comprise a second functional group, said first and second functional groups interacting to form the covalent bond, for example by click chemistry. Said covalent bond between said ligand and said capture agent may be, for example, an amide bond, an amine-thiol bond, a Cu(I)-catalyzed azide-alkyne cycloaddition, an alkyne-nitrone cycloaddition, etc. As a further example, said ligand may comprise a functional group (—COOH, —NH$_2$, —OH, etc.) capable of reacting with the carboxyl (—COOH) or amine (—NH$_2$) end of a protein capture agent. The techniques described in patent EP152886 using an enzymatic coupling for the attachment of DNA to a capture agent such as cellulose. Patent EP146815 also describes various methods of attachment of DNA to a capture agent. Similarly, patent application WO 92/16659 proposes a method using a polymer capture agent to attach DNA. The oligonucleotide probe may further comprise a "spacer" molecule or region to which the ligand is attached, advantageously providing the ligand with additional space to bind to its dedicated capture agent. As a non-limiting example, said spacer may be a polynucleotide region, tetraethylene glycol (TEG), or any other spacer known to the skilled person. Alternatively, the "spacer" may comprise or consist of a cleavage site such as a TEV protease cleavage site or an uracil base, an abasic site, or a restriction site as described above.

The capture agent is preferably anchored to a solid support. In some embodiments, a plurality of capture agents are anchored to a same solid support. As a non-limiting example, the capture agent may more particularly be fused, tethered, connected, etc. by any suitable structure or mechanism (e.g., expressed as a fusion, chemically linked (e.g., directly or indirectly), enzymatically linked, linked by a linker (e.g., peptide, nucleic acid, polymer, ester linkage, PEG linker, carbon chain, etc.)) to the solid support. As a non-limiting example possible supports include: glass and modified or functionalized glass, plastics (including acrylics, polystyrene and copolymers of styrene and other materials, polypropylene, polyethylene, polybutylene, polyurethanes, Teflon™, etc.), polysaccharides, nylon or nitrocellulose, ceramics, resins, silica or silica-based materials including silicon and modified silicon, carbon, metals, inorganic glasses, plastics, optical fiber bundles, and a variety of other polymers. The solid support may be selected for example from a well, tube, slide, plate, resin, or bead. In some embodiments, the solid support (e.g., resin, bead, etc.) is magnetic. In some embodiments, the solid support (e.g., resin, bead, etc.) is paramagnetic. When said solid support is a bead, the bead size ranges from nanometers, e.g. 100 nm, to millimeters, e.g. 1 mm.

According to a first aspect, the capture agent is anchored to a solid support prior to contacting said population of nucleic acid molecules with said capture agent. In other cases, the population of nucleic acid molecules is contacted with said capture agent prior to anchoring said capture agent to a solid support. In both cases, the nucleic acid target region is attached indirectly to the solid support.

After formation of a bond between said duplex and said capture agent, said duplex may, for example, be isolated from the population of nucleic acid molecules by separating said duplex from said population. Preferably, the support to which the capture agent (and therefore the duplex and associated target region) is anchored is separated from the population of nucleic acid molecules, through mechanical separation, though washing, or any method known to the person skilled in the art. Preferably, said duplex is isolated by washing according to methods known in the art, with non-target nucleic acid molecules (which are not bound to a solid support) being removed. Preferably, washing is performed at least twice. As a non-limiting example, the buffer used for washing may comprise a detergent or not. Said detergent may be an ionic or a non-ionic detergent. As a non-limiting example, said detergent may be polysorbate-20 (commonly known as Tween-20), 4-(1,1,3,3-Tetramethylbutyl)phenyl-polyethylene glycol (commonly known as Triton X100) or sodium dodecyl sulfate (SDS). The detergent may be comprised in the wash buffer at a concentration of about 0.05% to about 1.5%. The duplex may be washed with a single wash buffer or with multiple wash buffers. Each wash may use the same wash buffer or a different wash buffer. For example, a detergent-containing wash buffer may be used for one wash while a detergent-free wash buffer may be used for another wash.

In some cases, the isolated duplex, comprising the isolated target region, may be directly used in downstream applications. Alternatively, after isolation of said duplex, said target region is preferably released by any suitable mechanism (e.g., chemical or enzymatic cleavage). As a non-limiting example, said target region is released from said solid support (e.g. beads) by releasing said target region from said duplex. Releasing said target region from said duplex may notably comprise site-specific cleavage within said duplex, such as cleavage at restriction site within said duplex, for example by contacting said duplex with an appropriate restriction enzyme. Alternatively, said duplex (to which said target region is bound) is itself released from the solid support by any suitable mechanism. As a non-limiting example, a cleavage site present between the capture agent and the duplex (e.g. located within a single-stranded region or spacer region of the oligonucleotide probe) is cleaved (e.g., chemically, enzymatically) to release the duplex.

According to a preferred embodiment, the method provided herein further comprising a step of releasing said duplex from said target region, wherein releasing said duplex from said target region preferably comprises cleaving within said duplex, more preferably as described above.

As an alternative non-limiting example, in the case of non-covalent bonding between the capture agent and ligand, excess ligand may be added, wherein said ligand competes with the bound ligand such that the bound ligand (and therefore the duplex and target region) dissociates from the capture agent. As non-limiting example, said ligand and said excess ligand may be digoxigenin. In a particular example, said excess ligand may be a variant of the ligand, wherein said excess ligand has higher affinity for the capture agent than the ligand comprised in the oligonucleotide probe. This advantageously facilitates dissociation of the duplex, and thus the target region. As a particular example, said ligand may be desthiobiotin while said excess ligand is biotin. In still other embodiments, the capture agent is itself released from the surface, thereby releasing the entire complex comprising the capture agent, duplex, and target region. Each of these alternatives results in the release of the target region from the solid support. Advantageously, enzymatic cleavage yields a 5' or 3' overhang, preferably a 3' overhang.

According to a preferred embodiment, step e) comprises:
contacting the duplex with a capture agent, said capture agent preferably binding the ligand of the oligonucleotide probe.

Preferably, said capture agent is anchored to a solid support.

According to a preferred embodiment, when said capture agent is anchored to a solid support, the method of isolating a target region further comprises releasing the target region from said solid support, preferably by releasing said duplex from said target region.

In a particular embodiment, when said target region is contacted with a second Class 2 Type V Cas protein-gRNA complex in step a), said population of nucleic acids may be contacted with a second oligonucleotide probe in step d), wherein said second probe may comprise a same or a different ligand as that comprised in the first probe (e.g. both probes comprise a biotin ligand, or one probe comprises a biotin ligand while the second probe comprises a digoxigenin ligand).

When both of said probes comprise the same ligand, both duplexes (i.e. present on either side of said target region) will bond with a given capture agent. For example, when both duplexes comprise an oligonucleotide probe to which biotin is bound, both will bond to streptavidin coated beads. This may advantageously improve enrichment as each target region is simultaneously bound to a solid support via the covalent or non-covalent bonding of two ligands.

Thus, according to a particular embodiment, step e) comprises:
contacting said first and said second duplex with a capture agent, said capture agent binding the ligand of said first and said second probe,
releasing said first and said second duplex from said target region.

According to an alternative preferred embodiment, step e) comprises:
contacting said first and said second duplex with a capture agent, wherein said capture agent binds the ligand of said first and said second probe, and wherein said capture agent is anchored to a solid support,
releasing said nucleic acid target region from the solid support, preferably by releasing said first and said second duplex from target region.

In an alternative particular embodiment, when said second oligonucleotide probe comprises a different ligand, it is preferable to isolate said first duplex before isolating the second duplex. In this case, step e) is repeated a second time. This is particularly illustrated in FIG. 5, wherein each oligonucleotide probe comprises a different ligand, and sequential isolation is performed.

According to a preferred embodiment, step e) comprises:
contacting said first duplex with a first capture agent, said first capture agent binding the ligand of said first probe,
releasing said first duplex from said target region,
contacting said second duplex with a second capture agent, said second capture agent binding the ligand of said second probe,
releasing said second duplex from said target region.

According to a particular embodiment, step e) comprises:
contacting said first duplex with a first capture agent, said first capture agent binding the ligand of said first probe,
releasing said first duplex from said target region,
contacting a hairpin adaptor with a second capture agent, said second capture agent binding a ligand of said hairpin adaptor,
releasing said hairpin adaptor from said target region.

It will be understood by the person skilled in the art that when sequential isolation using two or more capture agents is performed, for example according to any of the above embodiments, isolation of the first and second duplex may be performed in any order.

Optional Supplementary Steps
Fragmentation

According to a particular embodiment of the invention, nucleic acid molecules may be fragmented before or after being contacted with the Class 2 Type V Cas protein-gRNA complex in the above method, advantageously after being contacted with the Class 2 Type V Cas protein-gRNA complex. The term "fragmentation" as used herein refers to an increase in the number of nucleic acid molecule 5'- and 3'-free ends by breaking a nucleic acid molecule into at least two smaller molecules. Nucleic acid fragmentation is advantageous as smaller nucleic acid molecules may be more easily isolated according to the method of the invention. "Non-target" nucleic acid regions (e.g. regions other than the target region and the adjacent site(s) to which the Class 2 Type V Cas protein-gRNA complex(es) will bind) are advantageously separated from said target in this step, thereby improving enrichment of the target region when performing the present method.

Fragmentation may be performed by shearing, for example by sonication, hydro-shearing, ultrasound, nebulization or by enzymatic fragmentation, for example by using one or more site-specific endonucleases, such as restriction enzymes. When fragmentation is performed by site-specific endonucleases, one or more site-specific endonucleases, preferably 1, 2, 3, 4, 5, or more site-specific endonucleases, may be used.

It will be understood that the ever-increasing number of sequences available in the databases enables the skilled person to easily identify one or more restriction enzymes whose cleavage sites are located outside of the nucleic acid comprising the target region. Advantageously, when two or more enzymes are used concomitantly, said enzymes are compatible with one another (e.g. same buffer requirements, inactivation conditions). Fragmentation may be partial (e.g. not all cleavage sites present in the nucleic acid molecules of the population are cut by the restriction enzyme) or complete. Thus, the term "fragmentation" comprises at least partially fragmenting the nucleic acids other than the target region and the adjacent site(s) to which the Class 2 Type V Cas protein-gRNA complex will bind.

Thus, in some embodiments, the method of preparing a nucleic acid comprising a target region further comprises the step of:
fragmenting the population of nucleic acid molecules, preferably by contacting said population with at least one site-specific endonuclease, more preferably with at least one restriction enzyme.

It is particularly preferred that only non-target regions (i.e. regions other than said target region and said first site to which the Class 2 Type V Cas protein will bind) are fragmented. When a second site is also present adjacent to said target region, it is further preferred that only regions other than said target region, said first site, and said second site are fragmented.

Thus, according to a particular embodiment, the method provided herein further comprises fragmenting said population of nucleic acid molecules prior to or during step b), preferably by contacting said population of nucleic acid molecules with at least one site-specific endonuclease, wherein said site-specific endonuclease:
does not cleave within the target region or said first site, and
does not cleave within said second site when said molecule comprises a second site,
preferably wherein said site-specific endonuclease is a restriction enzyme.

The skilled person will understand that the above step of fragmenting may occur at any step, for example prior to or during step a), between steps a) and b), during step b), between steps b) and c), during step c), or during step e). In cases where enzymatic fragmentation is performed and said site-specific endonuclease cleaves in the same conditions) as the Class 2 Type V Cas protein-gRNA complex (e.g. buffer, temperature), the step of fragmenting is preferably performed simultaneously to step a) of contacting a population of nucleic acid molecules with the Class 2 Type V Cas protein-gRNA complex.

According to a preferred embodiment, nucleic acid molecules are fragmented by contacting the population of nucleic acid molecules with at least one site-specific endonuclease, preferably at least 1, 2, 3, 4, 5, or more, site-specific endonucleases. Preferably, said site-specific endonuclease is a restriction enzyme, more preferably a Type II, Type III, or artificial restriction enzyme, even more preferably a Type II restriction enzyme, and/or a Class 2 Type V Cas protein-gRNA complex, such as a Cas12a-gRNA complex. Type II restriction enzymes include Type IIP, IIS, IIC, IIT, IIG, IIE, IIF, IIG, IIM, and IIB categories, as described for example in Pingoud and Jeltsch, *Nucleic Acids Res*, 2001, 29 (18): 3705-3727. Preferably, one or more enzymes from these categories are used to fragment nucleic acid molecules in the present invention. Appropriate enzymes can be selected by the skilled person. In cases where multiple restriction enzymes that are not compatible with one another are used, fragmentation may comprise multiple sequential steps, using different restriction enzymes and conditions (e.g. temperature, time, buffer). Preferably, the at least one site-specific endonuclease generates non-palindromic overhangs. Preferably, at least 50%, 60%, 70%, 80%, 90%, 95%, or 100% of cleavage sites are cleaved by the site-specific endonuclease(s). In cases where the site-specific endonuclease is a Class 2 Type V Cas protein-gRNA complex, said protein-gRNA complex binds and cleaves at a site exterior to the nucleic acid molecule comprising the target region that is being prepared. Preferably, site-specific endonuclease(s) bind a sequence that is located 100 to 5000 bases from the nucleic acid comprising a target region, more preferably 150 to 1000 bases from the nucleic acid region comprising the target region, even more preferably 250-750 bases from a nucleic acid region comprising a target region. Preferably, the site-specific endonuclease targets a specific sequence that is present multiple times within the nucleic acid molecule(s), such as the Alu element in the human genome, but that is absent from the nucleic acid molecule comprising the target region.

According to a particular embodiment, after contacting the population of nucleic acid molecules with a Class 2 Type V Cas protein-gRNA complex, said population is simultaneously contacted with at least one enzyme having 3' to 5' single stranded exonuclease activity and at least one site-specific endonuclease fragmenting said nucleic acid molecule according to any of the embodiments described above. This is particularly advantageous, as it reduces the duration of the method. According to another preferred embodiment, said enzyme having 3' to 5' single stranded exonuclease activity may also have site-specific endonuclease activity. According to this embodiment, the cleavage site(s) of the enzyme having site-specific endonuclease activity is/are located outside of said first site and said target region. When a second site is present, the cleavage site(s) are also located outside of said second site. The use of a single enzyme having both exonuclease and site-specific endonuclease activity is particularly advantageous as it reduces the number of reagents required and cost.

Site Specific Endonuclease

In some cases, as indicated above, the method may further comprise contacting the population of nucleic acid molecules with a site-specific endonuclease at any stage prior to step c) (i.e. before, during or after step a) or step b)). The site-specific endonuclease is preferably a Cas protein-gRNA complex, more preferably a Class 2 Cas protein-gRNA complex, even more preferably a second Class 2 Type V Cas protein-gRNA complex. However, any other site-specific nucleases that stably bind a nucleic acid at a specific site, such as transcription activator-like effector nucleases (TALENs) or zinc-finger proteins, are also included in the scope of the invention. This step is notably advantageous in cases where both ends of a molecule are to be modified (e.g. generation of two 5' overhangs, one on either side of the target region). In cases where it is desirable to obtain a molecule comprising a single 5' overhang on one side of the target region and a blunt end on the other side of the target region, said population of nucleic acid molecules is advantageously contacted with a Class 2 Type II Cas protein-gRNA complex, preferably a Cas9-gRNA complex.

Said site-specific endonuclease will bind within a nucleic acid molecule.

Thus, according to a preferred embodiment, the method of the invention further comprises contacting said population of nucleic acid molecules with a site-specific endonuclease prior to step c), said site-specific endonuclease being preferably a TALEN, a zinc-finger protein, or a Class 2 Cas protein-gRNA complex, more preferably a second Class 2 Type V Cas protein-gRNA complex, wherein the gRNA comprises a guide segment that is complementary to a second site, wherein said second site is adjacent to said target region, and wherein said first site and said second site are located on either side of said target region. When the population of nucleic acid molecules is contacted with a plurality of Cas protein-gRNA complexes (e.g. multiple Class 2 Type V Cas protein-gRNA complexes), it is particularly preferred that the population of nucleic acid molecules be contacted simultaneously with all of said Cas protein-gRNA complexes. This is advantageous as the duration of the method is reduced. Preferably, said site-specific endonucleases are Cas12a-gRNA complexes. Preferably, the PAM site is immediately adjacent to a nucleic acid target region. Thus, according to a particular embodiment of the method, step a) comprises contacting a population of nucleic acid molecules with both first and second Cas12a-gRNA complexes, said first and second complexes binding respectively to a first and second site, said first and second sites being located adjacent to and on either side of said target region.

According to a preferred embodiment, the site-specific endonuclease binds to a site located at least 50 nucleotides, preferably at least 100, 250, 500, 1,000, 5,000, 10,000, 20,000, 30,000, 40,000, 50,000, 60,000, 70,000, 80,000, 90,000, 100,000, 200,000, 500,000, 750,000, or 1,000,000 nucleotides distant to the Class 2 Type V Cas protein-gRNA-nucleic acid complex. Thus, according to a preferred embodiment, the target region has a length of at least 50, 100, 250, 500, 1,000, 5,000, 10,000, 20,000, 30,000, 40,000, 50,000, 60,000, 70,000, 80,000, 90,000, 100,000, 200,000, 500,000, 750,000, or 1,000,000 nucleotides.

According to a preferred embodiment, when said site-specific endonuclease is a second Class 2 Type V site-specific endonuclease, said population is contacted with a second oligonucleotide probe comprising a sequence that is at least partially complementary to a second 5' single-stranded overhang in said second site, thereby forming a second duplex. In this case, said first and second probes preferably comprise different ligands, said ligands binding to different capture agents, as discussed herein.

Hairpin Adaptor

In some cases, the method may further comprise a step of contacting the population of nucleic acid molecules with a hairpin adaptor. The hairpin adaptor binds to one or more free ends of one or more nucleic acid molecules that are present in said population. Said step may be performed prior to or simultaneously to being contacted with said Class 2 Type V Cas protein-gRNA complex. When fragmentation is performed, said step is preferably performed after fragmentation. The term "hairpin" or "hairpin adaptor" as used herein refers to a molecule that base pairs with itself to form a structure having a double-stranded stem and a loop, wherein the 5'-end of one strand is physically linked to the 3'-end of the other strand through an unpaired loop. Said physical link may be either covalent or non-covalent. Preferentially, said physical link is a covalent bond. The term "loop" as used herein refers to a succession of nucleotides of a nucleic acid strand that are not paired through hydrogen bonds with nucleotides of the same or another strand of said nucleic acid, and is therefore single-stranded. The "stem" as used herein refers to a region of intra-strand pairing. Preferably, the stem comprises at least 3, 5, 10, or 20 base pairs, more preferably at least 5, 10, or 20 base pairs, even more preferably at least 10 or 20 base pairs. When the hairpin binds to the free end of a double-stranded nucleic acid molecule, the 3' and 5' ends of the hairpin ligate to the 5' and 3' ends of the double-stranded nucleic acid molecule, respectively. Said hairpin may bind to an overhang or to a blunt end. Thus, the hairpin adaptor need not bind to a specific sequence or site.

Preferably, said hairpin adaptor binds to one or both of the free ends of a nucleic acid molecule. Said hairpin adaptor may specifically bind to one of the free ends of a nucleic acid molecule or non-specifically bind to all free ends of all nucleic acid molecules. As a non-limiting example, specific binding may be performed by fragmenting the nucleic acid molecule(s) with a non-palindromic restriction enzyme, thereby generating different overhangs at each new free end of the nucleic acid molecule. In other cases, the nucleic acid molecule(s) may comprise blunt ends to which the hairpin adaptor may be ligated, thus binding non-specifically. In a further example, the population of nucleic acid molecules (fragmented or not) may undergo A-tailing, such that hairpin adaptors comprising an appropriate "T" nucleotide overhang may then be hybridized and ligated to said sites. In a preferred embodiment, said first site bound by the Class 2 Type V Cas protein-gRNA complex and said free end (and therefore said hairpin adaptor) are located on either side of said target region. This structure may be obtained by contacting the population of nucleic acids with a hairpin adaptor that specifically binds to a free end adjacent to nucleic acid target region after removal of Class 2 Type V Cas protein-gRNA complex, with said first side and said free end being located on either side of said target region. Alternatively, said hairpin adaptor may bind to all free ends, with said population of nucleic acids being contacted with said hairpin adaptor prior to or simultaneously to being contacted with said Class 2 Type V Cas protein-gRNA complex (see also FIG. 3).

The term "free end" as used herein refers to the end of a nucleic acid molecule, which may comprise a phosphate group on the 5' end and/or a hydroxyl group on the 3' end. The free end may be blunt or comprise a single-stranded overhang. Said single-stranded overhang may be a 3' or 5' overhang. Said single-stranded overhang preferably has a length of less than 100, 50, 25, 10, 5, 4, 3, or 2 nucleotides, more preferably said single-stranded overhang has a length of 1 nucleotide.

According to a preferred embodiment, the hairpin adaptor binds to a free end located at least 50 nucleotides, preferably at least 100, 250, 500, 1,000, 5,000, 10,000, 20,000, 30,000, 40,000, 50,000, 60,000, 70,000, 80,000, 90,000, 100,000, 200,000, 500,000, 750,000, or 1,000,000 nucleotides distant to the Class 2 Type V Cas protein-gRNA-nucleic acid complex. Thus, according to a preferred embodiment, the target region has a length of at least 50, 100, 250, 500, 1,000, 5,000, 10,000, 20,000, 30,000, 40,000, 50,000, 60,000, 70,000, 80,000, 90,000, 100,000, 200,000, 500,000, 750,000, or 1,000,000 nucleotides Preferably, said hairpin adaptor is linked to the nucleic acid molecule, preferably ligated to the nucleic acid molecule. More preferably, step a) comprises contacting the population of nucleic acids with a hairpin adaptor and linking said hairpin adaptor to a nucleic acid molecule free end. In a preferred embodiment, the method further comprises a step of linearizing the population of nucleic acid molecules prior to contacting said population with a hairpin adaptor, if necessary (e.g. when the sample comprises circular nucleic acid molecules).

According to a particular embodiment, when multiple target regions are isolated, the population of nucleic acid molecules may be contacted with both site-specific endonuclease(s), preferably Class 2 Cas protein-gRNA complexes as described herein, and hairpin adaptor(s), in addition to a Class 2 Type V Cas protein-gRNA complex(es). Said population of nucleic acid molecules may be contacted with said molecules simultaneously or sequentially in any order.

Incubation and/or Storage

According to a particular embodiment of the invention, nucleic acid molecules may be stored after step c), step d), or step e) of the method provided herein.

According to a particular embodiment, nucleic acid molecules may be incubated before, during, or after any steps of the method provided herein. Preferably, the population of nucleic acid molecules may be subject to incubation during or after being contacted with the Class 2 Type V Cas protein-gRNA complex (step a)), during or after being contacted with at least one enzyme having 3' to 5' single stranded exonuclease activity (step b)), during removal of the Type V Cas protein-gRNA complex, during step d) of contacting the population of step c) with an oligonucleotide probe, and/or during step e) of isolating said duplex from the population of nucleic acid molecules. Preferably, the population of nucleic acid molecules is subject to incubation times ranging from 15 minutes to two hours. The skilled person is notably aware of appropriate incubation times/temperatures which maximize enzymatic activity, or that reduce the duration of the method while maximizing enzymatic activity, and may furthermore adapt incubation times/temperatures if desired.

Downstream Applications

A nucleic acid target region that has been isolated according to one of the methods described above is advantageously highly enriched. Isolated nucleic acids are particularly useful in a wide range of applications. Indeed, the nucleic acids isolated according to the present invention may be subject to further processing, reactions, or analyses, which may occur in the same container, or not. As an example, the nucleic acids isolated according to the present invention may be used for detection, cloning, sequencing, amplification, hybridization, cDNA synthesis, diagnostics and any other methods known to the skilled person which require nucleic acids. In some cases, the isolated nucleic acid target region may undergo further isolation, enrichment, or purification.

The present method is particularly suited for generating a library of hairpins following isolation of the one or more target regions, wherein each hairpin comprises at least one nucleic acid target region. This method is thus particularly convenient for detecting or determining the sequence of a target region of interest, e.g. a particular allele, isolated from an entire population of nucleic acid molecules, for example in a biological sample, or an epigenetic modification of a target region of interest.

According to a preferred aspect of the invention, the method of the invention may further comprise additional steps. As a non-limiting example, the isolated nucleic acids may be further purified using well-known purification methods (e.g. bead or column purification, such as purification with paramagnetic beads) to remove proteins, such as protease, salts, EDTA, excess oligonucleotides, etc. As a non-limiting example, nucleic acid molecules may be hybridized and/or ligated to the target region or to sites located adjacent to the target region, single-stranded gaps in the nucleic acid molecule may be filled in by synthesis of the complementary strand, and/or strand displacement may be performed. One or more of these additional steps are particularly useful for generating a hairpin library, but may also be necessary when preparing the isolated nucleic acid for other downstream applications. In a particular example, when one or more double-stranded nucleic acid target regions, or molecules comprising said target region, are isolated according to the methods of the present invention, a hairpin molecule, as has been previously defined herein, may then then be ligated to one or both free ends of said target region or molecule. Preferably, a hairpin is ligated to one free end of the isolated nucleic acid target region or molecule (see also FIG. 6). Preferably, at least one free end of said isolated nucleic acid target region or molecule comprises a 3' or 5' overhang.

Preferably, said hairpin comprises a 3' or 5' overhang that is at least partially complementary to at least one of the 5' or 3' overhangs, respectively, of said isolated nucleic acid target region or molecule. Preferably, said hairpin is ligated to a 3' overhang on one end of the isolated nucleic acid target region or molecule. As an alternative example, the hairpin is advantageously ligated to an overhang in presence of the FEN1 enzyme, which cleaves 5' DNA flaps. Indeed, the inventors have found that ligating a hairpin to an overhang in presence of FEN1 promotes cleavage of protruding nucleotides present at the 5' end of the oligonucleotide in cases where catalytically active Cas12a is used for the preparation of the fragment to be isolated (see also FIG. 7). Indeed, Class 2 Type V Cas proteins such as Cas12a do not always cleave at the same position, as illustrated in FIG. 1C. Following ligation of said hairpin, gap filling and ligation reactions may be performed using methods well-known in the art.

Thus, according to a first embodiment, the method of the invention further comprises the step of:
hybridizing and/or ligating one or more single or double-stranded nucleic acid molecules to the isolated nucleic acid target region.

Preferably, said single or double-stranded nucleic acid molecule is hybridized to a 5'- or 3'-overhang adjacent to the target region. Following hybridization, ligation is preferably performed. In a particular embodiment, the method may comprise the steps of:
hybridizing at least one single-stranded nucleic acid molecule to a 5'- or 3'-overhang adjacent to the target region, and
ligating said single-stranded nucleic acid molecule to the double-stranded region.

However, ligation may also be performed directly without hybridization when a single-stranded nucleic acid molecule (e.g. an oligonucleotide) binds to a single-stranded region of the target that directly abuts a double-stranded region.

According to a preferred embodiment, said single-stranded nucleic acid molecule hybridizes to a single-stranded region of the oligonucleotide probe, which remains within the nucleic acid molecule comprising the target region. Preferably, said oligonucleotide probe comprises a single-stranded sequence to which all single-stranded nucleic acid molecules may hybridize. Said single-stranded sequence may be an artificial sequence (i.e. not naturally occurring). This presence of such a single-stranded sequence within the probe is particularly advantageous when a plurality of nucleic acid target regions are isolated, as there is no need to design multiple sequence-specific single-stranded nucleic acid molecules, for example for the construction of hairpin molecules. Indeed, all single-stranded nucleic acid molecules may bind to the same sequence, which is present in all probes. Thus, said sequence in the probe and said single-stranded nucleic acid molecule comprising a complementary sequence are said to be "universal." This is particularly illustrated in FIG. 8.

According to another embodiment, the method comprises the steps of:
hybridizing at least one single-stranded nucleic acid molecule to the isolated target region,
extending the single-stranded nucleic acid molecule to the double-stranded region, preferably by contacting said isolated target region with a nucleic acid polymerase, and
ligating said extended single-stranded nucleic acid molecule to the double-stranded region.

According to a preferred embodiment, the at least one single-stranded nucleic acid molecule is hybridized and polymerized on a 3'-overhang. Preferably, said single-stranded nucleic acid molecule hybridizes to a region that located outside the first site and target region on the sequence provided by the oligonucleotide probe. Preferably, said single-stranded nucleic acid molecule hybridizes to a region that is located 2 bases or more from the duplex formed by the oligonucleotide probe and the 5' overhang (see also, for example FIG. 6(E), FIG. 8). Methods of hybridization, extension and ligation are well-known to the skilled person.

In some cases, any of the above embodiments may be repeated, for example to add a second single-stranded nucleic acid molecule to the isolated target region (see for example FIG. 6). Said second single-stranded nucleic acid molecule may be hybridized to the same strand or to the opposite strand, and may comprise a label or ligand, or not. Said single-stranded nucleic acid molecule may by only partially complementary to the sequence of the isolated target region. Said single-stranded nucleic acid molecule may preferably comprise a spacer region, for example, a 12-carbon spacer or any other spacer described herein or known to the skilled person, that does not bind to the isolated target region (e.g. is not complementary to the sequence of the isolated target region). Preferably, the single-stranded nucleic acid molecule(s) comprises a 5' phosphate group for ligation.

Optionally, excess reagents, such as non-hybridized single-stranded nucleic acid molecules are then be eliminated. As an example, non-hybridized single-stranded nucleic acid molecules are eliminated by contacting the sample comprising the isolated target region with an enzyme having 3' to 5-exonuclease activity, more preferably ExoI.

A hairpin structure is preferably obtained according to any of the methods described herein which is particularly adapted for use in downstream applications, such as those described in WO 2011/147931, WO 2011/147929, WO 2013/093005, and WO 2014/114687, incorporated herein by reference in their entirety. Alternatively, the hairpin structure generated herein may be particularly adapted for use as a hairpin precursor molecule (e.g. the HP2 molecule described in WO 2016/177808, incorporated herein by reference in its entirety).

Preferably, the one or more single-stranded nucleic acid molecules of any of the embodiments described herein has optimized hybridization specificity as described in Zhang et al., *Nat Chem*, 2012, 4 (3): 208-214, incorporated herein by reference in its entirety. Alternatively, said one or more single-stranded nucleic acid molecules of any of the embodiments described herein may be degenerate.

Preferably, the one or more single-stranded nucleic acid molecules of any of the above embodiments comprises a label or ligand. As a non-limiting example, the label or ligand may be FITC, digoxigenin, biotin, or any other label known to the skilled person. Said label or ligand may be conjugated to the proteins using techniques such as chemical coupling and chemical cross-linkers. Advantageously, said target region may be detected and, optionally, quantified within a sample, for example via a fluorescent label or other detectable label or ligand known to the skilled person. In some cases, the target region may be further isolated or purified using said ligand. In a first aspect, the target region may be isolated via a further pull-down reaction, for example on beads coated with streptavidin when the oligonucleotide is labelled with biotin, according to methods known by the skilled person. In a second aspect, the target region may be attached to a support, such as a bead or a chip, via said label or ligand. Preferably, said support is functionalized to facilitate attachment of the labelled target region, said label or ligand reacting with the functional groups present on the support (for example, a support may be coated with streptavidin or a COOH group, that reacts with an appropriate label or ligand).

According to a particular embodiment, at least one of the single-stranded nucleic acid molecules of any of the above embodiments comprises a sequence complementary to an oligonucleotide bound to a solid support (e.g. a surface), when said sequence is not comprised in the oligonucleotide probe. Preferably, said oligonucleotide comprises a modification at its 3' end to prevent extension. Single-stranded nucleic acid molecule hybridization and ligation to the 3' overhang, with or without a tag, advantageously generates a hairpin structure which is particularly adapted for use in downstream applications, such as those described in WO 2011/147931, WO 2011/147929, WO 2013/093005, and WO 2014/114687. Preferably, any of the embodiments described herein generate a hairpin having a "Y" shape.

The present invention further allows the skilled person to enumerate the number of nucleic acid molecules carrying the said sequence. According to a preferred embodiment, the method of the present invention further comprises detecting and quantifying nucleic acid molecules as described in WO 2013/093005.

Isolated target regions of the present invention are particularly suited to downstream analyses by single-molecule analysis methods, such as the methods described in WO 2011/147931 and WO 2011/147929, nucleic acid detection and quantification methods, such as that as described in WO 2013/093005, and methods for detecting protein binding to nucleic acids as described in WO 2014/114687. Thus, further embodiments and applications of the present method can be found in these applications, which are herein incorporated by reference in their entirety.

According to a preferred embodiment of the invention, the method comprises the enrichment of an SNP or genetic mosaicism comprised within an isolated target region. In some cases, the SNP or genetic mosaicism is located within the target region itself (it is therefore not located in a site recognized by a gRNA within a Class 2 Type V Cas protein-gRNA complex). However, in other cases, the SNP or genetic mosaicism may be located in a site recognized by a gRNA within a Class 2 Type V Cas protein-gRNA complex. In a particular embodiment, the gRNA comprises the nucleotide base corresponding to the minor allele of the SNP. When multiple alleles of the SNP are present at a given locus, multiple gRNA molecules may be provided, corresponding to each allele, preferably to each minor allele. In cases where gRNA molecules corresponding to both the major and minor alleles are provided, the number of isolated target regions comprising each allele may be quantified, for example to determine if a subject is homozygotic or heterozygotic at the SNP locus. Preferably, the base corresponding to the SNP locus is located within the gRNA sequence at any one of bases −1 to −10, preferably −1 to −6, preferably −4, −5, or −6 relative to the PAM site. Indeed, when a mismatch occurs at one or more of these bases, hybridization of the gRNA to the region comprising the SNP locus is reduced. Protection of the nucleic acid region from exonuclease digestion is also reduced or abolished in this case. This positioning is particularly advantageous as the presence or absence of an SNP may be determined with reduced possibility for error. In some cases, the target nucleic acid region is sequenced to determine the allele at the SNP locus. This may notably be performed when a gRNA comprising a degenerate base at SNP locus is used, to identify the alleles that may be present at adjacent SNP loci within the target region, or when said SNP is comprised within the target region itself (i.e. the gRNA is complementary to a site adjacent to said target region). Indeed, as is well-known to the person skilled in the art, SNPs that are located close to one another in the genome tend to be inherited together.

The degree by which cleavage of the target region is reduced or abolished will vary according to experimental conditions, the Class 2 Cas protein used, and/or the gRNA used. For example, it is known that Cas12a has greater binding specificity than Cas9 (Strohkendl et al., *Molecular Cell*, 2018, 71:1-9). Thus, hybridization specificity or protection of a region comprising a mismatch will be greater when Cas9 is used than when Cas12a is used. A Cas12a protein or variant thereof having optimized binding specificity may notably be used according to whether or not isolation of regions comprising a mismatch is desired.

According to a preferred embodiment of the invention, the method may further comprise sequencing the isolated target region. Many sequencing methods are available in the art. The method of the invention is particularly well suited for generating hairpins for use in single-molecule sequencing methods, such as those described in described in WO 2011/147931 or WO 2011/147929. The isolated nucleic acid may further be used as a template for specific or non-specific polymerase chain reaction, isothermal amplification, such as loop-mediated isothermal amplification, strand displacement amplification, helicase-dependent amplification, nicking enzyme amplification reaction, reverse transcription, enzymatic digestion, nucleotide incorporation, oligonucleotide ligation, and/or strand invasion. Isolated nucleic acid may also be used as a substrate for sequencing, such as Sanger dideoxy sequencing or chain termination, whole genome sequencing, hybridization-based sequencing, pyrosequencing, capillary electrophoresis, cycle sequencing, single-base extension, solid-phase sequencing, high-throughput sequencing, massively parallel signature sequencing, nanopore-based sequencing, transmission electron microscopy sequencing, optical sequencing, mass spectrometry, 454 sequencing, sequencing by reversible terminators, "paired end" or "mate pair" sequencing, exonuclease sequencing, ligation sequencing (e.g. SOLID technology), short-read sequencing, single molecule sequencing, chemical degradation sequencing, sequencing by synthesis, massive parallel sequencing, real-time sequencing, semiconductor ion sequencing (e.g. Ion Torrent), multiplex sequencing of paired-end ditags (MS-PET), sequencing by droplet microfluidics, partial sequencing, fragment mapping, as well as combinations of any of these methods.

According to a preferred embodiment, the method of the invention further comprises sequencing target regions by means of single-molecule sequencing, next generation sequencing, partial sequencing, or fragment mapping, more preferably by means of single-molecule sequencing as described in WO 2011/147931 or WO 2011/147929. According to a preferred embodiment of the invention, the method may further comprise detecting the binding of a protein to a specific nucleic acid sequence or site. A variety of methods for detecting protein binding are available to the skilled person. The method of the invention is particularly well-suited for generating hairpins for use in protein binding methods using single-molecules, such as that described in WO 2014/114687. The isolated target region may further be used as a substrate for detecting protein binding to nucleic acid, for example, as a substrate for detecting epigenetic modifications. Isolated target regions may be used, for example, in bisulfite conversion, high resolution melt analysis, immunoprecipitation (e.g. ChIP, enChIP), microarray hybridization, and other analyses of nucleic acid/protein interactions well-known to the skilled person. The term "epigenetic modifications," as used herein refers to modifications of the bases constituting a nucleic acid molecule which take place after the synthesis of said nucleic acid molecule. As a non-limiting example, a base modification may result from damage to said base. Epigenetic modifications include, for example, inter alia, 3-methylcytosine (3mC), 4-methylcytosine (4mC), 5-methylcytosine (5mC), 5-hydroxymethylcytosine (5hmC), 5-formylcytosine (5fC) and 5-carboxylcytosine (5caC), as well as 6-methyladenosine (m6A) in DNA, 5-hydroxymethyluracil (5hmU) and pseudo-uridine in RNA, and 3-methyl cytosine (3mC) and N6-methyladenosine (m6A) in DNA and RNA.

Likewise, the method may further comprise the detection of modified bases resulting from nucleic acid damage, such as DNA damage. DNA damage occurs constantly because of chemicals (i.e. intercalating agents), radiation and other mutagens may be performed on the isolated nucleic acid. DNA base modifications resulting from these types of DNA damage are wide-spread and play important roles in affecting physiological states and disease phenotypes. Examples include 8-oxoguanine, 8-oxoadenine (oxidative damage; aging, Alzheimer's, Parkinson's), 1-methyladenine, 6-O-methylguanine (alkylation; gliomas and colorectal carcinomas), benzo[a]pyrene diol epoxide (BPDE), pyrimidine dimers (adduct formation; smoking, industrial chemical exposure, UV light exposure; lung and skin cancer), and 5-hydroxycytosine, 5-hydroxyuracil, 5-hydroxymethyluracil, and thymine glycol (ionizing radiation damage; chronic inflammatory diseases, prostate, breast and colorectal cancer).

Preferably, the method of the invention further comprises detecting the binding of a protein to a specific nucleic acid sequence as described in WO 2014/114687.

Kit

A further object of the present invention is a kit that can be used for nucleic acid isolation according to any of the methods or embodiments of the invention described herein. The kit will provide the materials and methods for nucleic acid isolation and enrichment according to the invention as described previously herein. As such, the kit will include materials necessary for nucleic acid isolation according to the methods described herein. Contents may vary according to the Class 2 Type V Cas protein to be used (e.g. Cas12a, C2c1), the nucleic acid region(s) targeted, the method of capture, etc. according to any of the modalities described herein.

According to a particular embodiment, the kit of the present invention comprises:
a) a Class 2 Type V Cas protein, preferably catalytically active Cas12a
b) at least one gRNA, said gRNA being complementary to a site adjacent to a nucleic acid target region,
c) at least one 3' to 5' single-stranded enzyme having exonuclease activity, preferably exonuclease I,
d) an oligonucleotide probe,
e) optionally, at least one protease, and
f) optionally, a notice of use.

According to a further embodiment, said kit comprises EDTA, preferably a solution of EDTA, in place of or in addition to the at least one protease.

In some cases, the kit may further comprise a Class 2 Cas protein, preferably a second Class 2 Type V Cas protein. Preferably, the kit comprises at least two gRNAs, more preferably at least three, four, five, six, 10 gRNAs, each of said gRNAs being complementary to a specific nucleic acid region.

According to a particular embodiment, said kit comprises two gRNAs per target region, wherein said gRNAs are complementary to first and second sites, said sites being located on either side of a target region, as described above. The use of two Class 2 Type V Cas protein-gRNA complexes is advantageous as 5' overhangs may thus be generated on either side of a target region.

In cases where downstream multiplex analyses are desired, the kit may comprise two or more gRNAs, each gRNA being at least partially complementary to a site adjacent to a different target region. According to a particular embodiment, said kit comprises a Class 2 Type V Cas protein and a Class 2 Type II Cas protein, more preferably Cas9, with the corresponding appropriate gRNAs that are at least partially complementary to a first and second site, respectively, said sites being located on either side of a target region. Alternatively, two gRNAs of said Class 2 Type V Cas protein may recognize two different sites, said sites being located on either side of a target region as described herein. In some cases, the kit comprises one or more Cas proteins as described herein which have been preloaded with gRNA, thereby forming one or more Cas protein-gRNA complexes, preferably forming one or more Class 2 Type V Cas protein-gRNA complexes. According to a particular embodiment, when the kit comprises multiple Class 2 Type V Cas protein-gRNA complexes, said complexes are preferably mixed together in a single container. Preferably, the ratio of each Cas protein-gRNA complex comprised in said kit has been predetermined for ease of use.

Preferably, the guide segment of the gRNA is complementary to a region adjacent to a target region that is of interest in clinical diagnostics or genetic risk assessment. As an example, said gRNA is complementary to a site adjacent to the non-coding target region located downstream of the coding region of septin 9 (SEPT9) or epidermal growth factor receptor (EGFR). Indeed, the epigenetic status of these regions is known to be important for cancer outcome. As another example, said gRNA is complementary to a site adjacent to the region downstream of the gene FMR1, which is involved in Fragile X syndrome. An expansion in the number of copies of a 5'-CGG-3' repeat in this gene is responsible for disease. The epigenetic status of the region upstream of this CpG island (e.g. methylation) is also known to be related to the clinical severity of the disease. As another example, said gRNA is complementary to a site adjacent to the DMPK gene. Indeed, an expansion in the number of 5' CTG-3' repeats in this gene is characteristic of myotonic dystrophy type 1. As a further example, said gRNA is complementary to a region located in a cfDNA molecule, thereby enabling isolation of an adjacent target region comprised in the cfDNA molecule. Indeed, isolation of specific cfDNA, such as cffDNA or ctDNA, is of particular interest in a wide variety of downstream applications including prenatal testing (see, for example, Gahan, *Int J Womens Health*. 2013, 5:177-186) and cancer diagnosis and/or monitoring (see, for example, Ghorbian and Ardekani, *Avicenna J Med Biotech*. 2012, 4 (1): 3-13). One or more target regions comprised within a cfDNA may advantageously be isolated directly from a biological sample (e.g. a plasma, serum, or urine sample).

The kit described herein preferably enables isolation of at least two different target regions. Indeed, the value of certain epigenetic cancer diagnostic tests has been shown to be improved by multiplexing, wherein the characteristics of the sequence or structure of two or more different target regions (e.g. methylation status) are analysed in a single test. As a non-limiting example, the kit provided herein enables isolation of target regions comprising or consisting of the human GSTP1, APC and/or RASSF1 genes or appropriate regions thereof that are subject to DNA methylation, according to any of the methods described herein. Said isolated target regions may then be subjected to downstream analysis of methylation status, for example according to the methods provided herein (e.g. as provided in WO 2014/114687). Such a kit is particularly advantageous in the determination of risk of a subject developing prostate cancer (Wojno et al., *American health & drug benefits*, 2014, 7 (3): 129), and is advantageous over existing kits which notably use bisulfite treatment of sample DNA followed by PCR. In contrast to the methods of the invention, nucleic acids isolated with existing kits may notably be prone to false positive and false negative signals, as well as sample loss due to the harsh and inefficient chemical treatment.

According to a particular embodiment, the kit comprises two gRNAs per target region, said gRNAs being complementary to sites on either side of human gene(s) GSTP1, APC and RASSF1 as defined herein.

As another non-limiting example, the kit of the present invention enables isolation of at least one of the following target regions located within the human genome at the following positions: 65676359-65676418 on chromosome 17, 21958446-21958585 on chromosome 9, 336844-336903 on chromosome 6, 33319507-33319636 on chromosome 21, 166502151-166502220 on chromosome 6, 896902-897031 on chromosome 18, 32747873-32748022 on chromosome 5, 27949195-27949264 on chromosome 6, 27191603-27191672 on chromosome 7, 170170302-170170361 on chromosome 16 30797737-30797876 on chromosome 15, 7936767-7936866 on chromosome 1, 170077565-170077634 on chromosome 1, 1727592-1727661 on chromosome 2, 72919092-72919231 on chromosome 8, preferably of all 15 target regions. Isolation of said target regions is advantageous as downstream analyses of DNA methylation status of said target regions may be used to detect bladder cancer. Existing kits use methylation sensitive restriction enzymes followed by PCR to identify methylated sequences, and may therefore be limited by the presence of the appropriate restriction sites in the target regions, complicating test design, and limiting sensitivity. Thus, an improved kit for the isolation and detection of bladder cancer may preferably comprise two gRNAs that are at least partially complementary to sequences flanking the target region and two additional gRNAs that are at least partially complementary to sequences located at the extremities of said target region for isolation of each of these 15 target regions according to the methods described herein, preferably for isolation of all 15 target regions.

As a non-limiting example, the target region may comprise a specific sequence, a specific number of sequence repeats, one or more nucleotide base modifications, or not. As a further non-limiting example, the region targeted for isolation may be a specific length or a length that differs from said specific length. Preferably, the kit of the invention further comprises at least one restriction enzyme, and/or an RNase. Preferably, the kit further comprises a suitable Class 2 Type V Cas protein reaction buffer and a suitable Class 2 Type II Cas protein reaction buffer, such as those detailed in the examples below.

The kit may further comprise additional elements, as is appropriate for a given application. For example, the kit may further comprise one or more hairpin adaptors or site-specific endonucleases, ligase and/or polymerase enzymes, oligonucleotides, dNTPs, appropriate buffers, and the like. According to a particular embodiment, said kit further comprises a ligase and/or a 5' flap endonuclease, preferably FEN1.

Additional features and advantageous aspects of the present invention are illustrated in the figures and examples below.

FIGURE LEGENDS

Figure 1B:
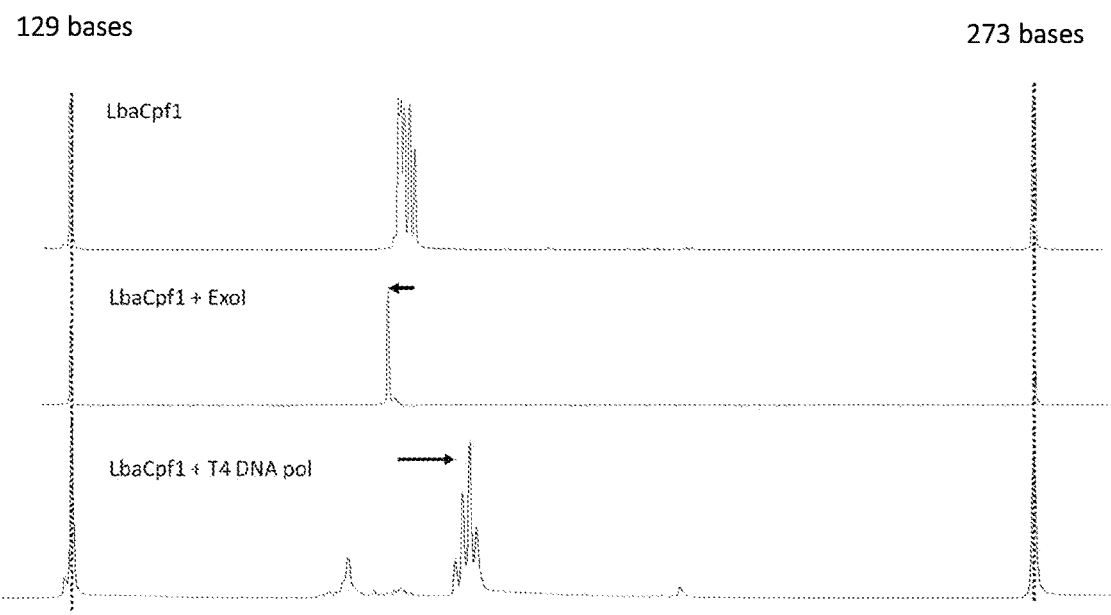
Figure 1C:
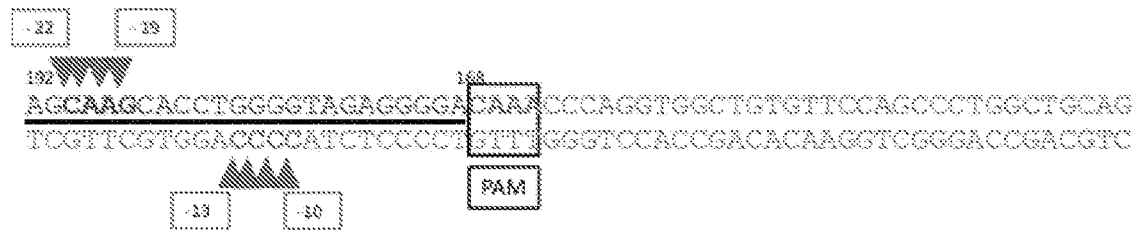
Figure 1C:
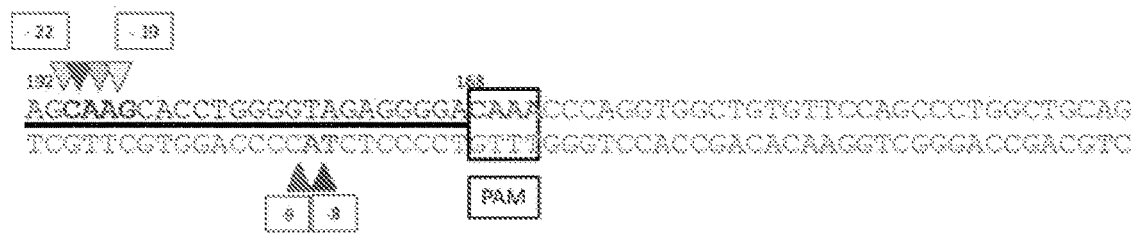

FIG. 1A-C. Addition of ExoI to a population of molecules bound by a Cas12a-gRNA complex creates a longer 5' overhang with less variability in the cleavage site. (1A) A fragment containing the target sequence for the SEPT9.2 crRNA #1 (SEQ ID NO: 2) guide was amplified by PCR (SEQ ID NO: 3) with the primer PS1462 and PS1464, a primer tagged with FITC fluorescent at its 5' end (SEQ ID NOs: 4 and 5, respectively). The fragment was then either incubated with the Cas12a-gRNA complex alone, to determine the cleavage position on the non-target strand (left), with the Cas12a-gRNA complex simultaneously with ExoI to determine the number of recessed bases at the 3' end by the ExoI treatment (center), or with the Cas12a-gRNA complex followed by fill-in with T4 DNA polymerase to determine the cleavage position on the strand hybridized with the gRNA (right). (1B) Representative traces of the results obtained by capillary electrophoresis of the three experimental settings described in (1A) allowed us to determine the position of the 3' end of the non-hybridized strand at single-base resolution as well as the cleavage position within the 5' hybridized strand. Each reaction was spiked-in with PCR fragments of known size (129, 273 and 503 bp) tagged with FITC (corresponding to SEQ ID NO: 6 to 8), which were used as markers. The traces from the three different experiments were aligned according to the 129 and 273 bp peaks as shown. The arrow pointing toward left in the middle panel indicates that the fragment is shortened by the addition of ExoI (therefore migrating closer to the lower marker, at 129 bases). The arrow pointing right in the bottom panel indicates that the 5' overhang was filled-in by the T4 DNA polymerase (therefore migrating closer to the upper marker, at 273 bp) (1C) Cleavage position determined for the SEPT9.2 crRNA #1 complexed with LbaCas12a (NEB) based on experimental settings presented in (1A). The positions indicated in the figure are provided relative to the first base of the gRNA sequence (underlined) starting from the first base adjacent to the PAM site.

Figure 2:
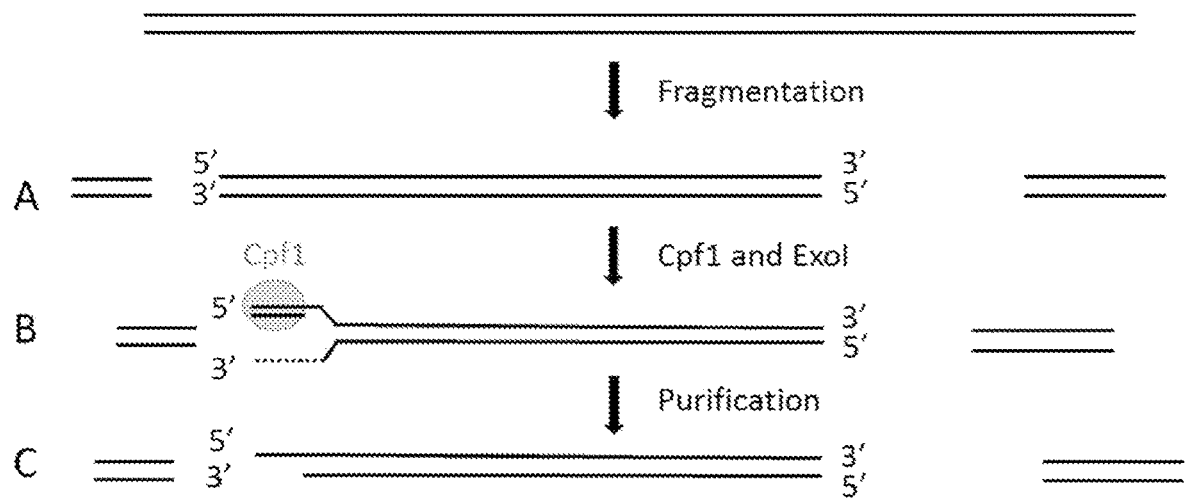

FIG. 2: Schematic representation of steps a) to c) of the method of the invention using a single Cas12a-gRNA complex. (A) The population of nucleic acid molecules may optionally be mechanically or enzymatically fragmented to generate random fragments. (B) Following fragmentation, the population of nucleic acid molecules is contacted with a Cas12a-gRNA complex comprising a guide segment that is at least partially complementary to a site that is located adjacent to a target region. During the incubation, any single-stranded regions are targeted for digestion by ExoI treatment. (C) The Cas12a-gRNA complex is then removed (referred to as "purification" in the figure). The resulting fragments contain a longer and better defined 5' overhang, which may then be subjected to steps d) and e) of the method of the invention (not shown here).

Figure 3:
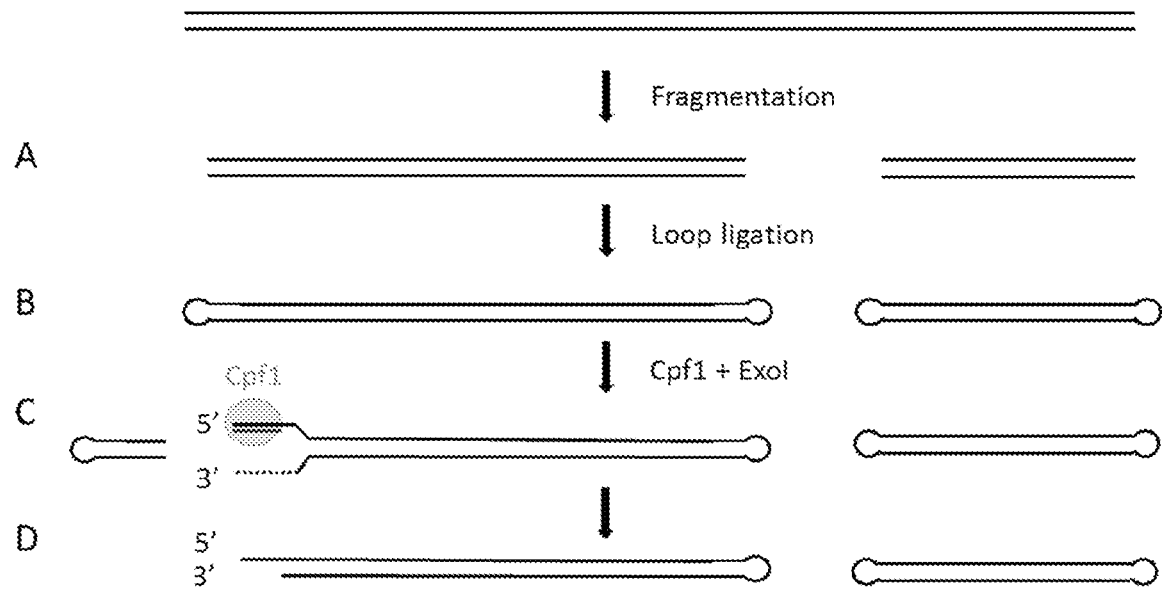

FIG. 3: Schematic representation of steps a) to c) of the method of the invention with an alternative strategy, using a Cas12a-gRNA complex and a hairpin adaptor. Following optional first steps of fragmentation and end-repair (A), a hairpin (or other) adaptor may be ligated to all of the free ends, for example using T/A cloning (B). (C) Following fragmentation, the population of nucleic acid molecules is contacted with a Cas12a-gRNA complex comprising a guide segment that is at least partially complementary to a site that is located adjacent to a target region. During incubation, any single-stranded regions are targeted for digestion by ExoI treatment. Only the sites containing the complementary sequence to the gRNA will be targeted by this treatment and therefore only these sites will comprise a single stranded 5' overhang. (D) The Cas12a-gRNA complex is then removed. The resulting population of nucleic acid molecules, comprising the 5' single-stranded overhang, can then subjected to steps d) and e) of the method of the invention (not shown here), thereby isolating the nucleic acid target region.

Figure 4:
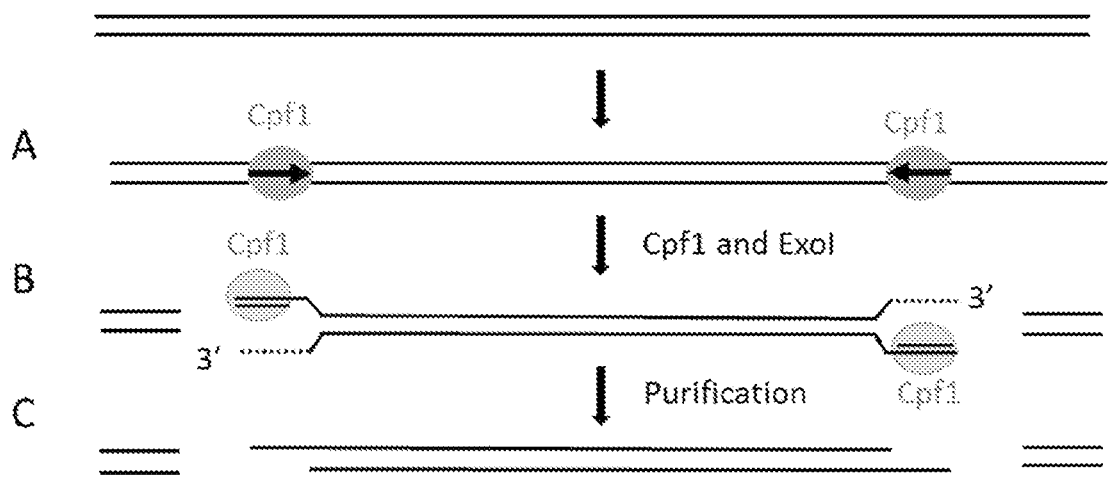

FIG. 4: Schematic representation of steps a) to c) of the method of the invention with an alternative strategy, using two Cas 12a-gRNA complexes. (A) Illustration of the sites recognized by the gRNA of the Cas12a-gRNA complexes, with the gRNA designed such that the PAM sequence is located immediately adjacent to a target region, as illustrated by the arrow pointing inwards. (B) Two Cas12a-gRNA complexes targeting a first and second site flanking the targeted region on its first and second sides, respectively, can be used simultaneously with ExoI treatment to create 5' overhangs on both sides of the target region to be isolated. Fragmentation is not illustrated here as this step is optional. (C) The Cas12a-gRNA complexes are then removed. The resulting population of nucleic acid molecules, comprising the 5' overhangs, can then be subjected to steps d) and e) of the method of the invention (not shown here), thereby isolating the nucleic acid target region, which may then be used in downstream applications, such as but not limited to cloning, library preparation or hairpin production.

FIG. 5: The target region(s) can be isolated using two oligonucleotide probes located on either side of said target region(s). (A) to (C) are performed as described in the legend of FIG. 4. (D) After treatment with Cas12a and ExoI, the population of nucleic acid molecules is contacted with synthetic oligonucleotide probes containing various ligands (for example, but not limited to, biotin and digoxygenin), which are complementary at their 5' end to the site that is at least partially complementary to the Cas12a gRNA. The 5' flap of the oligonucleotide probes are removed using the FEN1 endonuclease enzyme and the resulting nick is sealed with a ligase. This allows for the covalent attachment of oligonucleotide probes at each end of the molecule. (E) The target region can then be isolated as described herein. (F) The step of isolation may be repeated using the second ligand. This advantageously increases the specificity of the method. (G) The resulting molecule can be used for downstream applications, such as hairpin or library production.

FIG. 6: Schematic representation of the method used to produce molecules suitable for the SIMDEQ instrument (hairpin structure) from E. coli genomic DNA. (A) Illustration of the sites recognized by the gRNA of the Cas12a-gRNA complexes, with the gRNA designed such that the PAM sequence is located adjacent to a target region, as illustrated by the arrow pointing inwards. (B) The regions of interest (targets #1 and 2, SEQ ID NOs: 9 and 10) were flanked on either side by two different Cas12a-crRNA complexes (SEQ ID NOs: 11 to 14), said complexes binding to a first and second site, respectively. A 3' to 5' single-stranded exonuclease was added simultaneously. 5' overhangs were thereby generated on either side of the target region. (C) The Cas12a-gRNA complexes are then removed (referred to as "purification" in the figure). Salts and any other proteins are also preferably removed. (D) Oligonucleotide probes PS1466 and PS1468 (SEQ ID NOS: 15 and 16), which contain the necessary sequence to allow hybridization to a support (thus referred to as surface oligonucleotides), have a sequence corresponding to the Cas12a crRNA sequence at their 5' end (they are therefore complementary to the 5' overhang adjacent to the target region). The reaction containing these oligonucleotides was supplemented with FEN1 and Taq DNA ligase to remove the 5' flap region of the oligonucleotide and seal the nick generated by the digestion of the 5' flap. (E) A second oligonucleotide (containing a biotin at its 5' end (illustrated by the square)), with a sequence complementary to a single-stranded region of the oligonucleotide probe, was added to the reaction tube. Said second oligonucleotides are PS1467 and PS1469 (SEQ ID NO: 17 and 18 for targets #1 and 2, respectively). The gap between the second oligonucleotide and the duplex was filled-in by DNA polymerase and ligated. (F) The resulting fragments were digested with BsaI and a synthetic hairpin was ligated on the other side of the target region. In some cases, step F may be performed as the first step of the method (i.e. prior to generating the 5' overhang with the Cas12a-gRNA complex and ExoI). The desired molecules were then isolated from the population of nucleic acid molecules using streptavidin beads and loaded on the SIMDEQ platform. Typical fingerprinting traces of the hairpins generated by this method are presented in FIGS. 10A and 10B.

Figure 7:
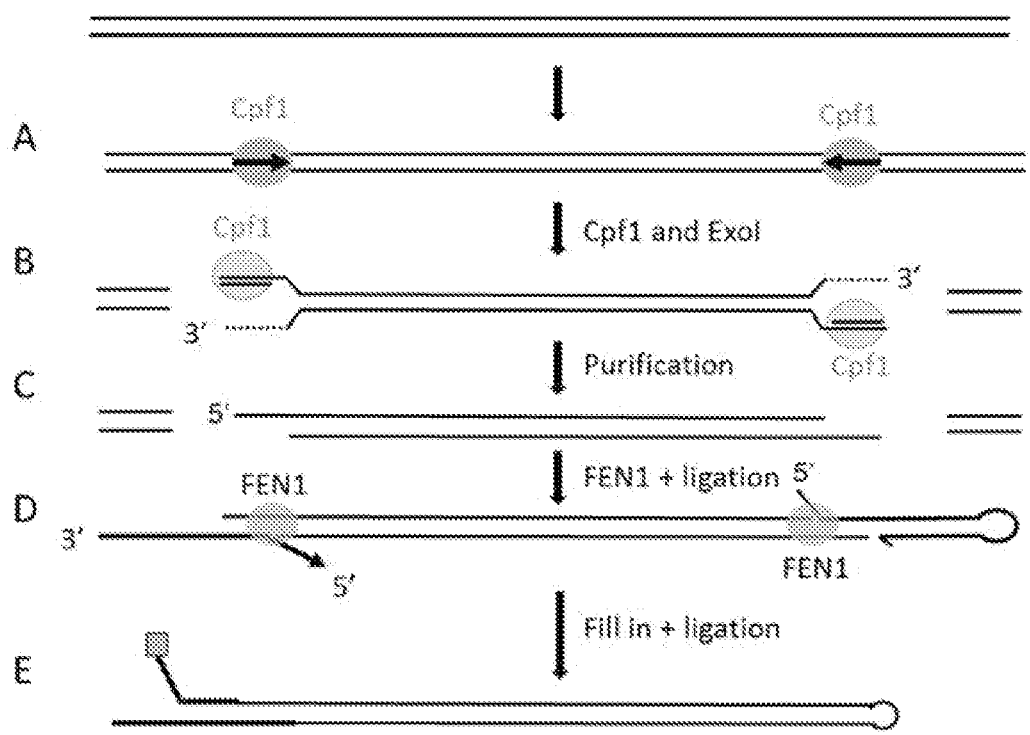

FIG. 7: Alternative schematic representation of the method used to produce molecules (E) suitable for the SIMDEQ instrument (hairpin structure) from E. coli genomic DNA. (A) to (C) The same approach is used as that illustrated in FIG. 6. In (D), in addition to contacting the population of nucleic acid molecules with the oligonucleotide probe, a hairpin is ligated to the second site. In both cases, any 5' flaps may be removed by FEN1, and the remaining nick sealed by ligation. This is advantageous as both sites present on either side of the target region can be processed at the same time, therefore reducing the duration of the method.

Figure 8:
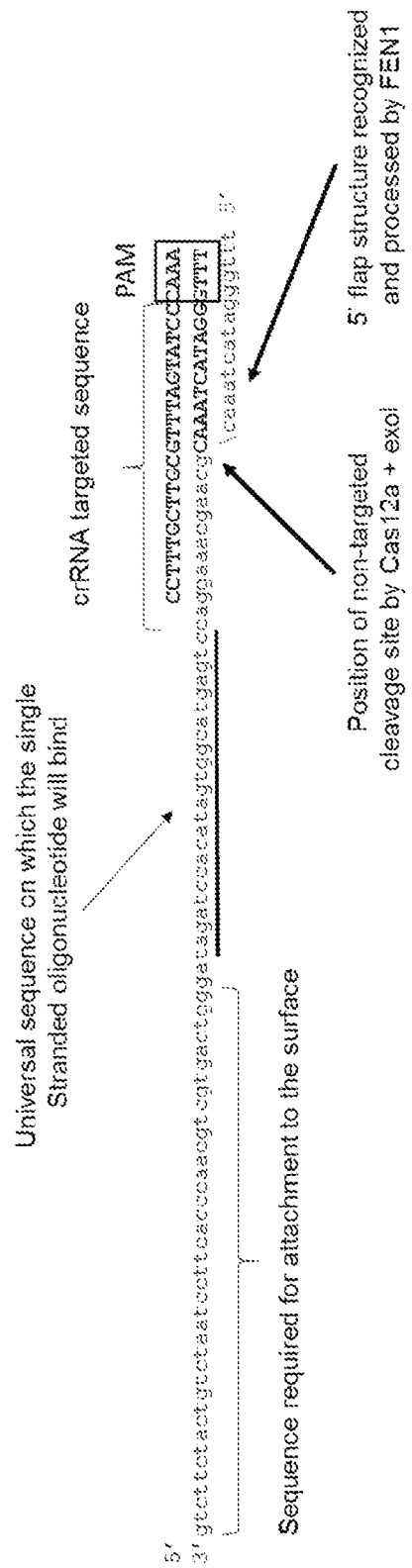

FIG. 8: Exemplary structure of the oligonucleotide probe used in the present invention. The sequence targeted by the gRNA is shown in bold and capital letters. The 5' end of the oligonucleotide probe contains a sequence that it at least partially complementary to the sequence targeted by the gRNA, which corresponds to the 5' overhang. The sequence may be extended up to the PAM sequence to account for variability in the cleavage position of Cas12a-gRNA on the non-targeted strand. Any flap structure may be removed by processing with FEN1. The single-stranded region of the probe contains a "universal" sequence to which a single-stranded oligonucleotide (e.g. biotin oligonucleotide of FIG. 6(E) required for hairpin production) may bind. Optionally, the oligonucleotide probe may further comprise a specific sequence for anchoring the probe (and therefore the target region) to a solid support, such as the surface of a flow cell. In some cases, the "universal" sequence may be comprised in the loop region of a hairpin molecule.

Figure 9:
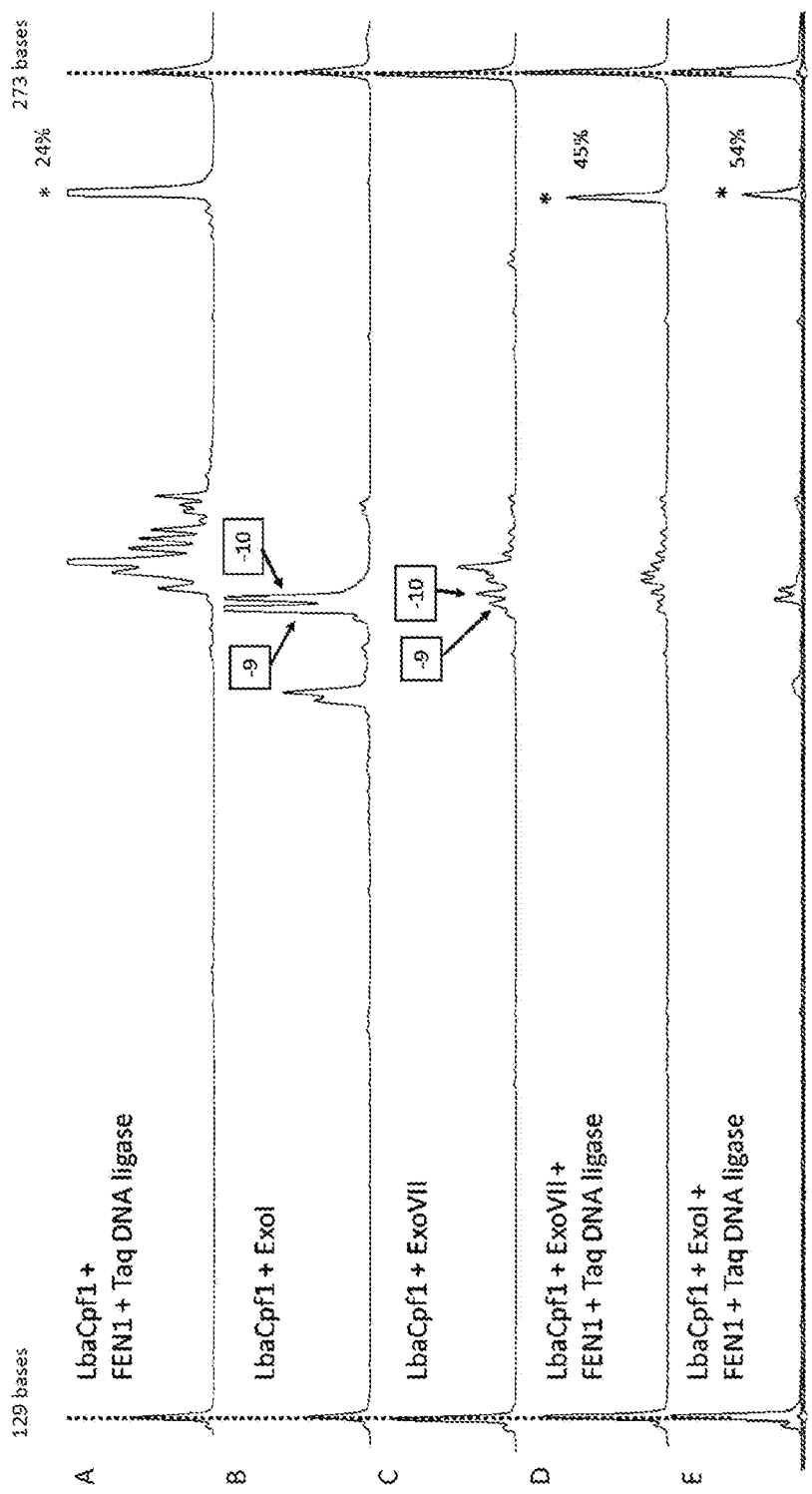

FIG. 9: The 5' overhang resulting from Cas12a-gRNA and ExoI treatment is capable of promoting hybridization of an oligonucleotide probe. A 287 bp PCR fragment (SEQ ID NO: 19) containing the site recognized by the human NDGR4.1 crRNA #1 (SEQ ID NO: 20) was tagged with FITC at the 5' end of the non-target strand containing the 5'-TTTV-3' PAM sequence and analyzed by capillary electrophoresis after incubation in the following conditions. The fragment was incubated with (A) LbaCas12a crRNA #1 in presence of FEN1 and Taq DNA ligase, (B) LbaCas12a crRNA #1 and ExoI, (C) LbaCas12a crRNA #1 and ExoVII, (D) LbaCas12a crRNA #1 and ExoVII in presence of FEN1 and Taq DNA ligase, or (E) LbaCas12a crRNA #1 and ExoI in presence of FEN1 and Taq DNA ligase. In all cases, an oligonucleotide probe comprising a biotin ligand that can be processed by FEN1 and ligated to the target site by Taq DNA ligase was also present. The ligated product will increase the size of the fragment (marked by a star) (SEQ ID NO: 21) causing the peak to be located closer to the 273 bp marker. The same FITC markers used in FIG. 1B were also spiked-in, and used to align the traces. In particular, the traces were aligned based on the 129 and 273 bp fragments.

Figure 10:
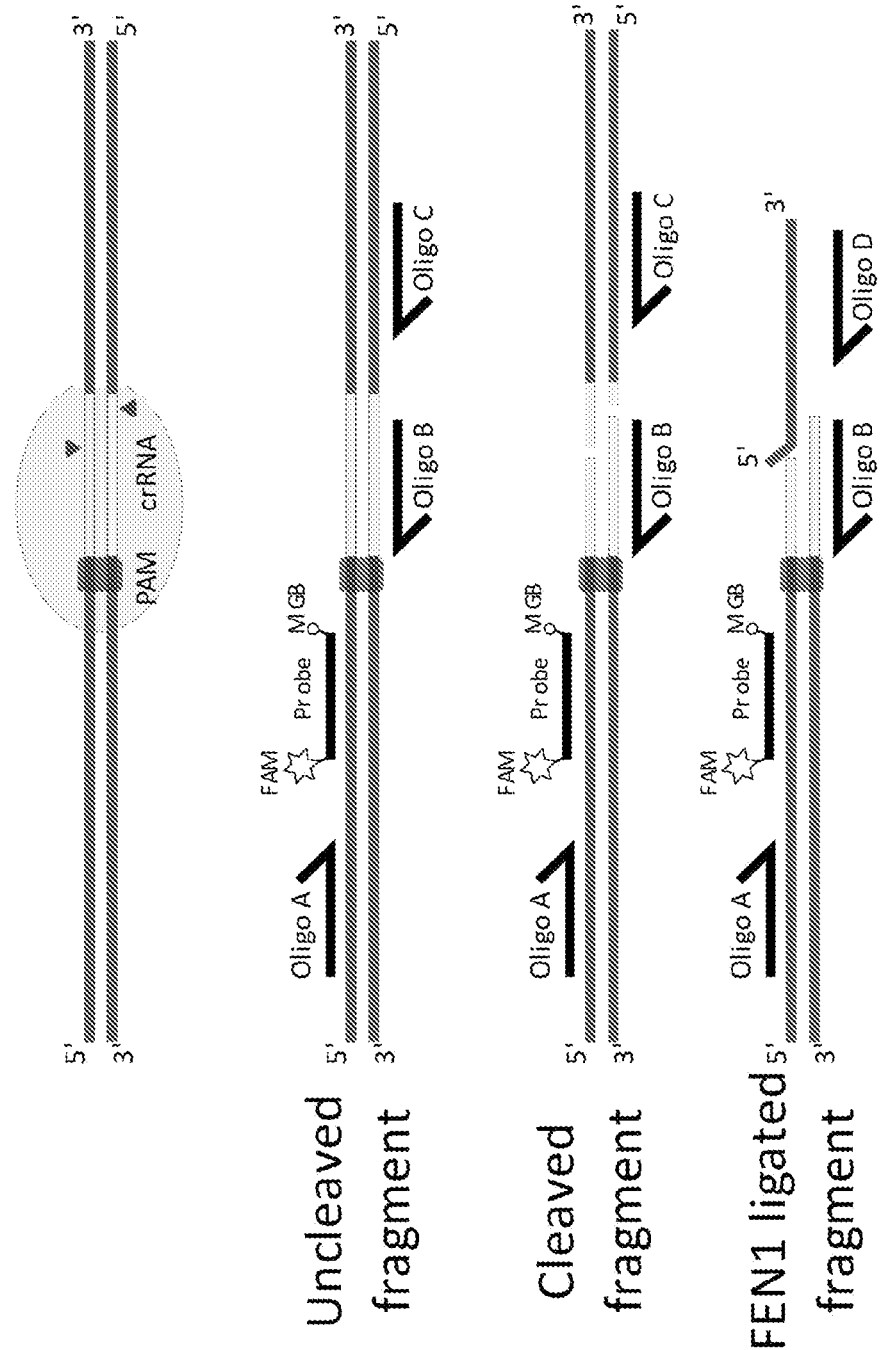

FIG. 10. Schematic representation of the qPCR quantification assay developed to determine the efficiency of cleavage of Cas12a-gRNA and ligation of the oligonucleotide probe using FEN1 and ligase. Three different sets of primers (A/B, A/C and A/D, SEQ ID NOs: 94-97) were designed in proximity to the Cas12a-crRNA #2 cleavage site of FMR1 (SEQ ID NO: 29) as illustrated. A TaqMan probe (SEQ ID NO: 93), which can be used with any of the three qPCR reactions, was designed to allow the quantification of cleavage efficiency as well as attachment of the oligonucleotide probe to genomic DNA. The product obtained with primers A and B, which amplify a fragment regardless of whether Cas12a-crRNA #2 has cleaved the nucleic acid molecule or not, were used to normalize each reaction (also referred to as "total amount"). To quantify Cas12a cleavage efficiency, we designed a second primer, C, that is located outside of the targeted region to be enriched. Therefore, when Cas12a-crRNA #2 complex cleaves its target, the fragment can no longer serve as a template for amplification, leading to a decrease in amplifiable starting material. To estimate the rate of cleavage, we calculated the ratio of fragments remaining after incubation with the Cas12a-crRNA #2 complex and divided this number by the calculated "total amount". This provides the amount of uncleaved fragment and can be transformed into the amount of cleaved fragment by taking the inverse fraction (i.e. 100—the amount of uncleaved fragment=amount of cleaved fragment). Finally, to quantify the efficiency of oligonucleotide probe ligation to the FMR1 fragment, primers A and D, which amplify a fragment specific for the ligated oligonucleotide, were used. The fraction obtained with primers A/D is also referred to as "FEN1 ligation".

Figure 11:
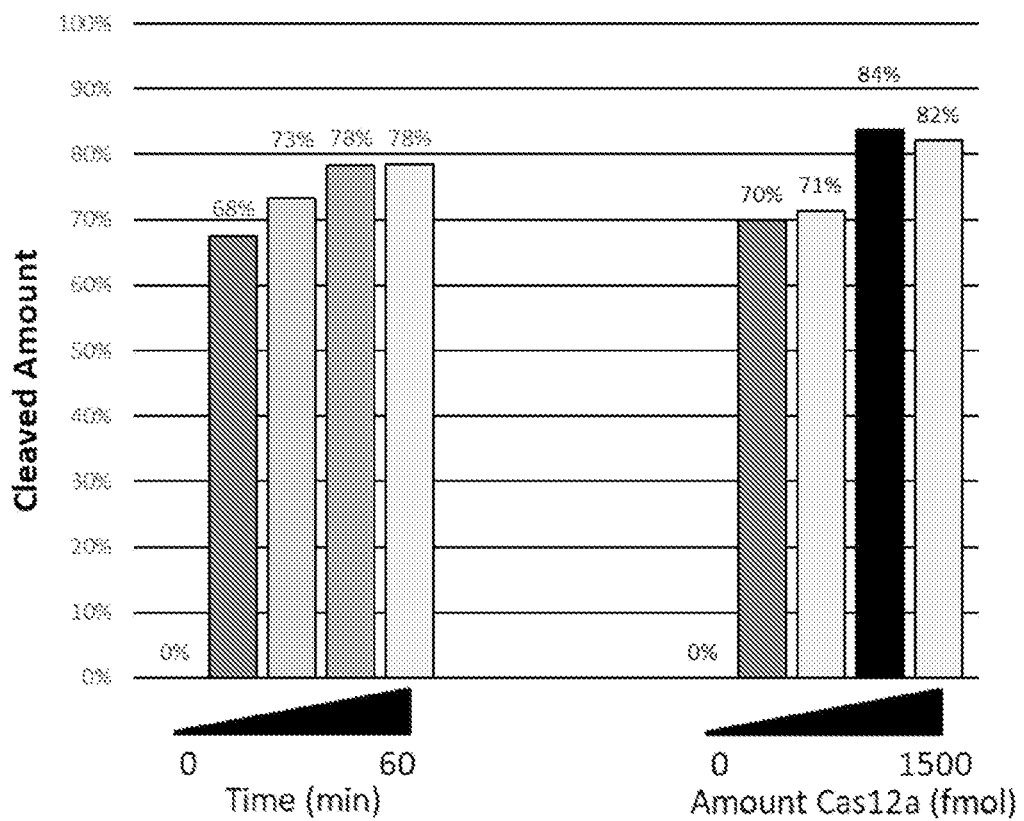

FIG. 11. Cleavage efficiency of the Cas12a-gRNA complex varies with reaction time and concentration. To determine cleavage efficiency of the Cas12-crRNA #2 complex as a function of reaction time, 2 μg of human genomic DNA was incubated in NEB2.1 buffer supplemented with 10 mM DTT, and 600 fmol of Cas12a-crRNA #2 gRNA specific to FMR1 (SEQ ID NO: 29) at 37° C. for 10, 20, 30 and 60 min (left panel). qPCR was performed using two sets of primers (A/B and A/C, respectively SEQ ID NO: 94-95 and 94-96) with the Taqman probe (SEQ ID NO: 93). A control reaction without the presence of the Cas12a-crRNA #2 complex was performed and used as an uncleaved reference. Relative quantification of cleaved fragment (primer set A/C) was normalized by the "total amount" of material (primer set A/B; see also the legend of FIG. 10) and then normalized by the uncleaved reference. 78% cleavage of the target was achieved when reaction time was increased from 10 min to 30 min. Cleavage efficiency when the Cas12a-crRNA #2 complex was incubated for 10 minutes (at 68%) was also evaluated by increasing the amount of complex. 2 μg of human genomic DNA was incubated in NEB2.1 buffer supplemented with 10 mM DTT with either 300, 600, 1200, 1500 fmol of Cas12a-crRNA #2 guide RNA specific to FMR1 (SEQ ID NO: 29) at 37° C. for 10 min (right panel). The amount of cleaved target was increased up to 84% by doubling the amount of Cas12a-crRNA #2 complex from 600 to 1200 fmol.

Figure 12A:
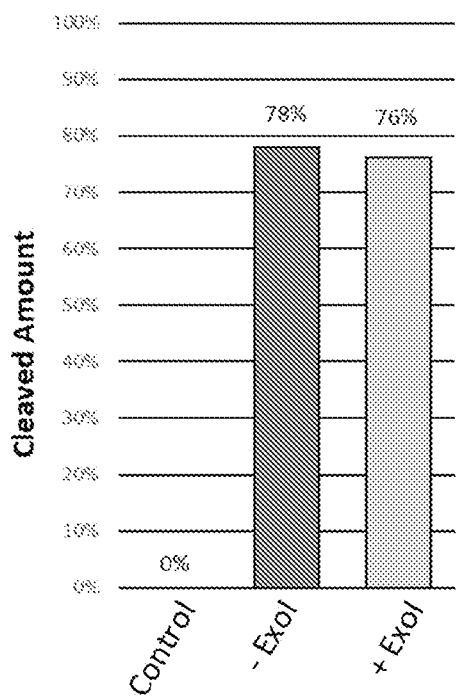
Figure 12B:
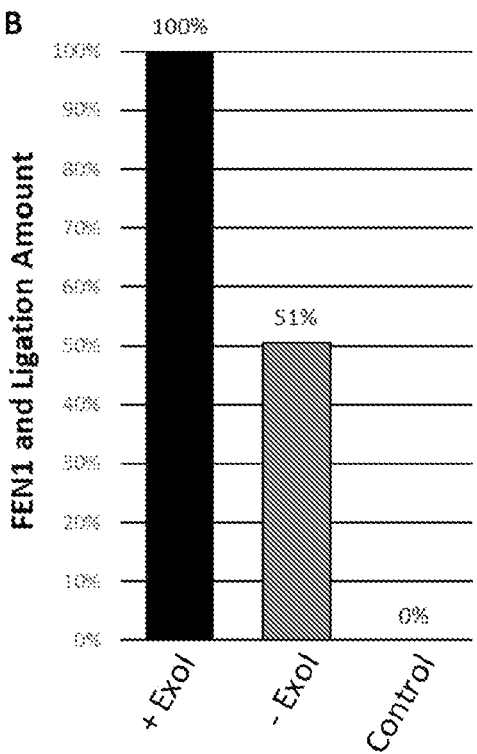

FIG. 12A-B. Addition of Exonuclease I does not influence Cas 12a-gRNA cleavage but improves probe ligation with FEN1. (A). 2 μg of human genomic DNA were incubated in NEB2.1 Buffer supplemented with 10 mM DTT, with 600 fmol of Cas12a-crRNA #2 gRNA specific to FMR1 (SEQ ID NO: 29) for 30 min at 37° C. with or without Exonuclease I to increase the number of recessed bases at the 3' end. qPCR was performed by using two sets of primers (A/B and A/C, respectively SEQ ID NOs: 94/95 and 94/96) with the Taqman probe (SEQ ID NO: 93). A control reaction without the presence of the Cas12a-crRNA #2 complex was used as an uncleaved reference. Relative quantification of the cleaved fragment (primer set A/C) was normalized by the "total amount" of material (primer set A/B) and then normalized by the uncleaved reference. The presence of Exonuclease I does not impact cleavage with Cas12a-crRNA #2; 78% and 76% of the DNA was cleaved respectively in the presence or absence of Exonuclease I, here. (B). The cleavage reactions performed using the Cas12a-crRNA #2 in presence or absence of Exonuclease I, as described in FIG. 12A, were incubated in ThermoPol Buffer supplemented with 1 mM NAD, 40 units of Taq DNA Ligase, 32 units of FEN1 and 10 pmol of the target specific oligonucleotide probe (SEQ ID NO:: 98) with 20 bases complementary to the site recognized by the crRNA and containing a known sequence used for qPCR. Reactions were incubated at 37° C. for 30 min. A control reaction without the presence of the Cas12a-crRNA #2 complex was used as an unligated fragment reference. Relative quantification of probe ligation fragment (primers A/D, SEQ ID NOs: 94/97) was normalized by the "total amount" of material (primers A/B, SEQ ID NOs: 94/95) and then normalized by the "standard reference reaction" (cleavage reaction with Cas12a-crRNA #2 in the presence of Exonuclease I and FEN1 at 37° C. for 30 min). When Exonuclease I was present, efficiency of FEN1 and probe ligation was increased two-fold.

Figure 13:
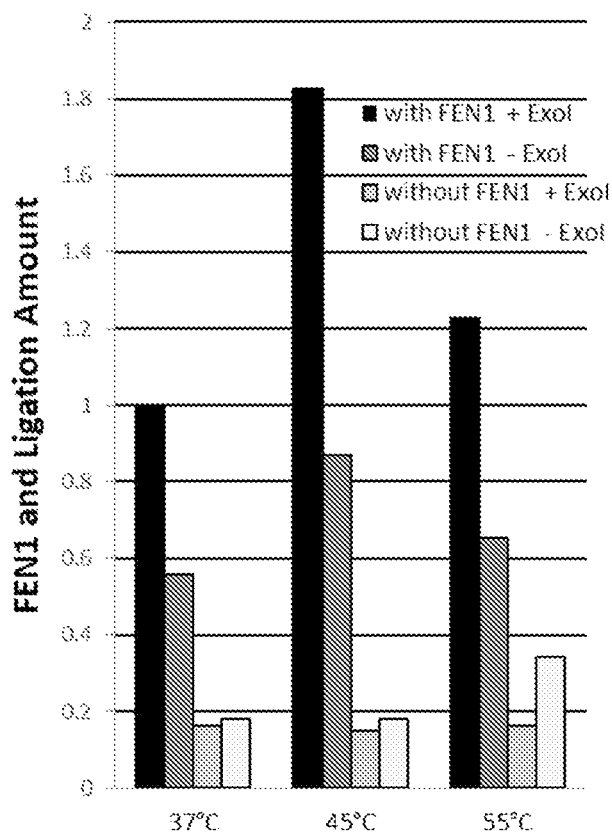

FIG. 13. Effect of the temperature on the efficiency of FEN1 processing and ligation of the oligonucleotide probe. 2 μg of human genomic DNA were incubated in NEB2.1 Buffer supplemented with 10 mM DTT, with 600 fmol of Cas12a-crRNA #2 gRNA specific for FMR1 (SEQ ID NO: 29) for 30 min at 37° C. with or without Exonuclease I in order to determine the effect of the increased length of the 5' single-stranded overhang on the efficiency of ligation of the target specific oligonucleotide probe. Cas12a-crRNA #2 cleavage reactions in the presence or absence of Exonuclease I were incubated in ThermoPol Buffer supplemented with 1 mM NAD, 40 units of Taq DNA Ligase, 32 units of FEN1 (or without FEN1) and 10 pmol of the oligonucleotide probe oligonucleotide (SEQ ID NO: 98) having 20 bases complementary to the site recognized by crRNA #2 and comprising a known sequence, which is used for qPCR reactions. Three incubation temperatures were tested to observe the efficiency of probe ligation at 37° C., 45° C. and 55° C. for 30 min. qPCR reactions were performed using two sets of primers (A/B and A/D, respectively SEQ ID NO:

94/95 and 94/97) with the Taqman probe (SEQ ID NO: 93). Relative quantification of probe ligation fragment (primer set A/D) was normalized by the "total amount" of material (primer set A/B) and quantification was then normalized by our "standard reference reaction" (Cas12a cleavage in presence of Exonuclease I and the FEN1 reaction at 37° C. for 30 min). For all temperatures tested, the presence of exonuclease I improves the ligation efficiency by 2-fold. Moreover, the efficiency of ligation and/or FEN1 activity was increased by 1.8-fold when reactions were incubated at 45° C. as compared to 37° C.

Figure 14:
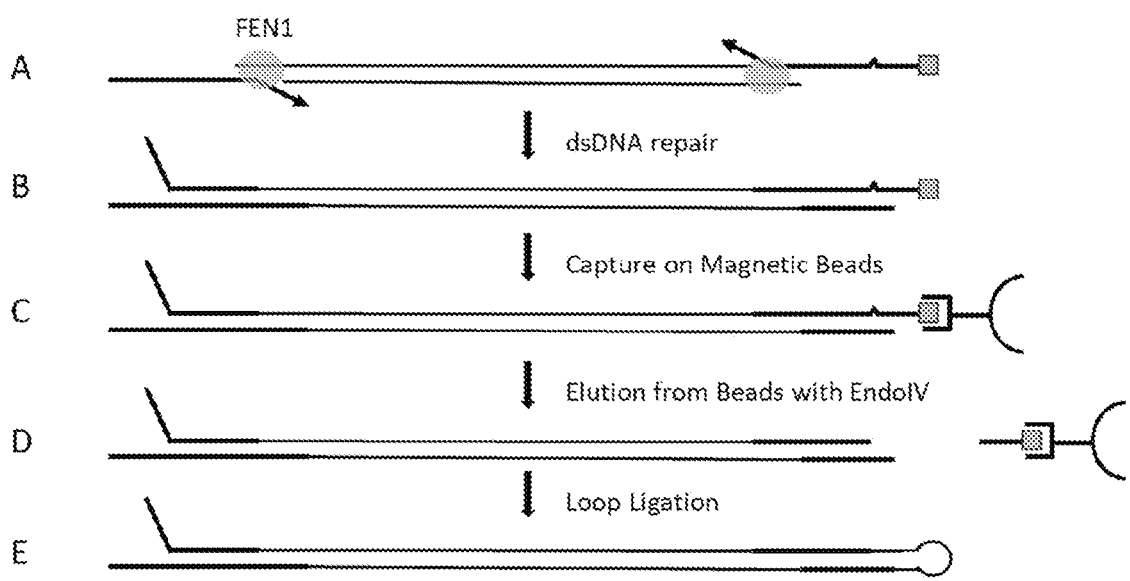

FIG. 14. Schematic representation of the method used to produce molecules suitable for the SIMDEQ instrument (hairpin structure) from human genomic DNA. (A) Oligonucleotide probes specific to crRNA #1 and crRNA #2 (SEQ ID NOS: 100 and 99) are shown. The first probe comprising the necessary sequence to allow hybridization to a support (thus referred to as the surface oligonucleotide), has a sequence corresponding to the Cas12a crRNA #1 sequence at its 5' end (shown on the left side of the image), while the second probe comprises a biotin at its 5' end (illustrated by the square) and an abasic site modification (illustrated by the triangle), has a sequence corresponding to the Cas12a crRNA #2 sequence at its 5' end, thereby forming a duplex. The reaction containing these oligonucleotides was supplemented with FEN1 and Taq DNA ligase to remove the 5' flap region of each oligonucleotide and seal the nicks generated by the digestion of the 5' flaps. (B) A second set of oligonucleotides (SEQ ID NOs: 101 and 97) complementary to the probes ligated by FEN1 and ligase in (A) were hybridized, and the DNA molecule was filled-in by DNA polymerase and ligated to generate a contiguous dsDNA molecule for the complete target region and create a Y-shaped structure on one end. (C) Duplexes were then isolated from the population of nucleic acid molecules using streptavidin beads. (D) Duplexes were eluted from beads using Endonuclease IV which catalyzes the cleavage of the DNA phosphodiester backbone at the abasic site with 3'-hydroxyl termini. A 4 bp overhang was generated at the 5' end of the oligonucleotide previously added to generate the dsDNA molecule in (B). (E) A synthetic hairpin (SEQ ID NO 102) was ligated to this 5' overhang. Duplexes were isolated using streptavidin beads coated with a specific linker (SEQ ID NOs: 103 and 104) and loaded on the SIMDEQ platform.

Figure 15A:
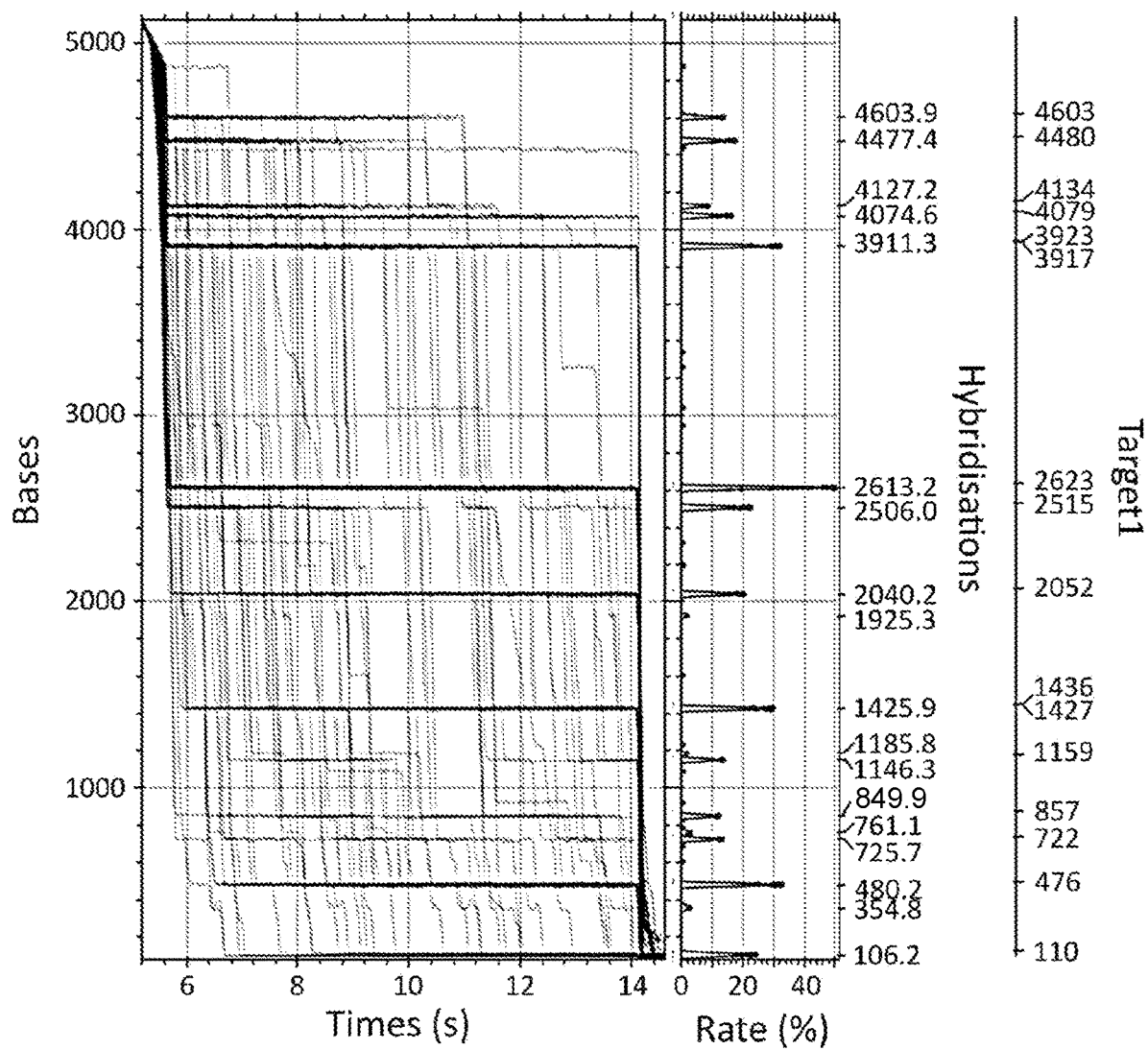
Figure 15B:
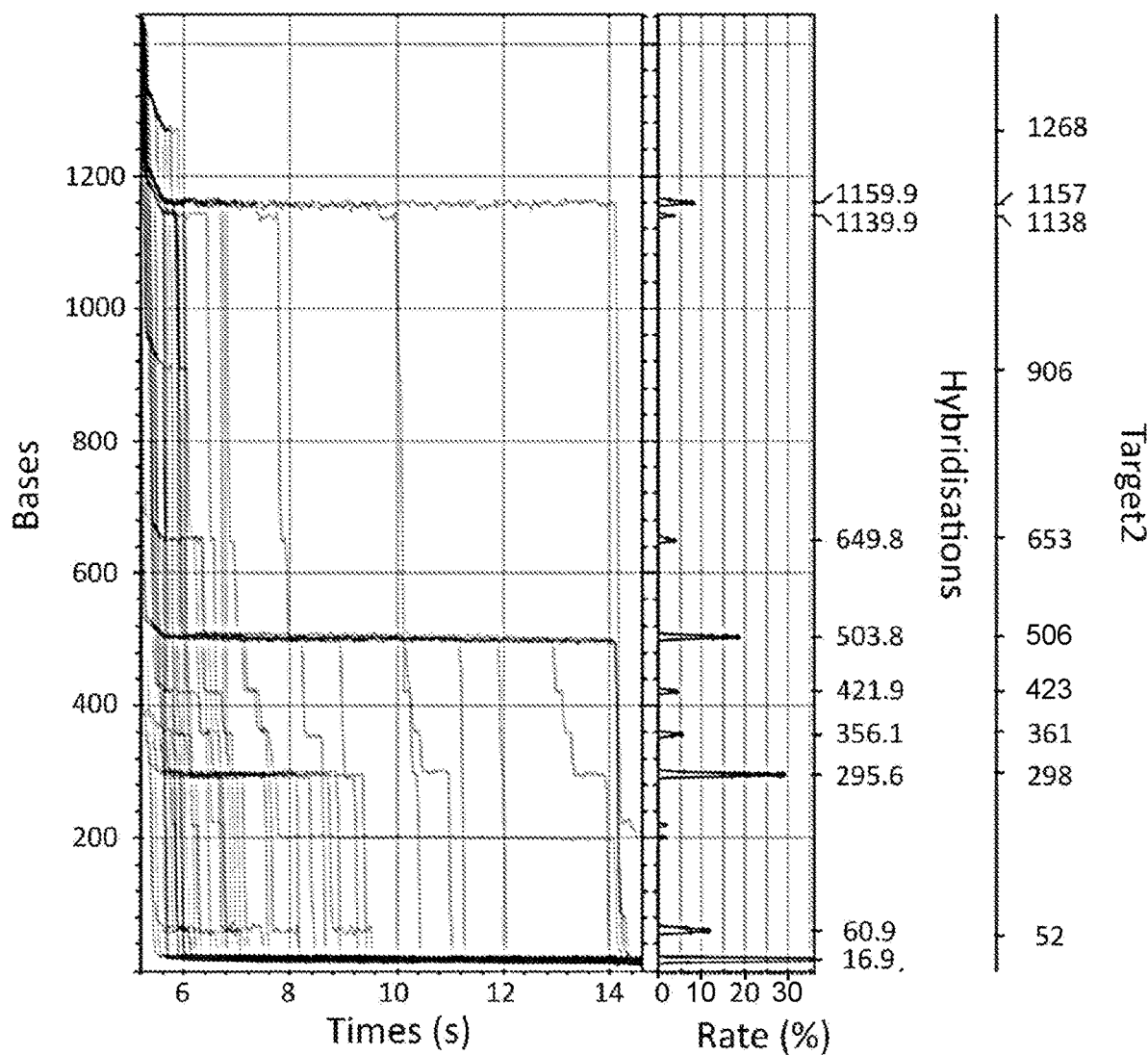

FIG. 15A-B. The method presented in FIG. 6 allowed for successful production of hairpin molecules containing the targeted regions. Trace for a four-base oligonucleotide (CAAG) fingerprint experiment after isolation of both target #1 (A) target #2 (B) from E. coli genomic DNA using the method presented in FIG. 6. All of the expected peaks were properly identified in both targets using the CAAG four-base oligonucleotide.

Figure 16B:
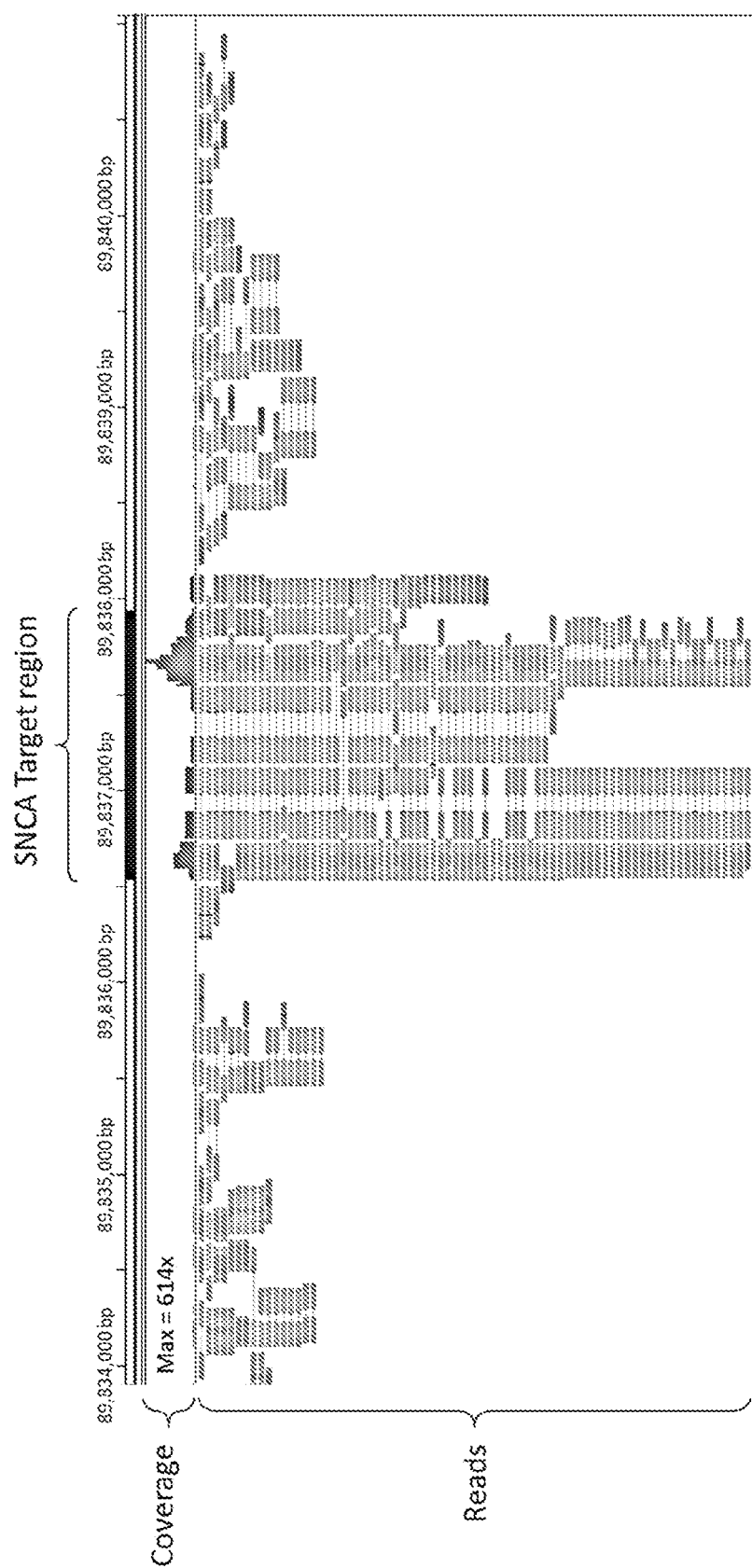

FIG. 16A-B. Exemplary results from Illumina sequencing performed on the library prepared from human genomic DNA against 15 different human targets using the method of the invention. (A) Target regions selected for enrichment with corresponding genomic coordinates. These regions were selected either due to the presence of epigenetic biomarkers or known loci with expanded repeats involved in human diseases. (B) Screenshot of the read alignment obtained from Illumina sequencing after target region enrichment using the method of the invention. Specifically, the library was generated using the method illustrated in FIG. 5, except that only one oligonucleotide probe comprising a ligand (in this case biotin) was used (step F was therefore not performed). The black box represents the region targeted for enrichment corresponding to the SNCA CpG island, chromosome 4: from 89,836,538 to 89,837,940 bp). Each mapped read is represented by a grey horizontal line. As illustrated in dark grey, the region shows high coverage (of up to 614× coverage) when compared to the surrounding regions (which show less than 1× coverage).

EXAMPLES

The following examples are included to demonstrate preferred embodiments of the invention. All subject-matter set forth or shown in the following examples and accompanying drawings is to be interpreted as illustrative and not in a limiting sense. The following examples include any alternatives, equivalents, and modifications that may be determined by a person skilled in the art.

Example 1: Methods of Selecting gRNAs

For all strategies described below, one or more guide RNAs are designed using available online tools. RNA guides can then either be synthesized in vitro using a viral transcriptional system (for example, 17, SP6 or T3 RNA polymerase, etc.) or be chemically produced using an automated synthesizer as a single crRNA guide which contains the sequence complementary to the target region. The efficiency of each gRNA is evaluated in vitro on a standardised/control sample (e.g. PCR fragments) using the wild type Cas nuclease to ensure that each Cas protein-gRNA complex will cleave with high efficiency (e.g. at least 80% of the initial PCR fragment is cleaved).

In the present example, Cas12a guide RNA(s) may be chemically produced using an automated synthesizer according to a common generic sequence (SEQ ID NO: 1).

gRNAs are incubated in the corresponding buffer for 5 minutes at 95° C., followed by a progressive ramp at 80° C., 50° C., 37° C. and room temperature for 10 minutes at each step for annealing and/or secondary structure formation.

Example 2: Example of a Reaction Protocol for the Isolation of a Nucleic Acid Molecule Comprising a Target Region 1. Guide RNA (e.g. crRNA) is loaded onto the Class 2 Type V Cas protein by incubation for 10 minutes at room temperature (e.g. 25° C.) in the appropriate reaction buffer (50 mM NaCl, 10 mM Tris-HCl, 10 mM $MgCl_2$, 10 mM DTT, 100 µg/ml BSA, pH 7.9), thereby allowing the formation of the protein-RNA complex.

2. The loaded complexes prepared in step 1 are added to a sample comprising nucleic acid molecules in NEB buffer 2.1 supplemented with an extra 10 mM of DTT. The reaction tube is supplemented with 1 µl of Exo I (100 units) and incubated for at least 1 hour at 37° C. This will allow the Class 2 Type V Cas protein-gRNA complex to bind and cleave the nucleic acid at a site adjacent to a nucleic acid target region and Exo I to recess the 3' end of the non-target strand.

3. The reaction is stopped by adding "Stop buffer" (comprising a mixture of 1.2 units of Proteinase K and 20 mM EDTA), thereby removing the Class 2 Type V Cas protein-gRNA complex. In some cases, RNaseA may be added to digest the gRNA. RNaseA and Proteinase K treatments may notably be performed successively for 15 minutes at 37° C. In this case, addition of EDTA may be optional.

4. The sample may then be purified by any known technique, like bead or column purification, such as purification with paramagnetic beads.

5. The eluted DNA is then incubated with an oligonucleotide probe (in case of only one target) or multiple probes simultaneously (in case of multiple targets) for 30 min at 37° C. in the ThermoPol buffer (20 mM Tris-HCL, 10 mM $(NH_4)_2SO_4$, 10 mM KCl, 2 mM $MgSO_4$, 0.1% Triton® X-100, 1 mM NAD+, pH 8.8) (NEB). If the second site was also processed by a second Cas12a protein, a probe (or multiple probes depending on the number of targets) containing a hairpin loop can be added to the reaction mixture at the same time. Each probe is added at a concentration of between 20 to 50 nM depending on the starting material. The reaction may also be supplemented with 1 μl of FEN1 (e.g. 32 units) and 1 μl of Taq DNA ligase (e.g. 40 units).

6. The sample may then be purified by any known technique, like bead or column purification, such as purification with paramagnetic beads.

7. In cases where the oligonucleotide probe does not comprise a ligand, a universal oligonucleotide probe containing a 5' biotin ligand to produce a Y-shaped structure, may be added to the eluted DNA from step 6 at a concentration of 100 nM. The gap between this oligonucleotide and the 5' end of the duplex region (and the hairpin loop if used) is then filled-in by Bst Full Length DNA Polymerase (0.2 units with 0.2 mM of dNTPs) and sealed by supplementing the reaction with 1 mM of NAD and 40 units Taq DNA ligase for 30 min at 50° C. in ThermoPol buffer (NEB).

8. The sample may then be purified by any known technique, like bead or column purification, such as purification with paramagnetic beads.

9. The sample is incubated with paramagnetic beads coated with streptavidin for 30 min at room temperature (25° C.) in the binding buffer recommended by the magnetic bead manufacturer (for example, but not limited to, 0.5 M NaCl, 20 mM Tris-HCl (pH 7.5), 1 mM EDTA).

10. Beads are then washed using the recommended Wash buffer (for example, but not limited to, 0.5 M NaCl, 20 mM Tris-HCl (pH 7.5), 1 mM EDTA, with or without 0.5% Tween-20) and can be used for downstream applications, such as sequencing or detection of epigenetic modifications.

Example 3: Determination of the Overhang Generated by LbaCas 12a Coupled with ExoI To determine the 5' overhang generated by the simultaneous treatment of a nucleic acid with Cas12a and ExoI, a 221 base pair (bp) PCR fragment containing the site recognized by the SEPT9.2 crRNA #1 sequence was amplified using primers PS1462 and PS1464 (SEQ ID NOs: 4 and 5) with OneTaq DNA polymerase (NEB) (SEQ ID NO: 3). As PS1464 comprises a 5' FITC, the strand containing the PAM sequence 5' TTTV 3' was tagged with FITC. Three more PCR fragments of 128, 273 and 503 bp were generated with the same PS1464 reverse primer (therefore also tagged with FITC) but with three different forward primers PS1461, PS1463 and PS1131 (SEQ ID NOs: 22, 23 and 24 for the oligonucleotides and SEQ ID NOs: 6 to 8 for the PCR fragment) using OneTaq (NEB). These three PCR fragments serve as markers for the analysis of the fragment lengths of the resulting reactions.

To determine the cleavage position of LbaCas12a (NEB) on the target and non-target strands with and without ExoI treatment, 150 ng of the 221 bp PCR fragment tagged with FITC was incubated with either LbaCas12a:crRNA complex (at a ratio of 1:10:20 for DNA:Cas12a:crRNA) or simultaneously with LbaCas12a complex and 25 units of ExoI. A third reaction was prepared where the PCR fragment was incubated with only LbaCas12a:crRNA and the 5' overhang was filled in with T4 DNA polymerase (NEB) to determine the cleavage position on the 5' of the target strand to which the crRNA hybridizes (see FIG. 1A-1C). The three resulting reactions were run on a capillary electrophoresis system (Abi 3730) to resolve the fragments tagged with FITC present in the reaction at single base resolution. The three PCR fragments tagged with FITC of known sizes were spiked-in with the reaction and used as markers for determination of the size of the unknown fragments.

As shown in FIG. 1B, treatment with ExoI surprisingly allows a longer 5' overhang to be produced. This is in notable contrast to the 5' overhang lengths described in the art, and that obtained with LbaCas12a alone here (which may be, for example, as few as 6 bases in length, from position −13 to −19 in relation to the PAM). Indeed, ExoI treatment displaces the cleavage on the non-target strand containing the PAM sequence by at least two extra bases, when compared with the closest cleavage position from the PAM of LbaCas12a in the absence of ExoI (the cleavage position on the non-target strand may furthermore be displaced by up to 5 bases). The 5' overhang obtained with Cas12a-gRNA and ExoI treatment is also surprisingly better defined. As shown in FIGS. 1B and 1C, less variability in cleavage of the non-targeted strand is observed, in contrast to the cleavage positions observed in the absence of ExoI treatment. The 5' overhang generated by simultaneous treatment with LbaCas12a and ExoI is advantageously 11 or 12 nucleotides in length.

Example 4: The 5' Overhang Resulting from Cas 12a-gRNA and ExoI Treatment is Capable of Promoting Hybridization of an Oligonucleotide Probe A 287 bp PCR fragment (SEQ ID NO: 19) containing the site recognized by the human NDGR4.1 crRNA #1 (SEQ ID NO: 20) was tagged with FITC at the 5' end of the non-target strand containing the 5'-TTTV-3' PAM sequence. The PCR fragment was first incubated with the LbaCas12a-crRNA #1 complex to create the overhang. The reaction was stopped and purified. An oligonucleotide probe comprising biotin at its 3' end as well as a sequence complementary to the 5' overhang at its 5' end was added to the eluted DNA and processed by FEN1 and ligated by Taq DNA ligase to the PCR fragment. Separate reactions were performed by incubating the LbaCas12a-crRNA #1 complex in the presence or absence of exonuclease VII (ExoVII, which has both 3' to 5' and 5' to 3' single-stranded exonuclease activity) or ExoI (having only 3' to 5' single-stranded exonuclease activity). The successful ligation of the biotin oligonucleotide probe is revealed by the presence of a larger sized fragment that appears close to the 273 bp marker in the capillary electrophoresis. The same FITC markers (129, 273 and 503 bp PCR fragments) were used as in Example 3 to align the different traces. The five different experiments were aligned based on the 129 and 273 bp fragments.

The percentage of successful ligation was calculated by dividing the fluorescent intensity of the corresponding ligated peak over the total fluorescence for all fragments having a 5' overhang. As shown in FIG. 9(A), after incubation of the PCR fragment with the LbaCas12a-crRNA #1 complex, the oligonucleotide probe, FEN1 and Taq DNA ligase, approximately 24% of the resulting fragments correspond to the ligated product. In contrast, no ligated product is present in the absence of FEN1 and Taq DNA ligase. As shown in FIG. 9(B), the ExoI treatment allows all the peaks present in A (which correspond to the different ends created by Cas12a activity) to collapse into two major peaks corresponding to positions −9 and −10 from the PAM sequence. While ExoVII treatment also generates peaks corresponding to positions −9 and −10 from the PAM sequence (FIG. 9(C)), the 3' end may not be as well recessed as additional peaks corresponding to Cas12a cleavage activity are still present, in addition to the −9 and −10 peaks.

In contrast to the results obtained in FIG. 9(A), when the fragment is further incubated with an exonuclease having 3' to 5' activity in presence of FEN1 and Taq DNA ligase, be it ExoI or ExoVII, a much higher percentage (i.e. about 50%) of the fragments now correspond to the PCR product which has been ligated with the probe (see FIGS. 9 (D) and (E)). Thus, efficiency of isolation of a target nucleic acid region using the method of the invention as advantageously improved when a population of nucleic acid molecules is contacted with an enzyme having at least 3' to 5' exonuclease activity. Indeed, as the oligonucleotide probe forms a stable duplex with the 5' overhang of a much greater number of fragments, the number of duplexes (and therefore the number of target regions) isolated by the method of the invention will also be improved.

Example 5: Quantification of Cleavage Efficiency by qPCR

We developed a quantitative PCR assay (qPCR, illustrated in FIG. 10) to determine the cleavage efficiency of Cas12a within the human genome. In brief, qPCR with oligonucleotides A and B (SEQ ID NOs: 94 and 95) allows us to quantify the amount of material present in the tube whereas qPCR with oligonucleotides A and C (SEQ ID NO: 96) only produces a product if the target is not cleaved by the Cas12a-crRNA complex. For increased specificity, we included a TaqMan probe (SEQ ID NO: 93) within the amplicon such that the same probe can be used for both qPCR reactions. By calculating the Ct ratio (i.e. ΔΔCt) of the qPCR A/C over A/B, it is possible to determine the percentage of molecules cleaved by the complex.

We incubated the Cas12a-crRNA complex targeting the human FMR1 promoter containing the CGG repeat region (SEQ ID NO: 57) for various amounts of time and at different ratios of complex:human genomic DNA to estimate the fraction of cleaved versus uncleaved fragment. To prepare the complex, the AsCas12a protein was incubated with twice the molar ratio of crRNA #2 gRNA specific to FMR1 (SEQ ID NO: 29) in NEB2.1 buffer (50 mM NaCl, 10 mM Tris-HCl, 10 mM $MgCl_2$, 100 µg/ml BSA, pH 7.9 at 25° C.) supplemented with 10 mM DTT for 10 min at room temperature.

In the first experiment, we estimated the time required for the Cas12a-crRNA complex to cleave its target within the human genome. 2 µg of human genomic DNA purified from a human embryonic kidney cell line (HEK293) were incubated with 600 fmol of the Cas12a-crRNA complex (for a ratio of 640,000 Cas12a-crRNA complex per human genome) in NEB2.1 buffer supplemented with 10 mM DTT for 10, 20, 30 and 60 min at 37° C. As a control, we incubated the same amount of genomic DNA at 37° C. in the same buffer conditions but without the Cas12a complex. We performed qPCR reactions with either the primer pair A and B or A and C on all the samples (and in triplicate) and using the quantification method described above, and observed that 78% of the targets are cleaved by this Cas12a-crRNA complex after only 30 minutes (FIG. 11). No increase in cleavage efficiency was observed by increasing the incubation time up to 60 minutes.

Next, an optimum ratio of Cas12a-crRNA complex per DNA molecule for a given incubation time (10 minutes) was determined in view of obtaining a maximum cleavage efficiency. 2 µg of human genome DNA was incubated with either 300, 600, 1200 or 1800 fmol of Cas12a complex (which corresponds to ratio of 320,000, 640,000, 1,280,000 and 1,600,000 complexes per human genome respectively) in NEB2.1 buffer supplemented with 10 mM DTT for 10 min at 37° C. As seen in FIG. 11, the best ratio of Cas12a-crRNA complex to human genome was 1,280,000 as 84% of cleaved target was obtained in these conditions. Further increasing the quantity of complex (1800 pmol) did not improve cleavage efficiency. As efficiency was not increased above 84% (which is similar to 600 pmol for the 30 minutes incubation time), we determined that the reaction could preferably be incubated for at least 30 minutes with a ratio of 640,000 Cas12a-crRNA complexes per human genome.

Example 6: Quantification of the Efficiency of Oligonucleotide Probe Ligation on the Overhang Created by Cas 12a with or without ExoI Using qPCR To confirm the results obtained using capillary electrophoresis in Example 4, we developed a qPCR assay to quantify the efficiency of FEN1 and ligation of the oligonucleotide probe on the overhang generated by either Cas12a-crRNA alone or Cas12a-crRNA and the exonuclease ExoI. In order to quantify this efficiency, two sets of primers were used along with a TaqMan probe (illustrated in FIG. 10). Oligonucleotides A and B (SEQ ID NOs: 94 and 95) were used as an internal control to quantify the amount of DNA present in the reaction tube (to normalize all the reactions) and oligonucleotides A and D (specific for the ligated probe; SEQ ID NOs: 94 and 97)) were used to determine the efficiency of ligation as it is only in case of ligation that the qPCR product resulting from the use of oligonucleotides A and D will be amplified. Relative quantification of the amount of probe ligation fragment (primer set A/D, SEQ ID NOs: 94/97) was normalized by the total amount of material (primer set A/B, SEQ ID NO: 94/95). Relative quantification was then normalized to 100% using the "standard reference reaction" (Cas12a cleavage in presence of ExoI and the FEN1 reaction at 37° C. for 30 min). This ratio was used compared between different experimental condition, as described in these examples.

Initially, 2 µg of human genome DNA purified from the human embryonic kidney cell line (HEK293) with 600 fmol of Cas12a complex in NEB2.1 buffer supplemented with 10 mM DTT for 30 min at 37° C. with or without 100 units of Exonuclease I. As a control, we incubated the same amount of DNA at 37° C. in the same buffer conditions but without the Cas12a complex. Reactions were stopped using the Stop Reaction buffer (1.2 units of Proteinase K and 20 mM of EDTA) and then purified by paramagnetic beads using the manufacturer's recommendations (KAPA beads, Roche).

A target specific oligonucleotide (SEQ ID NO: 98) with 20 bases complementary to the site recognized by the crRNA (thus complementary to the 5'-overhang created by Cas12a and exonuclease I, see FIG. 8) was added to the reaction tube with the Thermostable Flap Endonuclease 1 (FEN1, NEB) and Taq DNA Ligase (NEB) in ThermoPol Buffer for 30 min at 37° C. The oligonucleotide probe also contains a universal sequence at its 3' end, which is complementary to the qPCR oligonucleotide D. All of these reactions were quantified using primer pairs A/B and A/D into two separate tubes. Each qPCR reaction was performed in triplicate.

No difference in cleavage efficiency was observed when Exonuclease I was added to the reaction tube along with Cas12a-crRNA, as almost 80% of the fragments were cleaved in both conditions (FIG. 12A). However, a 50% decrease in efficiency of ligation of the oligonucleotide probe by FEN1 and Taq DNA ligase was observed when Exonuclease I was not present (FIG. 12B). The control reaction (without Cas12a) was used as a control for the relative quantification. These results agreed with what was observed using capillary electrophoresis (from 24% efficiency without ExoI to 54% with treatment with ExoI during Cas12a cleavage, FIG. 9).

Example 7: Influence of Temperature on Ligation of the Target Specific Oligonucleotide Probe with FEN1 and Taq DNA Ligase To determine the effect of the temperature of incubation on FEN1 and ligase activity, we tested three temperatures within their range of activity (37° C., 45° C. and 55° C.) and determined the efficiency of the ligation of the probe when the overhang created by the cleavage of Cas12a was enlarged by Exonuclease I. To determine this effect, two reaction conditions were prepared by incubating, in the presence or absence of 100 units of Exonuclease 1, 2 μg of human genomic DNA (HEK293) with 600 fmol of Cas12a/crRNA #2 guide RNA specific to FMR1 (SEQ ID NO: 29) in NEB2.1 Buffer supplemented with 10 mM DTT, for 30 min at 37° C. The reactions were stopped using Stop Reaction buffer (1.2 units of Proteinase K and 20 mM of EDTA) and then purified by paramagnetic beads using the manufacturer's recommendations (KAPA beads, Roche). 10 pmol of the target specific oligonucleotide (SEQ ID NO:: 98) with 20 bases complementary to the site recognized by the crRNA was added to the reaction tube with 1 mM NAD, 40 units of Taq DNA Ligase (NEB), 32 units of the Thermostable Flap Endonuclease 1 (FEN1, NEB) for 30 min at either 37° C., 45° C. or 55° C. Another reaction without the FEN1 was performed at each temperature in order to determine non-specific amplification. Quantitative PCR reaction were performed using two sets of primers (A/B and A/D, respectively SEQ ID NOs: 94-95 and 94-97) with the Taqman probe (SEQ ID NO: 93) and were performed in triplicate for each qPCR reaction. Relative quantification of probe ligation fragment (primer set A/D) was normalized by the total amount of material (primer set A/B) and quantification was then normalized using the "standard reference reaction" (Cas12a cleavage in presence of Exonuclease I and the FEN1 reaction at 37° C. for 30 min), as described above (Example 6).

As shown in FIG. 13, temperature does not affect the ligation improvement conferred by exonuclease I, for which ligation efficiency was doubled. An increase in the overall efficiency of ligation and/or FEN1 activity was, however, observed when the reaction was incubated at 45° C. (1.8× more probe ligation than at 37° C.).

Example 8: Hairpin Construction from Isolated Target Regions

The method illustrated in FIG. 6 and according to Example 2 was performed using 1.6 μg of E. coli genomic DNA. Specifically, the genomic DNA was incubated with 2 pmol of LbaCas12a-crRNA complex, with the regions of interest (targets #1 and 2, SEQ ID NOs: 9 and 10) being flanked on either side by two different Cas12a-crRNA complexes (SEQ ID NOs: 11 to 14), said complexes binding to a first and second site, respectively. The use of two Cas12a-gRNA complexes per target region advantageously increases specificity and limits the number of steps of the method (e.g. fragmentation is not necessary and Cas12a-gRNA complexes may be added simultaneously). Furthermore, the use of two different Cas12a-gRNA complexes advantageously allows for two different, specific 5' single stranded overhangs to be generated, which can be used in later steps to produce molecules suitable for the desired downstream application. The LbaCas12a-crRNA reaction was supplemented with 100 units of ExoI, which generated the 5' overhang required for the method to work efficiently. The reaction was stopped using the Stop Reaction buffer (1.2 units of Proteinase K and 20 mM of EDTA) and then purified by paramagnetic beads using manufacturer's recommendations (KAPA beads, Roche).

Target specific oligonucleotide probes having, at their 5' end, 20 bases that are complementary to the site recognized by the crRNA (thus complementary to the 5' overhang created by the Cas12a and exonuclease I) are added to the reaction tube with Thermostable Flap Endonuclease 1 (FEN1) and Taq DNA Ligase (see also FIG. 6). The oligonucleotide probe further comprises a region of known sequence at its 3' end, which remains single-stranded, thereby forming a 3' overhang (see also FIG. 8). Advantageously, all oligonucleotide probes may comprise the same 3' sequence, which is therefore considered to be "universal" as shown in FIG. 8. In the present case, the oligonucleotide PS1465 or PS1467 (SEQ ID NO: 17 and 18), having a 5' biotin ligand, is hybridized to the known sequence on the oligonucleotide probe, and the gaps were filled-in and sealed using Bst Full length DNA polymerase and Taq Ligase. This allows for the generation of the Y-shaped adaptor, which will enable the molecule to be used in downstream analyses on the SIMDEQ platform. The resulting nucleic acid fragments are purified with paramagnetic beads using manufacturer's recommendations (KAPA beads, Roche).

These two targets contain the non-palindromic restriction enzyme BsaI site with the same four base overhang at the site located on the other side of the target region in relation to the Y-adaptor, to which the hairpin adaptor PS421 (SEQ ID NO: 69) was hybridized and ligated. The BsaI reaction was incubated for 30 min at 37° C. in Cutsmart® Buffer (50 mM Potassium Acetate, 20 mM Tris-acetate, 10 mM Magnesium Acetate, 100 μg/ml BSA, pH 7.9) and the reaction was purified with paramagnetic beads using manufacturer's recommendations (KAPA beads, Roche). Ligation was then performed using T4 DNA ligase in T4 DNA ligase Buffer (50 mM Tris-HCl, 10 mM MgCl$_2$, 1 mM ATP, 10 mM DTT, pH 7.5) with 10 pmol of the hairpin adaptor for 30 min at room temperature. The ligated product is then purified with paramagnetic beads using manufacturer recommendations (KAPA beads, Roche).

The prepared target regions were then analyzed on our SIMDEQ platform in order to assess the specificity of the method and to detect expected peaks using a CAAG four-base oligonucleotide. Traces of the binding positions are represented in FIGS. 15A and 15B and show that all expected peaks were properly identified. No other hairpin molecules were present in the flow-cell, indicating a specificity of 100%. This is in notable contrast to existing methods of hybrid capture, which show 15-25% off-target capture.

Example 9: Hairpin Construction Using Human Genomic DNA

We used the protocol illustrated in FIG. 14 provided above with Cas12a and Exonuclease I followed by the FEN1 and ligation step to construct hairpin molecules suitable to be analyzed on a SIMDEQ instrument. Briefly, 5 µg of human genomic DNA was incubated with 600 fmol of each Cas12a-crRNA complex (SED ID NOs: 28 and 29) flanking the FMR1 target region (SEQ ID NOs: 65) and 100 units of Exonuclease I in NEB2.1 Buffer supplemented with 10 mM DTT, for 30 min at 37° C. Reactions were stopped using the Stop Reaction buffer (1.2 units Proteinase K, 20 mM EDTA) and purified by paramagnetic beads using the manufacturer's recommendations (KAPA beads, Roche).

The resulting DNA was then incubated with 10 pmol each of two oligonucleotide probes, a first one being complementary to the 5' overhang generated by the Exonuclease I on the cleavage site of Cas12a-crRNA #1 (SEQ ID NO 100) and a second one being complementary to the 5' overhang of Cas12a-crRNA #2 (SEQ ID NO 99) containing a biotin ligand at its 3' end and an abasic site modification (THF or Tetrahydrofuran) within its sequence as well as 30 units of FEN1 to cleave the 5' Flap and create a nick. This nick was sealed by using 40 units of the Taq DNA Ligase in ThermoPol reaction buffer supplemented with 1 mM NAD+. After 30 minutes at 45° C., two specific oligonucleotides (SEQ ID NOs: 101 and 97) are hybridized to the known sequence on the oligonucleotide probe, and the gaps were filled-in and sealed using Bst Full length DNA polymerase supplemented with 200 nM dNTP. This allows for the generation of the Y-shaped adaptor (which will enable the molecule to be used in downstream analyses on the SIMDEQ platform) and a dsDNA duplex surrounding the abasic site (3 bp after the abasic site is dsDNA). The resulting nucleic acid fragments are captured with streptavidin paramagnetic beads and enriched.

Specifically, target molecules are eluted from beads by Endonuclease IV in NEB3 buffer (100 mM NaCl, 50 mM Tris-HCl, 10 mM MgCl2, 1 mM DTT, pH 7.9 at 25° C.) for 30 min at 37° C., which catalyzes the cleavage of the DNA phosphodiester backbone at abasic sites via hydrolysis, leaving a 1 nucleotide gap with a 3'-hydroxyl termini, generating a 4 bp 5' overhang. This overhang then is used to ligate the hairpin adaptor via a reaction using T4 DNA ligase in T4 DNA ligase Buffer (50 mM Tris-HCl, 10 mM $MgCl_2$, 1 mM ATP, 10 mM DTT, pH 7.5) with 10 pmol of the hairpin adaptor for 30 min at room temperature.

Example 10: Enrichment of Target Regions from Human Genomic DNA

Human genomic DNA was purified from Human embryonic kidney cell line (HEK293). Cas12a guides RNA (SEQ ID NOs: 2, 20 and 25 to 52) were designed to target the first and second sites flanking the target regions (SEQ ID NOs: 53 to 68). We selected 15 different human targets known to be either epigenetic markers implicated in cancer or composed of STRs (Short-tandem repeats) known to cause disease in humans (see FIG. 16A). The first step of the method was performed by incubating 10 µg of genomic DNA with 390 fmol of each Cas12a-crRNA complex and 800 units of Exonuclease I for 2 hours at 37° C. to generate the 5' overhang. The reaction was stopped by adding the Stop buffer and purified using KAPA beads (Roche), according to the manufacturer's instructions.

Oligonucleotide probes (SEQ ID NOs: 21 and 70 to 83) containing a biotin ligand at their 3' end were synthesized such that their 5' ends were complementary to the generated 5' overhang. Due to the variability in the cleavage position of the non-target strand (see FIG. 1C), the probes were designed such that their 5' ends contain the PAM sequence and an additional 5 bases after the PAM sequence. This 5' flap sequence complementary to the site recognized by the crRNA corresponds to a typical substrate for the FEN1 enzyme. These oligonucleotides also comprise the restriction sites recognized by three restriction enzymes: DdeI (C^TNAG), HinfI (G^ANTC), and AluI (AG^CT).

The eluted DNA treated with LbaCas12a-crRNA complex and ExoI was supplemented with 6 pmol of probe as well as 30 units of FEN1 to cleave the 5' Flap and create a nick. This nick was sealed by using 40 units of the Taq DNA Ligase in reaction buffer (20 mM Tris-HCl, 10 mM $(NH_4)_2SO_4$, 10 mM KCl, 2 mM $MgSO_4$, 0.1% Triton® X-100, 1 mM NAD+, pH 8.8). Thus, a duplex was formed between the probe and the 5' overhang. After 30 minutes at 37° C., 30 units of RecJF (a 5' to 3' ssDNA exonuclease) was added to digest the non-ligated oligonucleotides. The ligated product was then purified with paramagnetic beads using manufacturer recommendations (KAPA beads, Roche) and the resulting DNA preparation was captured using paramagnetic beads coated with streptavidin (Ocean Nanotech) for one hour in the same reaction buffer as the FEN1 reaction. Beads bound with the duplex (and therefore the DNA target region) were split into three reactions, each reaction being treated with a different restriction enzyme (DdeI, AluI or HinfI), which allowed the DNA target region to be cleaved from the beads and become a template for Illumina library preparation. We used the NEB Ultra II kit for low starting materiel and followed the manufacturer's protocol to prepare the library. The sequencing reaction was performed on a NextSeq 500 Illumina sequencer with pair-end sequencing (150 base pairs on each side). Reads were aligned using the Bowtie algorithm on the human reference genome and coverage calculation was performed using Samtools. Reads were visualized using IGV software. The representative coverage of one of the targeted regions (SNCA) is shown in FIG. 16B (extract of a screenshot from IGV software). Maximum coverage obtained within this target region was very high (614×) compared to the remaining genomic DNA, which was less than 1× on average.

The invention claimed is:

1. A method of isolating a nucleic acid target region from a population of nucleic acid molecules, the method comprising the steps of:

a) contacting the population of nucleic acid molecules with a Class 2 Type V Cas protein-gRNA complex, wherein the gRNA comprises a guide segment that is complementary to a first site adjacent to the target region, thereby forming a Class 2 Type V Cas protein-gRNA-nucleic acid complex, b) contacting the population of nucleic acid molecules comprising the Class 2 Type V Cas protein-gRNA-nucleic acid complex with at least one enzyme having single-strand 3' to 5' exonuclease activity, thereby forming a 5' single-stranded overhang in the first site, c) removing the Class 2 Type V Cas protein-gRNA complex from the population of step b), d) contacting the population of step c) with an oligonucleotide probe, the probe comprising a sequence that is at least partially complementary to the overhang, thereby forming a duplex between the probe and the overhang, and e) isolating the duplex from the population of nucleic acid molecules of step d), thereby isolating the nucleic acid target region.

2. The method of claim 1, wherein the Class 2 Type V Cas protein is Cas12a or C2c1.

3. The method of claim 1 further comprising contacting the population of nucleic acid molecules with a site-specific endonuclease prior to step c).

4. The method of claim 3, wherein the site-specific endonuclease is selected from the group consisting of a TALEN, a zinc-finger protein, and a Class 2 Cas protein-gRNA complex, wherein when the site-specific endonuclease is a Class 2 Cas protein-gRNA complex the gRNA comprises a guide segment that is complementary to a second site adjacent to the target region, and wherein the first site and the second site are located on either side of the target region.

5. The method of claim 1, wherein the at least one enzyme having single-strand 3' to 5' exonuclease activity is selected from the group consisting of exonuclease I, S1 exonuclease, exonuclease T, and exonuclease VII.

6. The method of claim 5, wherein the at least one enzyme having single-strand 3' to 5' exonuclease activity is exonuclease I.

7. The method of claim 1, further comprising fragmenting the population of nucleic acid molecules prior to or during step b).

8. The method of claim 7, wherein fragmenting occurs by contacting the population of nucleic acid molecules with at least one site-specific endonuclease, wherein the site-specific endonuclease:

does not cleave within the target region or the first site, and does not cleave within the second site when the molecule comprises a second site.

9. The method of claim 1, wherein step c) comprises contacting the population of nucleic acid molecules with EDTA and/or at least one protease.

10. The method of claim 9, wherein the at least one protease is a serine protease.

11. The method of claim 10, wherein the serine protease is proteinase K.

12. The method of claim 1, further comprising releasing the duplex from the target region.

13. The method of claim 12, wherein releasing the duplex from the target region comprises cleaving within the duplex.

14. The method of claim 3, wherein when the site-specific endonuclease is a second Class 2 Type V site-specific endonuclease, the population is contacted with a second oligonucleotide probe comprising a sequence that is at least partially complementary to a second 5' single-stranded overhang in a second site adjacent to the target region, thereby forming a second duplex.

15. The method of claim 14, wherein the first and second probes comprise different ligands, the ligands binding to different capture agents.

16. The method of claim 1, wherein the 5' single-stranded overhang in the first site has a length of at least 9 nucleotides.

17. The method of claim 14, wherein step e) comprises:

contacting the first duplex with a first capture agent, the first capture agent binding the ligand of the first probe, releasing the first duplex from the target region, contacting the second duplex with a second capture agent, the second capture agent binding the ligand of the second probe, releasing the second duplex from the target region.

18. The method of claim 1, wherein the target region comprises a repeat region, a rearrangement, a duplication, a translocation, a deletion, or a modified base.

19. The method of claim 1, wherein at least two target regions are isolated.

\* \* \* \* \*